(12) United States Patent
Erlanger et al.

(10) Patent No.: US 6,593,137 B1
(45) Date of Patent: Jul. 15, 2003

(54) ANTIBODIES SPECIFIC FOR FULLERENES

(75) Inventors: Bernard F. Erlanger, Whitestone, NY (US); Bi-Xing Chen, Palisades Park, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/386,658

(22) Filed: Aug. 31, 1999

(51) Int. Cl.$^7$ .......................... C12N 5/20; C12N 15/13; C07K 16/44; C12P 21/08; G01N 33/53

(52) U.S. Cl. .................. 435/345; 435/7.1; 435/7.5; 435/7.93; 435/70.21; 435/452; 436/548; 530/388.9; 530/807; 536/23.53

(58) Field of Search ................ 435/6, 7.1, 7.5, 435/7.92, 7.93, 7.95, 70.21, 326, 345, 452; 436/548; 530/387.1, 388.9, 389.1, 389.8, 807; 536/23.53; 935/104, 108, 110

(56) References Cited

PUBLICATIONS

Chen et al., 1998a. Antibodies to fullerenes and their properties. FASEB Journal 12 (5, 2Suppl): A887, Abstract #5135, Mar. 20, 1998.*

Chen et al., 1998b. Antigenicity of fullerenes: antibodies specific for fullerenes and their characteristics. Proc. Natl. Acad. Sci. USA 95: 10809–10813, Sep. 1998.*

Izhaky, D. and Pecht, I. (1998) "What else can the immune system recognize?", *Proc. Natl. Acad. Sci. USA*, 95:11509–11510. (Exhibit 3).

Andersson, T. et al., (1992) "$C_{60}$ Embedded in γ-Cyclodextrin: a Water–soluble Fullerene", *J. Chem. Soc. Chem. Comm.*, 604–606. (Exhibit 1).

Arevolo, J. H. et al., (1994) "Structural Analysis of Antibody Specificity Detailed Comparison of Five Fab' –Steroid Complexes", *J. Mol. Biol.* 241:663–690. (Exhibit 2).

Bensasson. R. V. et al. (1995) "Photophysical Properties of Three Hydrofullerenes", *Chem. Phys. Lett.* 245:566–570. (Exhibit 3).

Bethune, D.S. et al., (1993). "Atoms in Carbon Cages: the Structure and Properties of Endohedral Fullerenes", *Nature* 366:123–128. (Exhibit 4).

Electrogenerated $C_{60}$–Radical Monoanion in Water by Means of Cyclodextrin Inclusion Chemistry, *J. Phys. Chem.* 98:1282–1287. (Exhibit 5).

Buchanan, M.V., and R.L. Hettich (1993) "Fourier Transform Mass Spectrometry of High–Mass Biomolecules", *Anal. Chem.* 65: 245A–259A. (Exhibit 6).

Chai, Y. et al., (1991). "Fullerenes with Metals Inside," *J. Phys. Chem.* 95:7564–7569. (Exhibit 7).

Chiang, L. Y., Lu, J. T. & Lin, J. T. (1995) "Free Radical Scavenging Activity of Water–soluble Fullerenols", *J. Chem. Soc. Chem. Commun.*, 1283–1284. (Exhibit 8).

Chiang, L.Y. et al., (1992). "Multi–hydroxy Additions onto $C_{80}$ Fullerene Molecules," *J. Chem. Soc. Chem. Commun.*, 1791–1793. (Exhibit 9).

Clarke, A.R., Atkinson, T., and Holbrook, J.J., (1989) "From Analysis to Synthesis: New Ligand Binding Sites on the Lactate Dehydrogenase Framework. Part Two", *Trends in Bio. Sciences*, 14:145–148. (Exhibit 10).

David, W. I. F.(1991) "Crystal Structure and Bonding of Ordered $C_{60}$", *Nature* (London) 353:147–149. (Exhibit 11).

Dugan, L. L. et al. (1997) "Carboxyfullerenes as Neuroprotective Agents", *Proc. Natl. Acad. Sci. USA* 94:9434–9439. (Exhibit12).

Ebbesen, T.W., (1994) "Carbon Nanotubes," *Ann. Rev Material Sci.*, 24:235–264. (Exhibit 13).

Erlanger, B.F. (1980). "Preparation of Antigenic Hapten–Carrier Conjugates,"*Methods in Enzymology*, 70:85–104. (Exhibit 14).

Erlanger, B. F. et al., (1959) "Steroid–Protein Conjugates", *J. Biol. Chem.* 234:1090–1094. (Exhibit 15).

Erlanger, B. F. & Brand, E. (1951) "Optical Rotation of Peptides. III. Lysine Dipeptides", *J. Am. Chem. Soc.* 73: 4025–4027. (Exhibit 16).

Friedman, S. H. et al., (1993) "Inhibition of the HIV–1 Protease by Fullerene Derivatives: Model Building Studies and Experimental Verification", *J. Am. Chem. Soc.* 115: 6506–6509. (Exhibit 17).

Geckeler, K.E. and A. Hirsh (1993) "Polymer–Bound $C_{60}$" *J. Am. Chem. Soc.* 115:3850–3851. (Exhibit 18).

Gromov, A. et. al., (1997) "Extraction and HPLC Purification of Li@$C_{60/70}$,", *Chem. Commun.*, 2003–2004. (Exhibit 19).

Haddon, R. C. (1993) "Chemistry of the Fullerenes: The Manifestation of Strain in a Class of Continuous Aromatic Molecules", *Science* 261:1545–1550. (Exhibit 20).

(List continued on next page.)

Primary Examiner—Christopher L. Chin
Assistant Examiner—James L. Grun
(74) Attorney, Agent, or Firm—John P. White; Cooper & Dunham LLP

(57) ABSTRACT

This invention provides a hybridoma produced by the fusion of a mouse antibody-producing cell and a mouse myeloma which is designated 1-10F-8A and deposited with the ATCC under Accession Number PTA-279, said hybridoma producing a monoclonal antibody which binds to fullerene C60. This invention provides a mouse monoclonal antibody specific for a fullerene-C60 and produced by the mouse monoclonal antibody-producing hybridoma designated 1-10F-8A. The invention provides the amino acid and encoding nucleic acid sequences of the heavy and light chains of the 1-10F-8A monoclonal antibody. This invention also provides methods of determining a serum concentration of a fullerene in a subject and of purifying a fullerene from a sample.

7 Claims, 23 Drawing Sheets

PUBLICATIONS

Haufler, R.E., (1994). "Techniques of Fullerene Production," *The Electrochemical Society Inc.*, 50–67. (Exhibit 21).

Heath, J. R. et al., (1985). "Lanthanum complexes of Spheroidal Carbon Shells", *J. Am. Chem. Soc.* 107: 7779–7780. (Exhibit 22).

Hirsch, a., Lamparth, I. & Grosser, T. (1994) *J. Am. Chem. Soc.* 116:9385–9386. (Exhibit 23).

Isaacs, L. and F. Diederich (1993). "Structures and Chemistry of Methanofullerenes: A Versatile Route into N–[(Methanofullerene) caronyl] –Substituted Amino Acids", *Helv. Chem. Acta.* 76:2454–2464. (Exhibit 24).

Janeway, C.A., Jr. & Travers, P. (1996) *Immunobiology* (Garland Publishing Inc., New York and London), pp. 8:3–8:5. (Exhibit 25).

Jensen, A. W., Wilson, S. R. & Schuster, D.I. (1996) "Biological Applications of Fullerens", *Bioorg. Med. Chem.* 4:767–779. (Exhibit 26).

Jerne, N. K. (1974) "Towards a Network Theory of the Immune System", *Ann. Inst. Pasteur/Immunol* 125 C:373–389. (Exhibit 27).

Johnstone, A. & Thorpe, R. (1982) *Immunochemistry in Practice* (Blackwell Scientific, Oxford), pp. 122–125. (Exhibit 28).

Karam, L. R., M. Mitch, B. Coursey (1997). "Encapsulation of $^{99m}$Tc within Fullerenes: a Novel Radionuclide Carrier", *App. Radiat. Isot.* 48(6):771–776. (Exhibit 29).

Kikuchi, K. et al., (1994). "Encapsulation of Radioactive $^{150}$Gd and $^{161}$Tb Atoms in Fullerene Cages", *J. Am. Chem. Soc.* 116:9775–9776. (Exhibit 30).

Klibanov, A.M. (1989) "Enzymic Catalysis in Anhydrous Organic Solvents", *Trends Biochem Sci*, 14:141–144. (Exhibit 31).

Kratschmer, W. et al., (1990) "Solid $C_{60}$: a new Form of Carbon", *Nature* (London) 347:354–357. (Exhibit 32).

Kroto, H. W. et al., (1985) "$C_{60}$ Buckminsterfullerene" *Nature* (London) 318:162–163. (Exhibit 33).

Ku, H. H. et al., (1987) "Monoclonal Antibodies to Adenosine Receptor by an Auto–Anti–Idiotypic Approach", *J. Immunol.* 139:2376–2384. (Exhibit 34).

Lamb, L.D. et. al., (1992) "Extraction and STM Imaging of Giant Fullerenes", *Science* 255:1413–1416. (Exhibit 35).

Langman, R.E., (1992) "Molecular Economy and Antibody Function: The Evolution of a Protecton", *Int. J. Clin. Lab. Res.* 22:63–68. (Exhibit 36).

Leu, J–G et al., (1994) "Idiotypic mimicry and the assembly of a supramolecular structure; and anti–idiotypic antibody that mimics taxol in its tubulin–microtubule interactions", *Proc. Natl. Acad. Sci. USA*, 91:10690–10694. (Exhibit 37).

Lu, L.–H. et al., (1998) "The Possible mechanisms of the Antiproliferative Effect of Fullerenol, Polyhydroxylated $C_{60}$, on Vascular Smooth Muscle Cells", *Brit. J. Pharmacol.* 123:1097–1102. (Exhibit 38).

Meares, C. F. (1986). "Chelating Agents for the Binding of Metal Ions to Antibodies", *Nucl. Med. Bio.* 13:311–318. (Exhibit 39).

Meidine, M. F. et al., (1992) "Single Crystal X–Ray Structure of Benzene–Solvated $C_{60}$", *J. Chem. Soc. Chem. Comm.*, 1534–1537. (Exhibit 40).

Paganelli, G. et al. (1991) "Three–step monoclonal antibody tumor targeting in carcinoembryonic antigenpositive patients", *Cancer Research* 51:5960–5966. (Exhibit 41).

Rajewsky, K., Forster, I. & Cumano, A. (1987) "Evolutionary and Somatic Selection of the Antibody Repertoire in the Mouse", *Science* 238:1088–1094. (Exhibit 42).

Renn, O. et al., (1996) "New approaches to delivering metal–labeled antibodies to tumors: Synthesis and character–ization of new ciotinyl chelate conjugates for pre–targeted diagnosis and therapy", *J. Of Controlled Release* 39:239–249. (Exhibit 43).

Saunders, M. et al., (1996). "Noble Gas Atoms Inside Fullerenes", *Science* 271:1693–1697. (Exhibit 44).

Schinazi, R.F.et. al. (1994) "Anti–Human Immunodeficiency Virus, Toxicity in Cell Culture, and Tolerance in Mammals of a Water–Soluble Fullerene", in *Recent Advances in the Chemistry and Physics of Fullerenes and Related Materials*, ed., (Exhibit 45).

Schinazi, R. F. et al., (1993) "Synthesis and Virucidal Activity of a Water–Soluble, Configurationally Stable, Derivatized $C_{60}$ Fullerene", *Antimicrob. Agents Chemother.* 37:1707–1710. (Exhibit 46).

Schlom, J. et al., (1991). "Monoclonal Antibody–based Therapy of a Human Tumor Xenograft with a $^{177}$Lutetium–labeled Immunoconjugate", *Cancer Research* 1:2889–2896. (Exhibit 47).

Scrivens, W. a., Bedworth. P. V. & Tour, J. M. (1992) "Purification of Gram Quantities of $C_{60}$. A New Inexpensive and Facile Method", *J. Am. Chem. Soc.* 114:7917–7919. (Exhibit 48).

Sijbesma, R. et al., (1993) "Synthesis of a Fullerene Derivative for the Inhibition of HIV ENzymes", *J. M. Chem. Soc.* 115:6510–6512. (Exhibit 49).

Skiebe, A. et al., (1994) "[DBU]$C_{60}$ Spin Pairing in a Fullerene Salt", *Chem. Phys. Lett.* 220: 138–140. (Exhibit 50).

Snyder, S. L & Sobocinski, P.Z. (1975) "An Improved 2, 4, 6–Trinitrobenzenesulfonic Acid Method for the Determination of Amines", *Anal. Biochem.* 64:284–288. (Exhibit 51).

Stewart, C.B., (1993) "The Powers and Pitfalls of Parsimony" *Nature* 361:603–607. (Exhibit 52).

Subramanian, R. et al., (1994) "A Facile and Selective Method for the Solution–phase Generation of $C_{60}$–and $C_{60}{}^{2-}$", *J. Chem. Soc. Chem. Commun.*, 1847–1848. (Exhibit 53).

Sykes, T. et al., (1997). "Radiolabeling of Monoclonal Antibody B43.13 with Rhenium–188 for Immunoradiotherapy", *Appl. Tadiat. Isot.* 48(7), 899–906. (Exhibit 54).

Takata, M. et al., (1995). "Conformation by x–ray Diffraction of the Endohedral Nature of the Metallofullerene Y@$C_{82}$", *Nature* 377:46–49. (Exhibit 55).

Taylor, R. and D.R.M. Walton (1993). "The Chemistry of Fullerenes," *Nature* 363:685–693. (Exhibit 56).

Toniolo, C. et al., (1994) "A Bioactive Fullerene Peptide", *J. Med. Chem.* 37: 4558–4562. (Exhibit 57).

Vuillez, J. Ph. et al., (1997). "Two–step immunoscintigraphy for non–small–cell lung cancer staging using a bispecific anti–CEA/anti–indium–DPTA antibody and an indium–111–labeled DPTA dimer", *J. Nucl. Med.* 38:507–511. (Exhibit 58).

Wang, Y. et al., (1995) "A Superior Synthesis of [6,6]–Methanofullerenes: The Reaction of Sulfonium Yledes with $C_{60}$", *Tetrahedron Lett.* 36:6843–6846. (Exhibit 59).

Wilder, R., G. DeNardo, S. DeNardo (1996) "Radioimmunotherapy: Recent results and future directions", *J. Of Clinical Oncology* 14(4):1383–1400. (Exhibit 60).

Wurz, P. and K. R. Lykke (1992) "Multiphoton Excitation, Ionization, and Dissociation of $C_{60}$", *J. Phys. Chem.* 96:10129–10139. (Exhibit 61).

Yakobson, B.I., and Smalley, R.E., (1997) "Fullerene Nanotubes: C1,000,000 and Beyond", *American Scientist*, 85:324–337. (Exhibit 62).

Yamakoshi, Y., T. Yagami, K. Fukuhara, S. Sueyoshi, N. Miyata (1994) "Solubilization of Fullerenes into Water with Polyvinylpyrrolidone Applicable to Biological Tests", *J. Chem. Soc., Chem. Commun.*, 517–518. (Exhibit 63).

Yu. G. et al., (1995) "Polymer Photovoltaic Cells: Enhanced Efficiencies via a Network of Internal Donor–Acceptor Heterojunctions", *Science* 270:1789–1791. (Exhibit 64).

Yuanfang, Liu and Wu Chuanchu (1991) "Radiolabeling of Monoclonal Antibodies With Metal Chelates", *Pure and Appl. Chem.* 63(3):427–463. (Exhibit 65).

* cited by examiner

FIGURE 1
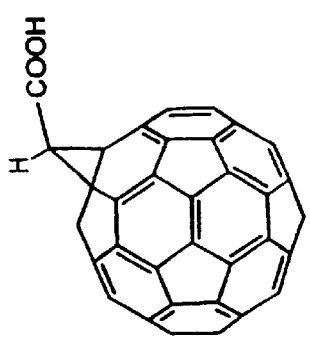
2
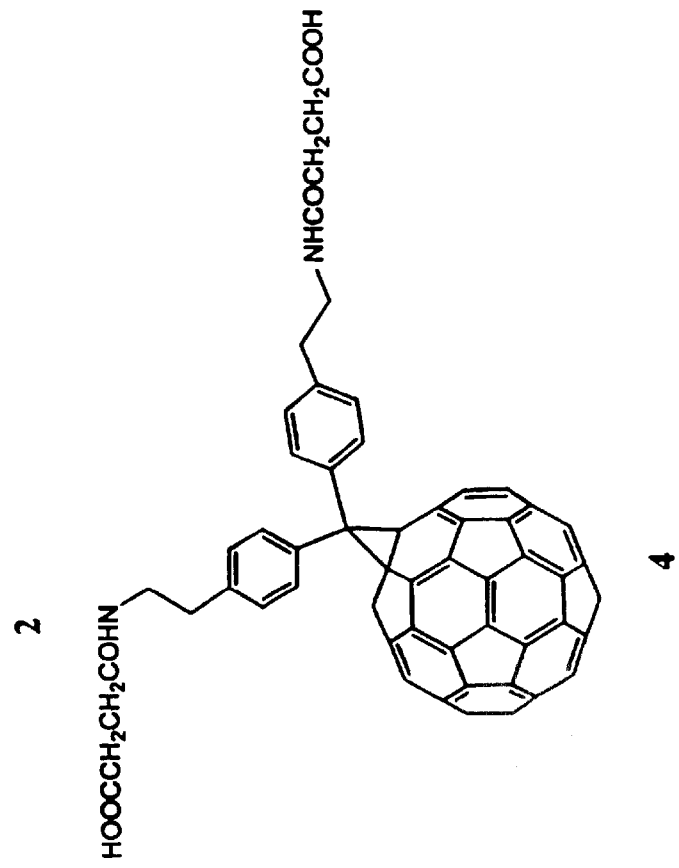
4
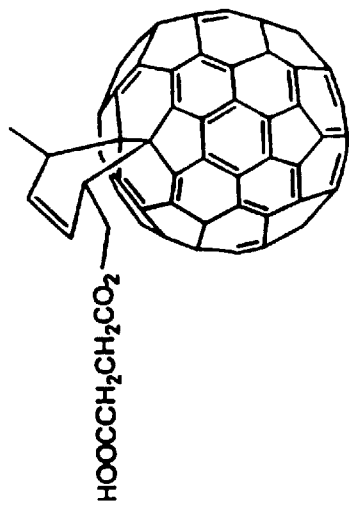
3 (isomer mixture)
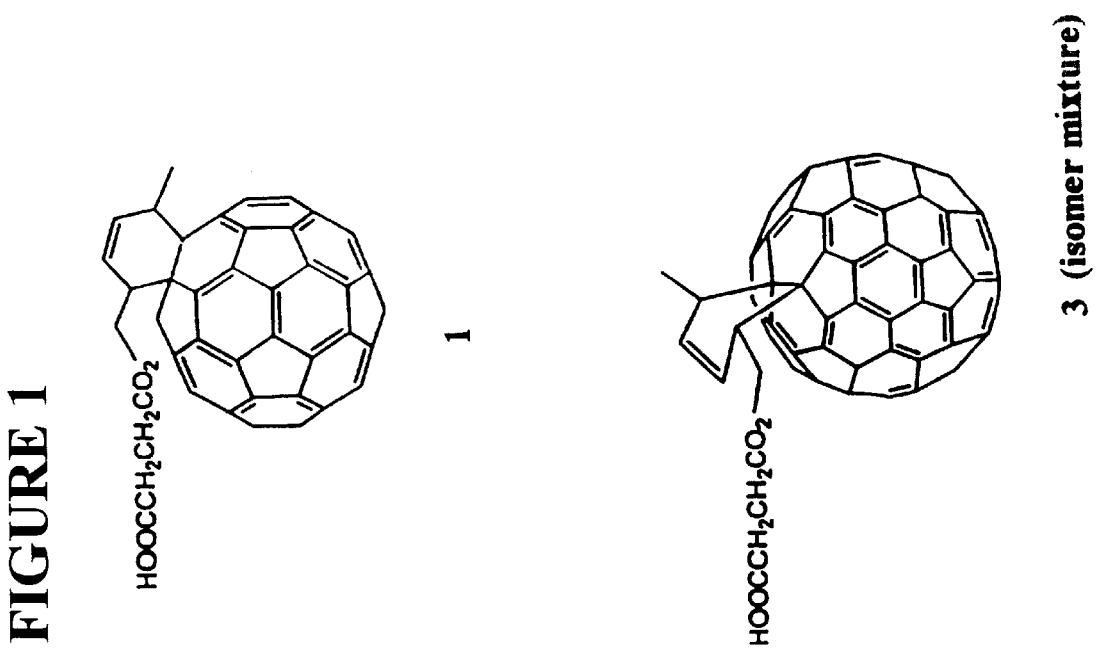
1

FIGURE 7A
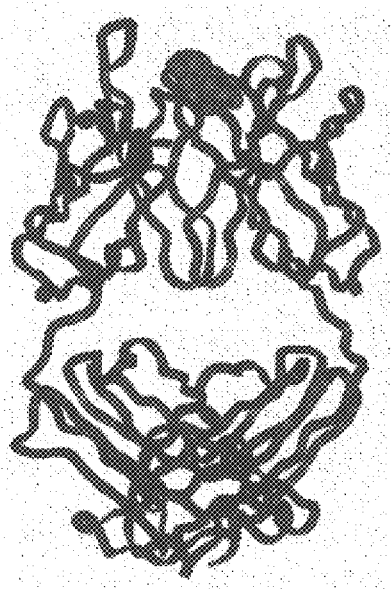
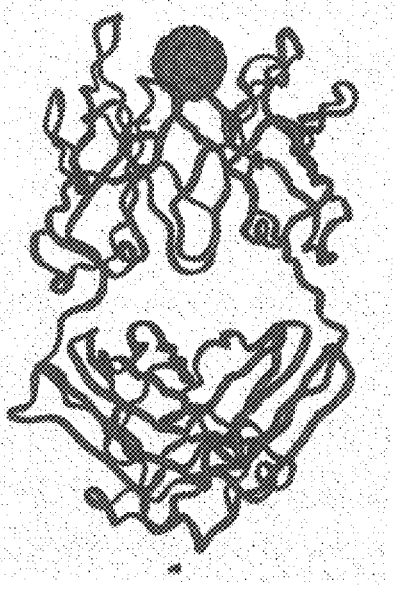
FIGURE 7B

FIGURE 20

H2-r 1-phase Translation

DNA sequence   398 b.p.   ATGGGATGCAGC....TGTCTCTGCAGC linear

```
1/1                                                        31/11
ATG GGA TGC AGC TGG GGC ATG CTC TTC CTC CTG TCA ATA ACT GCA GGT GTC CAT TGC CAG
 M   G   C   S   W   G   M   L   F   L   L   S   I   T   A   G   V   H   C   Q
61/21                                                      91/31
GTC CAC CTA CAA CAA TCT GGA CCT GAG CTG GTG AGG CCT GGG GCC TCA GTG AAG ATT TCC
 V   H   L   Q   Q   S   G   P   E   L   V   R   P   G   A   S   V   K   I   S
121/41                                                     151/51
TGC AAA ACT TCT GGC TAC GTA TTC AGT AGT AGT TCT TGG ATG AAC TGG GTG AAA CAG AGG CCT
 C   K   T   S   G   Y   V   F   S   S   S   S   W   M   N   W   V   K   Q   R   P
181/61                                                     211/71
GGA CAG GGT CTT AAG TGG ATT GGA CGA ATT TAT CCT GGA AAT GGA AAT ACT AAT TAC AAT
 G   Q   G   L   K   W   I   G   R   I   Y   P   G   N   G   N   T   N   Y   N
241/81                                                     271/91
GAG AAA TTC AAG GGC AAG GCC ACA CTG ACT GCA GAC AAA TCC TCC AAC ACA GCC TAC ATG
 E   K   F   K   G   K   A   T   L   T   A   D   K   S   S   N   T   A   Y   M
301/101                                                    331/111
CAG CTC AGC AGC CTG ACC TCT GTG GAC TCT GCG GTC TAT TTC TGT GCA ACA TCC TCG GCT
 Q   L   S   S   L   T   S   V   D   S   A   V   Y   F   C   A   T   S   S   A
361/121                                                    391/131
TAC TGG GGC CAA GGG ACT CTG CTC ACT GTC TCT GCA GC
 Y   W   G   Q   G   T   L   L   T   V   S   A
```

FIGURE 21

DNA sequence    327 b.p.    GATATCCAGATG .... ATAAAACGTAAG    linear

L16-F  1-phase Translation

```
1/1
GAT ATC CAG ATG ACA CAG ACT ACA TCC TCC CTG TCT GCC TCT CTG GGA GAC AGA GTC ACC
 D   I   Q   M   T   Q   T   T   S   S   L   S   A   S   L   G   D   R   V   T
61/21                                              31/11
TTC AGT TGC AGT GCA AGT CAG GAT ATT AAC AAT TAT TTA AAC TGG TAT CAG CAG AAA CCA
 F   S   C   S   A   S   Q   D   I   N   N   Y   L   N   W   Y   Q   Q   K   P
121/41                                             91/31
GAT GGA ACT ATT AAA CTC CTA ATC TAT TAC ACA TCA AGT TTA CGC TCA GGA GTC CCA TCA
 D   G   T   I   K   L   L   I   Y   Y   T   S   S   L   R   S   G   V   P   S
181/61                                             151/51
AGG TTC AGT GGT AGT GGG TCT GGG ACA GAT TAT TCT CTC ACC ATC AAC AAC CTG GAA CCT
 R   F   S   G   S   G   S   G   T   D   Y   S   L   T   I   N   N   L   E   P
241/81                                             211/71
GAA GAT ATT GCC ACT TAT TTT TGT CAG CAG TAT AGT AGG CTT CCG TTC ACG TTC GGC TCG
 E   D   I   A   T   Y   F   C   Q   Q   Y   S   R   L   P   F   T   F   G   S
301/101                                            271/91
GGG ACA AAG TTG GAA ATA AAA CGT AAG
 G   T   K   L   E   I   K   R   K
```

ANTIBODIES SPECIFIC FOR FULLERENES

This invention was made with support under Grant No. HL 47377-03 from the NIH. Accordingly, the United States Government has certain rights in the invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

The recent interest in using Buckminster fullerene (fullerene) derivatives in biological systems raises the possibility of their assay by immunological procedures. This, in turn, leads to the question of the ability of these unprecedented polygonal structures, made up solely of carbon atoms, to induce the production of specific antibodies. Immunization of mice with a $C_{60}$ fullerene derivative conjugated to bovine thyroglobulin yielded a population of fullerene-specific antibodies of the IgG isotype, showing that the immune repertoire was diverse enough to recognize and process fullerenes as protein conjugates. The population of antibodies included a subpopulation that crossreacted with a $C_{70}$ fullerene as determined by immune precipitation and ELISA procedures. These assays were made possible by the synthesis of water-soluble fullerene derivatives, including bovine and rabbit serum albumin conjugates and derivatives of trilysine and pentalysine, all of which were characterized as to the extent of substitution and their UV-Vis spectra. Possible interactions of fullerenes with the combining sites of IgG are discussed based on the physical chemistry of fullerenes and previously described protein-fullerene interactions. They remain to be confirmed by the isolation of mAbs for x-ray crystallographic studies.

Until 1985 there were only two known allotropic forms of carbon: graphite and diamond. In 1985, a novel allotrope was reported in which 60 carbon atoms were arranged as a truncated icosahedron, with 60 vertices and 32 faces, 12 of which were pentagonal and 20 hexagonal (1). It was dubbed Buckminsterfullerene (usually shortened to fullerene) because of its geodesic character, a name that has held through the present day. A detailed background of metallofullerenes is provided in section B.1 of the fourth series of experiments (infra).

Considerable activity followed this discovery particularly after procedures were developed to prepare fullerenes in workable quantities (2, 3). Various fullerene-based compounds have been prepared, and diverse uses were sought for them. Some were incorporated into photovoltaic cells (4) and nanotubes (5). Others were tested for biological activity (6), including antiviral (7, 8), antioxidant (9, 10), and chemotactic activities (11), and as neuroprotective agents in a mouse model of amyotrophic lateral sclerosis (12).

Practical application of fullerenes as biological or pharmacological agents requires that dosage and serum levels be capable of measurement, preferably by sensitive, simple immunological procedures. This, in turn, requires that specific antibodies to fullerenes be produced.

The clonal selection theory tells us that antigens elicit the production of antibodies by selecting for specific antibody producing cells already present in the repertoire of immunized animals (13). Although there is debate about the size of the "available" repertoire (14, 15), immunologists usually work on the assumption that the repertoire is diverse enough to be counted on to produce antibodies to "any" molecule a researcher may choose. This is, of course, an unreliable assumption, as experimental failures rarely find their way into the literature. The question that arises, therefore, is whether the immune repertoire is "complete" enough (15) to recognize and respond to the unprecedented geodesic structure of the fullerenes or sufficient aspects of it-more particularly, whether the immune system can process a fullerene-protein conjugate and display the processed peptides for recognition by T cells to yield IgG antibodies. We report here that it does.

SUMMARY OF THE INVENTION

This invention provides an antibody which is specific for a fullerene or derivative thereof, wherein the fullerene is selected from the group consisting of a fullerene carbon compound having from 20 to 540 carbon atoms.

This invention provides an antibody which is specific for a single-walled fullerene nanotube.

This invention provides a monoclonal antibody which is specific for a fullerene or derivative thereof, wherein the fullerene carbon compound or derivative thereof comprises a C60 fullerene, said antibody comprising an amino acid heavy chain sequence (SEQ ID NO:2) and an amino acid light chain sequence (SEQ ID NO:4).

This invention provides an antibody which is specific for a multi-walled fullerene nanotube.

This invention provides nucleic acid molecules which encode the monoclonal antibodies which are specific for a fullerene or derivative thereof, wherein the fullerene is selected from the group consisting of a fullerene carbon compound having from 20 to 540 carbon atoms.

This invention provides a nucleic acid molecule which encodes the monoclonal antibody which is specific for a single-walled fullerene nanotube.

This invention provides a nucleic acid molecule which encodes the monoclonal antibody which is specific for a multi-walled fullerene nanotube.

This invention provides a hybridoma produced by the fusion of a mouse antibody-producing cell and a mouse myeloma, said hybridoma producing a monoclonal antibody which is specific for a fullerene.

This invention provides a hybridoma produced by the fusion of a mouse antibody-producing cell and a mouse myeloma which is designated 1-10F-8A and deposited with the American Type Culture Collection (ATCC) under Accession Number PTA-279, said hybridoma producing a monoclonal antibody which binds to fullerene C60.

This invention provides a mouse monoclonal antibody specific for a fullerene-C60 and produced by the mouse monoclonal antibody-producing hybridoma designated 1-10F-8A and deposited with the ATCC under Accession Number PTA-279.

This invention provides a mouse monoclonal antibody specific for a fullerene-C60 and produced by the mouse monoclonal anti-fullerene antibody-producing hybridoma designated 1-10F-8A and deposited with the ATCC under Accession Number PTA-279, said antibody comprising a heavy chain sequence (SEQ ID NO:2) and a light chain sequence (SEQ ID NO:4).

This invention provides an antibody which is specific for a fullerene or derivative thereof, wherein the fullerene is selected from the group consisting of a fullerene carbon compound having from 20 to 540 carbon atoms, wherein the antibody is a polyclonal antibody.

This invention provides a monoclonal antibody which binds to a single-walled fullerene nanotube.

This invention provides a monoclonal antibody which binds to a multi-walled fullerene nanotube.

This invention provides a polyclonal antibody which binds to a single-walled fullerene nanotube.

This invention provides a polyclonal antibody which binds to a multi-walled fullerene nanotube.

This invention provides an antibody specific for a fullerene, wherein the fullerene is selected from the group consisting of a fullerene carbon compound or derivative thereof comprising from 20 to 540 carbon atoms, wherein a radioactive material is encapsulated in the fullerene.

This invention provides a method of determining a serum concentration of fullerenes in a subject which comprises: a) determining an amount of antibody which binds to the fullerene in the absence of serum; b) incubating a serum sample from a subject with an antibody which binds to the fullerene to form an antibody-fullerene complex; c) determining the amount of antibody which binds to the fullerene in the presence of serum by detecting the amount of fullerene complex; d) comparing the amount determined in step (c) with the amount determined in step (a), thereby determining the serum concentration of the fullerene in the subject.

This invention provides a method of purifying a fullerene from a sample which comprises: a) preparing an affinity chromatography column to which are bound antibodies which bind to the fullerene; b) adding a sample to the affinity chromatography column so as to allow the sample to flow through the column, thereby permitting the fullerene to bind to the antibodies, thereby forming a fullerene-antibody complex on the column; and c) separating the fullerenes from the antibody-fullerene complex of step (b) by altering the pH, thereby purifying the fullerene from the sample.

This invention provides a method of preparing a nanoscale device which comprises manipulating a single-walled fullerene nanotube or nanotubes with the above-described antibody which is specific for a single-walled fullerene nanotube to assemble electronic or chemical components of the nanoscale device.

This invention provides a method of preparing a nanoscale device which comprises manipulating a multi-walled fullerene nanotube or nanotubes with the above-described antibody which is specific for a multi-walled fullerene nanotube to assemble electronic or chemical components of the nanoscale device.

BRIEF DESCRIPTION OF THE FIGURES

FIG. 1. Fullerene derivatives used in this study.

FIGS. 7A–B. 7A. Binding of the progesterone analog, 5-α-pregnane-20-one-3-β-ol hemisuccinate to the Fab' fragment of a mAb specific for progesterone. This computer model was displayed in INSIGHT II from the x-ray crystal structure coordinates reported in ref. 26. Steroid is the dark cluster of spheres in the center at the top. 7B. The molecular docking of fullerene-C$_{60}$ by deletion of the steroid and manual docking using INSIGHT II. Fullerene is the sphere in the center at the top.

FIG. 20 Heavy chain sequence including leader of monoclonal antibody produced by mouse monoclonal anti-fullerene-hybridoma designated 1-10F-8A: 398 b.p. DNA sequence (SEQ ID NO:1) and encoded amino acid (SEQ ID NO:2).

FIG. 21 Light chain sequence of monoclonal antibody produced by miouse monoclonal anti-fullerene-hybridoma designated 1-10F-8A: 337 b.p. DNA sequence (SEQ ID NO:3) and encoded amino acid (SEQ ID NO:4).

FIG. 23 3-D crystal ltructure of the active site of a monoclonal antibody produced by the hybridoma produced by the fusion of a mouse antibody-producing cell and a mouse myeloma which is designated 1-10F-8A and deposited with the ATCC under Accessi n Number PTA-279, said hybridoma producing a monoclonal antibody which binds to fullerene C60.

DETAILED DESCRIPTION OF THE INVENTION

Figure 2:
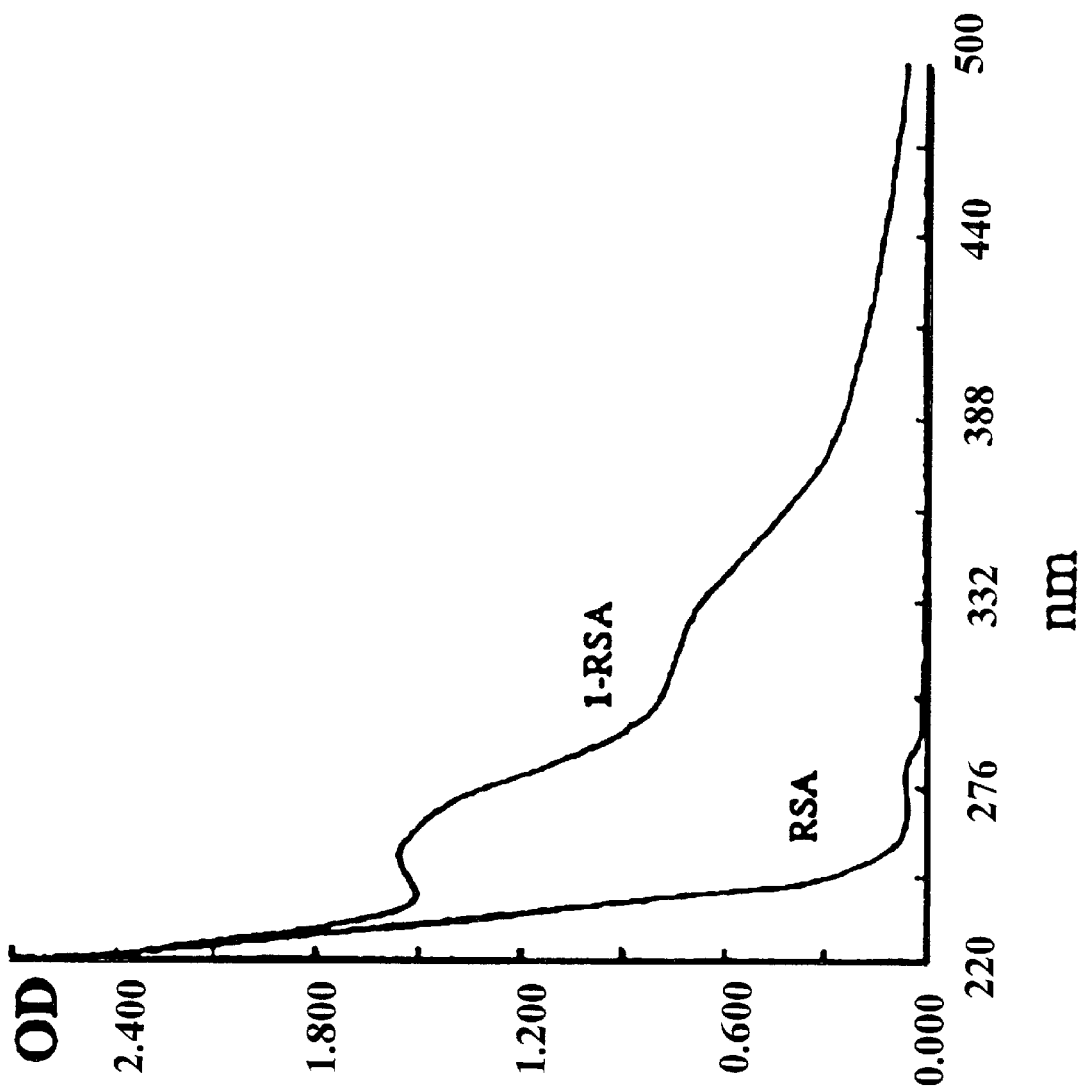
FIG. 2. UV-Vis spectrum of 1-RSA and RSA, Both at concentrations of 100 $\mu$g/ml in PBS.

This invention provides an antibody which is specific for a fullerene or derivative thereof, wherein the fullerene is selected from the group consisting of a fullerene carbon compound having from 20 to 540 carbon atoms.

In one embodiment, the above-described antibody which is specific for a fullerrene or derivative thereof, is a monoclonal antibody. In another embodiment of the above-described antibody which is specific for a fullerene or derivative thereof, the monoclonal antibody is a monospecific monoconal antibody. In an embodiment of the above-described antibody which is specific for a fullerene or derivative thereof, the fullerene carbon compound or derivative thereof comprises a C60 fullerene. In another embodiment of the above-described antibody which is specific for a lfulerene or derivative thereof, the fullerene carbon Compound or derivative thereof comprises a C70 fullerene. In a further embodiment of the above-described antibody which is specific for a fullerene or derivative thereof, the fullerene carbon compound or derivative thereof comprises a C76 fullerene. In another embodiment cof the above-described antibody which is specific for a fullerene or derivative thereof, the fullerene carbon compound or derivative thereof comprises a C78 fullerene. In a further embodiment of the above-described antibody which is specific for a fullerene or derivative thereof, the fullerene carbon compound or derivative thereof comprises a C84 fullerene. In another embodiment of the above-described antibody which is specific for a fullerene or derivative thereof, the fullerene carbon c(mpound or derivative thereof comprises a C240 fullerene.

This invention provides an antibody which is specific for a single-walled fullerene Inanotube. A nanotube (NT) is defined by the formula. "[n,m]-nanotube" wherein n=0–500, m=0–500, and n and m are the same or different integers, i.e. [5,5]-NT (same), [9,0]-NT (different), but most commonly [10,10]-NT (same). One of skill may refer for a more detailed description of nanotubes, for example, to Yakobson, B. I. and Smalley, R. E., American Scientist, 85:324 (1997) which is hereby incorporated by reference.

This invention provides a monoclonal antibody which is specific for a fullerene or derivative thereof, wherein the fullerene carbon compound or derivative thereof comprises a C60 fullerene, said antibody comprising an amino acid heavy chain sequence (SEQ ID NO:2) and an amino acid light chain sequence (SEQ ID NO:4).

In an embodiment of the above-described antibody which is specific for a single-walled fullerene nanotube wherein the fullerene is selected from the group consisting of a fullerene or derivative thereof comprising from 20 to 540 carbon atoms, the antibody is a monoclonal antibody. In another embodiment of the above-described monoclonal antibody which is specific for a single-walled fullerene nanotube, the monoclconal antibody is a tip-specific antibody. In a further embodiment of the above-described monoclonal antibody which is specific for a single-walled fullerene nanotube, thIe antibody is a side-wall specific antibody. In yet another embodiment of the above-described monoclonal antibody which is specific for a single-walled fullererne nanotube, the fullerene carbon compound or derivative thereof comprises a C60 fullerene. In a further embodiment of the above-described monoclonal antibody which is specific for a single-walled fullerene nanotube, the fullerene carbon compound or derivative thereof comprises a C070 fullerene. In a still further embodiment of the above-described monoclonal antibody which is specific for a single-walled fullerene nanotube, the fullerene carbon compound or derivative thereof comprises a C76 fullerene. In another embodiment of the above-described monoclonal antibody which is specific for a single-walled fullereIne nanotube, the fullerene carbon compound or derivative thereof comprises a C78 fullerene. In yet another embodiment of the above-described monoclonal antibody which is specific for a single-walled fullerene nanotube, wherein the fullerene carbon compound or derivative thereof comprises a C84 fullerene. In a further embodiment of the above-described monoclonal antibody which is speclfic for a single-walled fullerene nanotube, the fullerene carbon compound or derivative thereof comprises a C70 fullerene. In still another embodiment of the above-described monoclonal antibody which is specific for a single-walled fullerene nanotube, the fullerene carbon compound or derivative thereof comprises a C240 fullerene.

This invention provides an antibody which is specific for a multi-walled fullerene nanotube, wherein the fullerene is selected from the croup consisting of a fullerene or derivative thereof comprising from 20 to 540 carbon atoms.

In an embodiment of the above-described antibody which is specific for a multi-walled fullerene nanotube wherein the fullerene is selected from the group consisting of a fullerene or derivative thereof comprising from 20 to 540 carbon atoms, the antibody is a monoclonal antibody. In another embodiment of the above-described monoclonal antibody which is specific for a multi-walled fullerene nanotube, the fullerene carbon compound or derivative thereof comprises a C60 fullerene. In a further embodiment of the above-described monoclonal antibody which is specific for a multi-walled fullerene nanotube, the fullerene carbon compound or derivative thereof comprises a C70 fullerene. In a still further embodiment of the above-described monoclonal antibody which is specific for a multil-walled fullerene nanotube, the fullerene carbon compound or derivative thereof comprises a C76 fullerene. In another embodiment of the above-described monoclonal antibody which is specific for a multi-walled fullerene nanotube, the fullerene carbon compound or derivative thereof comprises a C78 fullerene. In yet another embodiment of the above-described monoclonal antibody which is specific for a multi-walled fullerene nanotube, the fullerene carbon compound or derivative thereof comprises a C82 fullerene. In a further embodiment of the above-described monoclonal antibody which is specific for a multi-walled fullerene nanotube, the fullerene carbon compound or derivative thereof comprises a C84 fullerene. In yet another embodiment of the above-described monoclonal antibody which is specific for a multi-walled fullerene nanotube, the fullerene carbon compound or derivative thereof comprises a C240 fullerene.

This invention provides a monoclonal antibody which binds to a single-walled fullerene nanotube, wherein the fullerene is selected from the group consisting of a fullerene or derivative thereof comprising from 20 to 540 carbon atoms.

This invention provides a monoclonal antibody which binds to a multi-walled fullerene nanotube, wherein the fullerene is selected from the group consisting of a fullerene or derivative thereof comprising from 20 to 540 carbon atoms.

This invention provides isolated nucleic acid molecules which encode the monoclonal antibodies which are specific for a fullerene or derivative thereof, wherein the fullerene is selected from the group consisting of a fullerene carbon compound having from 20 to 540 carbon atoms.

This invention provides isolated nucleic acid sequences of the heavy (SEQ ID NO:1) and light chain sequences (SEQ ID NO:3) of the monoclonal antibody produced by the hybridoma produced by the fusion of a mouse antibody-producing cell and a mouse myeloma which is designated 1-10F-8A and deposited with the ATCC under Accession Number PTA-279, said hybridoma producing a monoclonal antibody which binds to fullerene C60. The encoded amino acids of the heavy chain sequenrce (SEQ ID NO:2) and light chain sequence (SEQ ID NO 4) of the monoclonal antibody produced by hybridoma 1-10F-8A are also provided by the invention.

This invention provides an isolated nucleic acid molecule which encodes the monoclonal antibody which is specific for a single-walled fullerene nanotube, wherein the fullerene is selected from the group consisting of a fullerene or derivative thereof comprising from 20 to 540 carbon atoms.

This invention provides an isolated nucleic acid molecule which encodes the monoLclonal antibody which is specific for a multi-walled fullerene nanotube, wherein the fullerene is selected from the group consisting of a fullerene or derivative thereof comprising from 20 to 540 carbon atoms.

In an embodiment the above-described isolated nucleic acid is DNA or RNA. In another embodiment the isolated nucleic acid is cDNA or genomic DNA. In a further embodiment the encoded antibody has substantially the same amino acid sequences of the heavy chain (SEQ ID NO:2) and light chain sequences (SEQ ID NO:4) as set forth in FIGS. 20 and 21. In a still further embodiment nucleic acid encodes a human antibody. In another embodiment the above-described isolated nucleic acid has nucleic acid sequences as set forth in FIGS. 20 and 21.

The DNA molecules of the subject invention also include DNA molecules coding or polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs wherein one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restrict Ion endonuclease enzymes; and the provision of additional initial, terminal or intermediate DNA sequences that facilitate construction of readily expressed vectors.

The DNA molecules described and claimed herein are useful for the information which they provide concerning the amino acid sequence of the monoclonal or polyclonal antibodies which are specific for fullerenes or derivatives thereof, wherein the fullerenes are selected from the group consisting of a fullerene carbon compound having from 20 to 540 carbon atoms, single-walled fullerene nanotubes, or multi-walled fullerene nanotubes and as products for the large scale synthesis of the polypeptides (the mcnoclonal or polyclonal antibodies which are specific for fullerenes or derivatives thereof or fragments thereof, single-walled fullerene nanotubes, or multi-walled fullerene nanotubes), or portions which are involved in protein-protein interactions by a variety of recombinant techniques. The molecule is useful for generating new cloning and expression vectors, transformed and transflected prokaryotic and eukaryotic host cells, and new and useful methods for cultured growth of such host cells capable of expression of the polypeptides (the monoclonal or polyclonal antibodies which are specific for fullerenes or derivatives thereof or fragments thereof, single-walled fullerene nanotubes, or multi-walled fullerene nanotubes) or portions thereof and related products.

This invention provides a vector comprising the isolated nucleic acid which encodes a monoclonal or polyclonal antibody which is specJific for fullerenes or derivatives thereof or fragments thereof, single-walled fullerene nanotubes, or multi-walled fullerene nanotubes. In an embodiment(s) the vector(s) further comprises a promoter of RNA transcription operatively linked to the nucleic acid. In another embodiment of the above-described vectors the promoter comprises a bacterial, yeast, insect or mammalian promoter. In an embodiment the vectors may further comprise a plasmid, cosmid, yeast artificial chromosome (YAC), bacteriophage or eukaryotic viral DNA.

This invention provides a host vector system for the production of a polype(ptide which comprises any of the above-described vectors in a suitable host. In an embodiment of the host vector system the suitable host is a prokaryotic or eukaryotic cell. In another embodiment of the host vector system the prokaryotic cell is a bacterial cell. In a further embodiment of the host vector system the eukaryotic cell is a yeast, insect, plant or mammalian cell.

Numerous vectors for e xpressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. TheIse additional elements may include splice signals, as will as enhancers and termination signals. For example, a bacterial expression vector includes a promoter such as the lac promoter and for transcription initiation the Shine-Dalgarno sequence and the start codon AUG. Similarly, a eukaryotic expression vector includes a heterlologous or homologous promoter for RNA polymerase II, a downstream polyadenylation signal, the start codon AUG, and a termination codon for detachment of the ribosome. Such vectors may be obtained commercially or assemblled from the sequences described by methods well known in the art, for example the methods described above for constructing vectors in general.

These vectors may be introduced into a suitable host cell to form a host vector system for producing the inventive proteins (monoclonal or polyclonal antibodies specific for fullerenes or derivatives thereof or fragments thereof, single-walled fullerene nanotubes, or multi-walled fullerene nanotubes). Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to, HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk⁻ cells and COS cells. Mammalian cells may be transfected by methods well known in the art such as calcium phosphate precipitation, electroporation and microinjection.

One of ordinary skill in the art will easily obtain unique sequences from the cDNA cloned in plasmids. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in plasmids may further be used to screen other human tissue cDNA libraries to obtain isoforms of the nucleic acid sequences encoding antibodies specific for fullerenes or derivatives thereof or fragments thereof, single-walled fullerene nanotubes, or multi-walled fullerene nanotubes, as well as, to screen human genomic DNA to obtain the analogous nucleic acid sequences. The homologous nucleic acid sequences and isoforms may be used to produce the proteins encoded thereby.

This invention provides a method for producing a polypeptide which comprises growing any of the above-described host vector systems comprising the isolated nucleic acid which encodes any of the above-described polypeptides, i.e. antibodies specific for fullerenes or derivatives thereof or fragments thereof, single-walled fullerene nanotubes, or multi-walled fullerene nanotubes under suitable conditions permitting production of the polypeptide(s) and recovering the polypeptide(s) so produced.

This invention provides a method of obtaining a polypeptide, i.e. an artibody specific for fullerenes or derivatives thereof or fragments thereof, single-walled fullerene nanotubes, or multi-walled fullerene nanotubes in purified form which comprises: (a) introducing the vector comprising the isolated nucleic acid which encodes the polypeptide (antibody) into a suitable host cell; (b) culturing the resulting cell so as to produce the polypeptide; (c) recovering the polypeptide produced in step (b); and (d) purifying the polypeptide so recovered.

This invention provides a purified polypeptide which is an antibody specific for fullerenes or derivatives thereof or fragments thereof, single-walled fullerene nanotubes, or multi-walled fullerene nanotubes, wherein the fullerenes are selected from the group consisting of a fullerene carbon compound having from 20 to 540 carbon atoms. In an embodiment the above-described purified polypeptide has the amino acid sequences for the heavy and light chain sequences as set forth in FIGS. 20 and 21, respectively.

This invention provides an oligonucleotide of at least 15 nucleotides capable of specifically hybridizing with a unique sequence of nucleotides present within a nucleic acid which encodes an antibody specific for fullerenes or derivatives thereof or fragments thereof, single-walled fullerene nanotubes, or multi-walled fullerene nanotubes, wherein the fullerenes are selected from the group consisting of a fullerene carbon compound having from 20 to 540 carbon atoms. In an embodiment of the oligonucleotide of at least 15 nucleotides capable of specifically hybridizing with a unique sequence of nucleotides present within a nucleic acid which encodes an antibody specific for fullerenes, single-walled fullerene nanotubes, or multi-walled fullerene nanotubes, the isolated nucleic acids which encode the antibody specific for fullerene s have the nucleic acid sequences for the heavy and light chain sequences as set forth in FIGS. 20 and 21, respectively. In further embodiments of any of the above-described oligonucleotides the nucleic acid may be DNA or RNA.

This invention provides a nucleic acid having a sequence complementary to the sequence of the isolated nucleic acid which encodes an antibody which is specific for a fullerene, a singlewalled fullerene nanotube, or a multi-walled fullerene nanotube, wherein the fullerene is selected from the group consisting of a fullerene or derivative thereof comprising from 20 to 540 carbon atoms, and wherein the antibody is a monoclonal antibody or a polyclonal antibody.

This invention provides a hybridoma produced by the fusion of a mouse alitibody-producing cell and a mouse myeloma, said hybridoma producing a monoclonal antibody which is specific for a fullerene.

This invention provides a hybridoma produced by the fusion of a mouse antibody-producing cell and a mouse myeloma which is designated 1-10F-8A and deposited with the ATCC under Accession Number PTA-279, said hybridoma producing a monoclonal antibody which binds to fullerene C60.

This invention provides a mouse monoclonal anti-fullerene-hybridoma produced by the fusion of a mouse antibody-producing cell and a mouse myeloma which is designated 1-10F-8A was deposited on Jun. 25, 1999 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure. Mouse monoclonal antifullerene-hybridoma 1-10F-8A was accorded ATCC Accession Number PTA-279.

This invention proviles a mouse monoclonal antibody specific for a fullerene-C60 and produced by the mouse monoclonal antibody-producing hybridoma designated 1-10F-8A and deposited with the ATCC under Accession Number PTA-279.

This invention provides an antibody which is specific for a fullerene or derivative thereof, wherein the fullerene is selected from the group consisting of a fullerene carbon compound having from 20 to 540 carbon atoms, wherein the antibody is a polyclonal antibody.

In an embodiment of the above-described polyclonal antibody which is specific for a multi-walled fullerene nanotube, the fullerene carbon compound or derivative thereof comprises a C60 fullerene. In another embodiment of the above-described polyclonal antibody which is specific for a multi-walled fullerene nanotube, the fullerene carbon compound or derivative thereof comprises a C70 fullerene. In yet another embodiment of the above-described polyclonal antibody which is specific for a multi-walled fullerene nanotube, the fullerene carbon compound or derivative thereof comprises a C76 fullerene. In a further embodiment of the above-described polyclonal antibody which is specific for a multi-walled fullerene nanotube, the fullerene carbon compound or derivative thereof comprises a C78 fullerene. In another embodiment of the above-described polyclonal antibody which is specific for a multi-walled fullerene nanotube, the fullerene carbon compound or derivative thereof comprises a C82 fullerene. In a further embodiment of the above-described polyclonal antibody which is specific for a multi-walled fullerene nanotube, the fullerene carbon compound or derivative thereof comprises a C84 fullerene. In a still further embodiment of the above-described polyclonal antibody whlich is specific for a multi-walled fullerene nanotube, the fullerene carbon compound or derivative thereof comprises a C240 fullerene.

This invention provides a polyclonal antibody which binds to a single-walled fullerene nanotube, wherein the fullerene is selected from the group consisting of a fullerene or derivative thereof comprising from 20 to 540 carbon atoms.

In an embodiment of the above-described polyclonal antibody which binds to a single-walled fullerene nanotube, wherein thle fullerene is selected from the group consisting of la fullerene or derivative thereof comprising from 20 to 540 carbon atoms, the polyclonal antibody is a tip-specific antibody. In another embodiment of the above-described polyclonal antibody, the antibody is a side-wall specific antibody. In a further embodiment of the above-described polyclonal antibody, the fullerene carbon compound or derivative thereof comprises a C60 fullerene. In a still further embodiment of the above-described polyclonal antibody, the fullerene carbon compound or derivative thereof comprises a C70 fullerene. In yet another embodiment of the above-described polyclonal antibody, the fullerene carbon compound or derivative thereof comprises a C76 fullerene. In another embodiment of the above-described polyclonal antibody, the fullerene carbon compound or derivative thereof comprises a C78 fullerene. In an embodiment of the above-described polyclonal antibody, the fullerene carbon compound or derivative thereof comprises a C82 fulleene. In yet another embodiment of the above-described plolyclonal antibody, the fullerene carbon compound or derivative thereof comprises a C84 fullerene. In a further embodiment of the above-described polyclonal antibody, the fullerene carbon compound or derivative thereof comprises a C240 fullerene.

This invention provides a polyclonal antibody which binds to a multi-walled fullerene nanotube, wherein the fullerene is selected from the group consisting of a fullerene or derivative thereof comprising from 20 to 540 carbon atoms.

In an embodiment of the above-described polyclonal antibody which binds to a multi-walled fullerene nanotube, wherein the fullerene is selected from the group consisting of a fullerene or derivative thereof comprising from 20 to 540 carbon atoms, the fullerene carbon compound or derivative thereof comprises a C60 fullerene.

In an embodiment of the above-described polyclonal antibody, the fullelene carbon compound or derivative thereof comprises a C70 fullerene. In another embodiment of the above-described polyclonal antibody, the fullerene carbon compound or derivative thereof comprises a C76 fullerene. In a further embodiment of the above-described polyclonal antibody, tlhe fullerene carbon compound or derivative thereof comprises a C78 fullerene. In yet another embodiment of the above-described polyclonal antibody, the fullerene carbon compound or derivative thereof comprises a C82 fullerene. In an embodiment of the above-described polyclonal antibody, the fullerene carbon compound or derivative thereof comprises a C84 fullerene. In another embodiment of the above-described polyclonal antibody, the fullerene carbon compound or derivative thereof comprises a C240 fullerene.

All of the above described antibodies may be produced in a sheep, hog, goat, rabbit, guinea pig, mouse, rat and a human subject.

Polyclonal antibodies may be produced by injecting a host animal such as rabbit, rat, goat, mouse or other animal with the immunogen of this invention, e.g. a fullerene-protein conjugate, wherein the protein may be but is not limited to thyroglobulin, RSA, or BSA. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: a Laboratory Manual,* (Cold Spring Harbor Laboratories, Cold Spring Harbor, N.Y.: 19883) the contents of which are hereby incorporated by reference.

The monoclonal antibodies may be produced by immunizing for example, mice with an immunogen. The mice are inoculated intraperitconeally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 10801 University Blvd., Manassas, Va. 20110-2209, USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the tern "antibody" includes chimeric antibodies and wholly s nthetic antibodies, and fragments thereof. "Detectable moieties" which function as detectable labels are well known to those of ordinary skill in the art and include, but are not limited to, a fluorescent label, a radioactive atom, a paramagnetic ion, biotin, a chemiluliminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides an antibody specific for a fullerene, wherein the fullerene is selected from the group consisting of a fullerene carbon compound or derivative thereof comprising from 20 to 540 carbon atoms, wherein a radioactive material is encapsulated in the fullerene.

Methods of encapsulating radioactive materials in fullerenes are known to one of skill in the art. For example Cagle, D. W. et al.(1999) PNAS (USA) 96:5182–5187 disclose the syntheIsis and use of radioactive metallofullerenes to monitor fullerene-based materials in vivo, wherein the radioactive material is holmium. One of skill in the art will recognize that radioactive materials other than hilolmium, e.g. gadolinium and other transition metals, ma y be encapsulated in fullerenes, including metallofullerenes.

This invention provides a method of determining a serum concentration of a fullerene in a subject which comprises: a) determining an amount of antibody which binds to the fullerene in the absence of serum; b) incubating a serum sample from a subject with an antibody which binds to the fullerene to form an antibody-fullerene complex; c) determining the amount of antibody which binds to the fullerene in the presence of serum by detecting the amount of fullerene complex; d) comparing the amount determined in step (c) with the amount determined in step (a), thereby determining the serum concentration of the fullerene in the subject.

In an embodiment of the above-described method of determining a serum concentration of a fullerene in a subject, the amount of antibody which binds to the fullerene in the absence of serum is determined for differing amounts of fullerene.

The determination of the amount of antibody which binds to the fullerene in the absence of serum fullerene allows one of skill in the art to prepare a standard curve for the amount of antibody which binds various known amounts of fullerene, so as to allow the comparison of the amount of antibody which binds to the fullerene in a serum sample. In another embodiment radioactive fullerene in differing known amounts may be used to determine the amount of antibody which bind thereto in the presence of "cold", i.e. nonradioactive fullerene, said amounts may be compared to the amount of antibody which binds to fullerene in a serum sample, thereby determining the amount of fullerene in the serum sample. For example the more nonradioactive fullerene (i.e. with larger amounts thereof) which binds to the antibody the lower the binding of the radioactive fullerene will be, allowing for the preparation of a standard curve with which to compare the presence of fullerene in a serum sample, which will bind in a manner similar to "cold" fullerene.

In an embodiment of the above-described method of determining a serum concentration of a fullerene in a subject, the detection of steps (a) and (c) is performed with a second antibody which binds to the antibody-fullerene complex, said second antibody being detectably labeled. In another embodiment of the above-described method of determining a serum concentration of a fullerene in a subject, the detectable label of the second antibody is selected from the group consisting of a radioactive isotope, enzyme, dye, biotin, a fluorescent label or a chemiluminescent label. In yet another embodiment of the above-described method of determining a serum concentration of a fullerene in a subject, the second antibody of step (c) is either a monoclonal antibody or a polyconal antibody. In a further embodiment of the above-described method of determining a serum concentration of a fullerene in a subject, the second antibody is detectably labeled. In a still further embodiment of the above-described method of determining a serum concentration of a fullerene in a subject, the detectable label of the second antibody is selected from the group consisting of a radioactive isotope, enzyme, dye, biotin, a fluorescent label or a chemiluminescent label.

This invention provides a method of purifying a fullerene from a sample which comprises: a) preparing an affinity chromatography column to which are bound antibodies which bind to the fulIlerene; b) adding a sample to the affinity chromatography column so as to allow the sample to flow through the column, thereby permitting the fullerene to bind to the antibodies, thereby forming a fullerene-antibody complex on the column; and c) separating the fullerenes from the antibody-fullerene complex of step (b) by altering the pH, thereby purifying the fullerene from the sample.

In an embodiment of the above-described method of purifying a fullerene from a sample, the pH is lowered to approximately pH 3.0. In another embodiment of the above-described method of purifying a fullerene from a sample, the pH is raised to between approximately pH 9.0–10.0.

This invention provides a method of preparing a nanoscale device which comprises manipulating a single-walled fullerene nanotube or nanotubes with the above-described antibody which is specific for a single-walled fullerene nanotube, wherein the fullerene is selected from the group consisting of a fullerene or derivative thereof comprising from 20 to 540 carbon atoms, to assemble electronic or chemical components of the nanoscale device.

This invention provides a method of preparing a nanoscale device which comprises manipulating a multi-walled fullerene nanotube or rIanotubes with the above-described antibody which is specific for a multi-walled fullerene nanotube, wherein the fullerene is selected from the group consisting of a fullerene or derivative thereof comprising from 20 tio 540 carbon atoms, to assemble electronic or chemical components of the nanoscale device.

In an embodiment of any of the above-described methods of preparing a nanoscale device which comprises manipulating a single-walled fullerene nanotube or nanotubes or of preparing a nanoscale device which comprises manipulating a multi-walled fullerene nanotube or nanotubes, the nanoscale device may be selected from the group consisting of a nancscale optics device, a nanoscale electronic device, and a nanoscale biosensor device.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

FIRST SERIES OF EXPERIMENTS

Materials and Methods

The fullerene derivatives 1-4 relevant to this invention are shown in FIG. 1. Compounds 1 and 3 were prepared as described in ref. 16. For the synthesis of 2, see ref. 17.

Preparation of the Bovilne Thyroglobulin (TG) Conjugate of 1. Compound 1 (1.5 mg, 1.6 $\mu$mol) was dissolved in 0.25 ml of dry pyridine. N-Hydroxysuccinimide (Sigma) (8 mg, 70 $\mu$mol) was added and brought into solution with the fullerene compound. Dilcyclohexylcarbodiimide (Fluka) (6 mg, 43 $\mu$mol) dissolved in 0.15 ml of dry pyridine was added, and the reaction was allowed to proceed at room temperature for 48 h. The reaction mixture then was added dropwise over a period of about 5 min to 10.4 mg (1.3 $\mu$mol) of TG dissolved in 1 ml of water and adjusted to pH 9.5. The pH was kept at 8.5 throughout the reaction by the addition of 1 M NaHCO$_3$. Some turbidity appeared during the reaction. The reaction was allowed to proceed for 4 h, and the reaction mixture then was dialyzed against PBS overnight at 4° C. The number of fullerene groups per molecule of TG was estimated, after clarification by centrifugation, to be ca. 20 by absorbance measurements at 320 nm (see below).

Bovine Serum Albumin (BSA) and Rabbit Serum Albumin (RSA) Conjugates. Similar procedures were used for the BSA and RSA conjugates. The UV-Vis spectrum of the RSA conjugate is shown in FIG. 2. It has a peak at 254 nm and a shoulder at about 320 nm. Others have seen these fullerene characteristics, albeit with slight shifts in wavelength (11, 16–19). The rise after 254 nm is characteristic of polypeptides, as shown by the spectrum of an equal concentration of RSA in FIG. 2. In both cases the proteins were substituted with about 10 molecules of the fullerene derivatives per molecule of protein, as determined by UV-Vis spectral analysis at 320 nm and by titration of the insubstituted amino groups by trinitrobenzenesulfonic acid (20).

Figure 3:
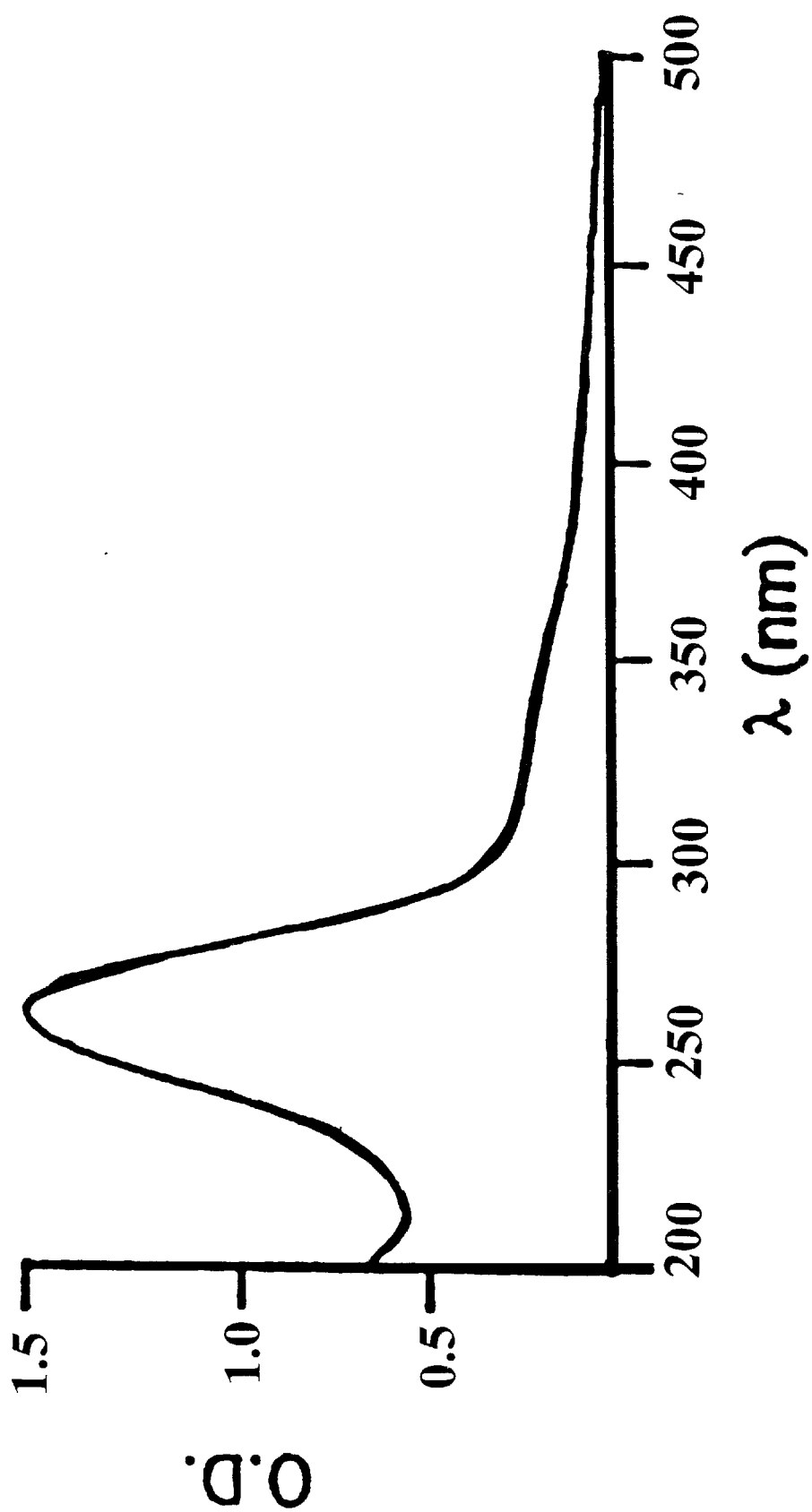
FIG. 3. UV-Vis spectrum of 1-trilysine in water (80 $\mu$g/ml)

Conjugation of 1 to Lys-Lys-Lys.3HCl (3L). N-Hydroxysuccinimide (0.5 mu, 4.3 μmol) was dissolved in 0.125 ml of dry pyridine. The solution was added to 0.5 mg (0.54 μmol) of 1, which then was allowed to dissolve. Dicyclohexlycarbodiimid (2.5 mg, 18 μmol) was dissolved in 0.1 ml of dry pyridine, and the solution was transferred to the solution containing 1 and N-hydroxysuccinimide. The total reaction mixture was allowed to stand at room temperature for 48 h. It then was added dropwise to 0.1 mg (0.2 μmol) of trilysine trihydrochloride (21) in 0.9 ml of 0.1 M NaHCO3, with stirring. The pH was kept at 8.5 by addition of the bicarbonate solution. The reaction was allowed to proceed for 4 h, and the resulting solution was taken to dryness over P$_2$O$_5$ in vacuo. The resulting residue was taken up in 250 μl of distilled water and clarified by centrifugation. Its UV-Vis spectrum is shown in FIG. 3. Like 1-RSA, it has a shoulder and a peak, albeit somewhat shifted. The shoulder is at 335 nm and the peak is at 260 nm. From both its spectrum and reaction of its free amino groups with trinitrobenzenesulfonic acid (20) it was found to have an aver age of 1.8 mol of 1 per trilysine molecule.

Conjugation of 1 to Penta-L-Lysine (Sigma). This reaction was carried out in a similar fashion as the trilysine conjugation. The final product was substituted to the extent of 2.7 mol of 1 per pentalysine.

Immunization Procedure and Detection of Antibodies. BALB/c mice were immunized i.p. with 1-TG in complete Freund's adjuvant for the primary immunization and incomplete adjuvant for subsequent immunizations.

After a total of three immunizations at 3-week intervals, confirmation of an immune response was determined by direct ELISA in which polystyrene plates (Corning) were coated with the 1-RSA conjugate (0.5 mg/ml in 0.1 M NaHCO$_3$, pH 9), and binding of preimmune and immune sera were determined by standard procedures. Development was with horseradish peroxidase-labeled goat anti-mouse IgG (Sigma), which tested negative for crossreaction with an IgM preparation. The substrate used was o-phenylenediamine.

Specificity of the resp)onse was determined by two procedures: double diffusion in agar (22) and competitive inhibition, as determined by ELISA using RSA and BSA conjugates of the fullerenes, as well as the oligo lysine derivatives. The fullerenes themselves were not soluble enough in aqueous solutions.

There were two controls for the ELISA experiments: (I) RSA, to show that the protein moiety did not participate in the inhibition, aiid (ii) adenosine-6-hexanoyl RSA (23), to show that the linkage group did not participate. The adenosine conjugate had been synthesized using the same strategy used for the fullerenes, i.e., linkage to the epsilon amino groups of the lysines via an N-hydroxysuccinimide ester derivative.

Results

Figure 4:
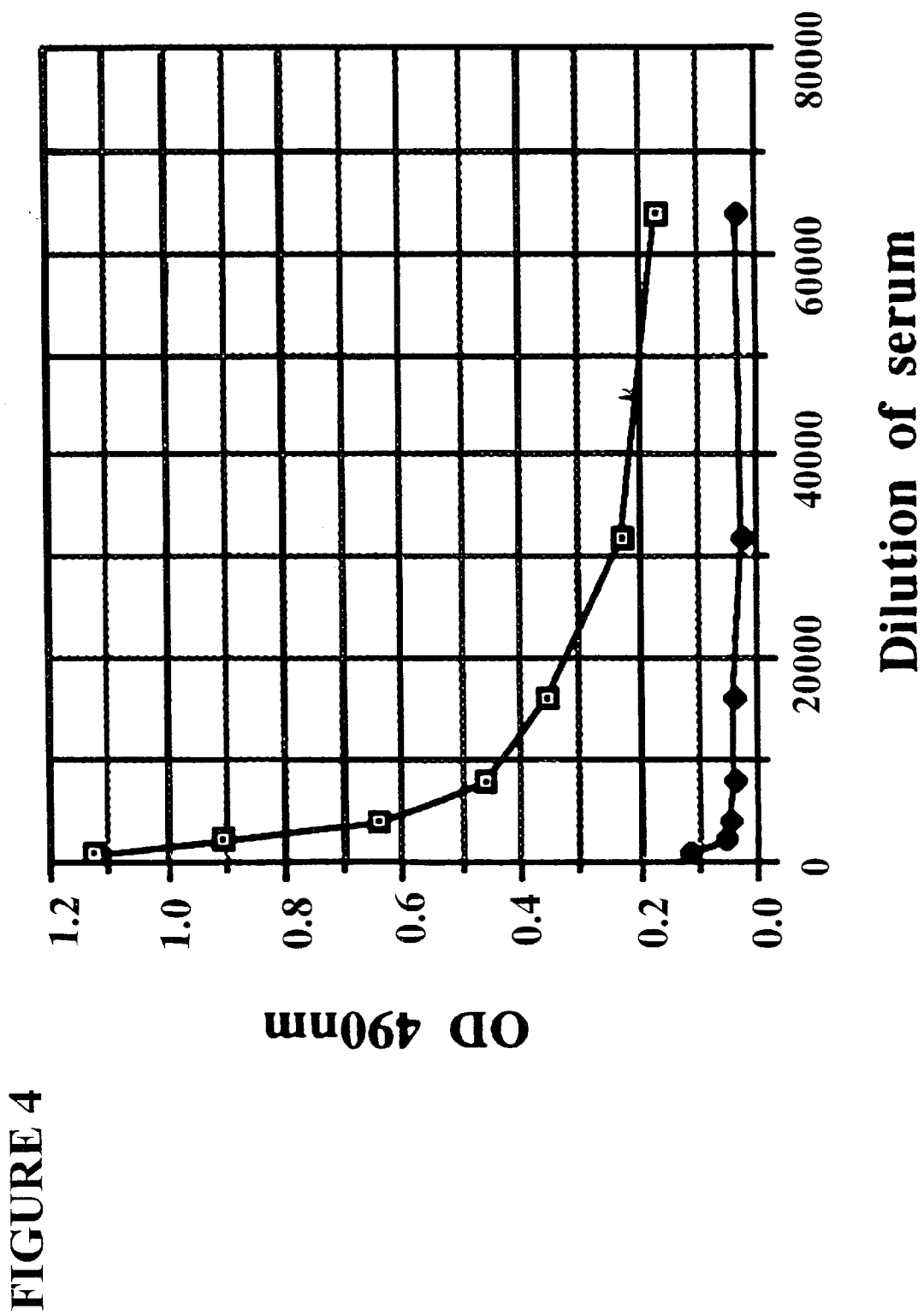
FIG. 4. ELISA study of antibody response to 1-RSA. White square, immune serum. Black diamond, preimmune serum.

Immune Response to 1-TG. The immune response of mice immunized with 1-TG first was determined by ELISA. Because of the extreme hydrophobicity of fullerenes, it was important to show that nonspecific binding to serum components did not occur in the preimmune serum. The results are shown in FIG. 4 for sera taken from a BALB/c mouse immunized i.p. with one primary and two booster injections 3 weeks apart. The result was a high titer of specific antibody, as measured with 1-RSA. No antibody or nonspecific binding was seen with components of the preimmune serum. Development was with a peroxidase-labeled anti-mouse antibody specific for mouse IgG.

Figure 5:
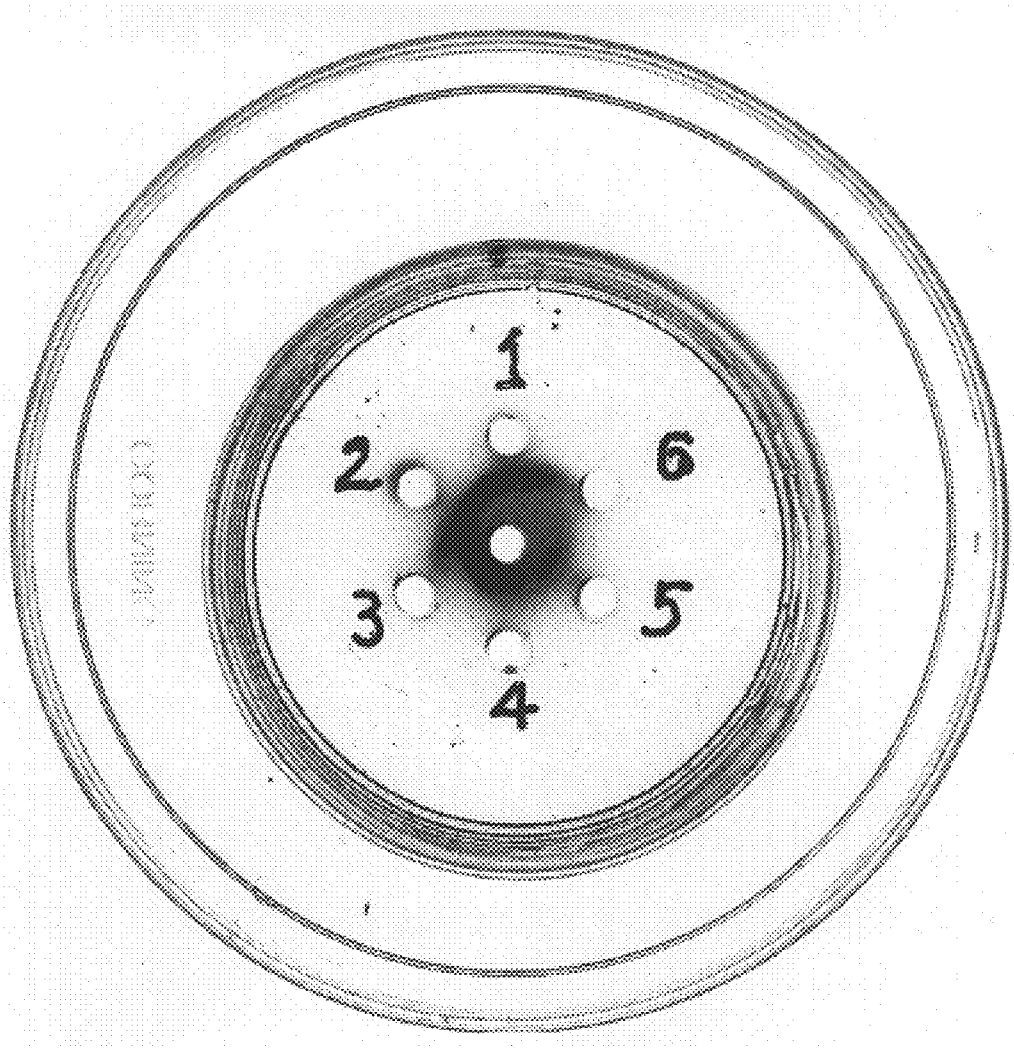
FIG. 5. Results of double diffusion in agar. Well 1, 1-TG (the immunogen); 2, 2-TG; 3, 1-BSA; 4, 1-RSA; 5, 3-RSA; and 6, TG.

Specificity of the Immune Response. Specificity of the immune response first las determined by double diffusion in agar. The results are shown in FIG. 5.

Confluent lines of precipitation were seen associated with wells 1–5 with a spur between wells 2 and 3, pointing toward 3, i.e., toward 1-BSA. This finding is evidence of a population of antibodies reactive with both 1 and 2, with an additional population specific for the carrier protein of the immunogen, 1-TG. The identity of precipitation with 1 and 2 is evidence for the lack of participation of the linker group, which is missing from 2. A visible, albeit smaller, precipitate was seen with 3-RSA (well 5), the $C_{70}$ fullerene. Well 6, containing unsubstituted TG, showed no visible precipitate. However, when the TG solution was diluted 5-fold, a line of precipitation was seen (not shown), indicating a low titer of antibody specific for unsubstituted TG, i.e., in the original experiment (FIG. 5), i.e. TG was in antigen excess. Anti-TG also cc)uld be detected by ELISA (below).

Figure 6:
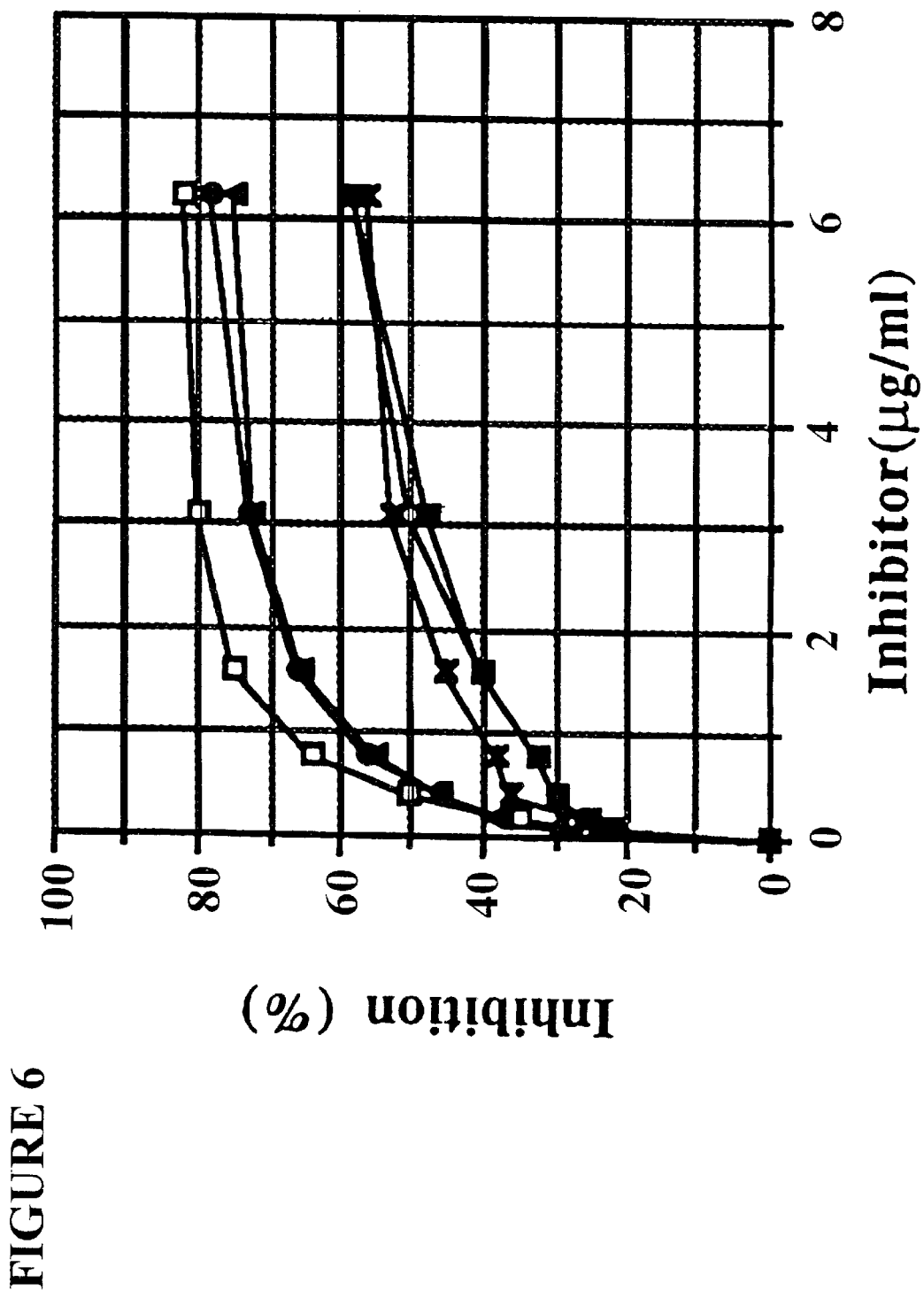
FIG. 6. ELISA inhibition experiments: Black triangle, 1-BSA; open circle, 1-(Lys)$_5$; black circle, 1-RSA; open square, 1-TG; black square, 3-(Lys)$_5$; x, 2-(Lys)$_5$.

Specificity also was determined by ELISA inhibition studies (FIG. 6). Binding to 1-RSA was inhibited by 1-RSA, 1-BSA, 1-TG, 3-pentalysine, 2-pentalysine, and 1-pentalysine. Inhibition by 2-pentalysine is additional evidence for nonparticipation of the linker group, i.e., specificity for the $C_{60}$ moiety. Although not shown in FIG. 6 no inhibition was seen by TG, RSA. or adenosyl-6-hexanoyl-RSA, which has the same linker joining the hapten to the protein carrier (23).

In an additional control for specificity, the fullerene derivatives 1-pentalysine, 1-RSA, and 1-BSA were tested by ELISA for nonspecific inhibition of an antibody to a retinoic acid derivative (unpublished work) with its hapten-RSA conjugate. No inhibition by the fullerene derivatives was seen, in contrast to the inhibition seen with the retinoic acic derivative (data not shown).

Taken together, the results show that there was an IgG response directed at the fullerenes, and not at the functional groups linking the fullerenes to the carriers. Moreover, a subpopulation of the antibodies raised to a $C_{60}$ fullerene crossreacted with the $C_{70}$ fullerene.

Discussion

Immunization of mice with a $C_{60}$ fullerene-TG conjugate produced a polyclonal response comprised of antibodies specific for $C_{60}$ fullerenes and a subpopulation that crossreacted with a $C_{70}$ fullerene derivative (FIGS. 5 and 6). Detection was possJible by ELISA using an IgG-specific second antibody showing that the antibodies raised were of the IgG isotype (FIGS. 4 and 6). It follows from this that derivatization of TG by a fullerene molecule did not prevent intracellular processing and subsequent peptide display to T cells presumably by the process of linked recognition (24). Oil interest is the manner of recognition of fullerenes by the immune system. Until we are in the position too examine the immune complex by direct means, e.g., x-ray crystallographic analysis, we can speculate based on characteristics of fullerenes that could provide potentiall for recognition.

Hydrophobicity. Fullerenes, being made up solely of carbon atoms, are very hydrophobic. It would be expected, therefore, that antibodies that recognize fullerenes will have hydrophobic amino acids in their binding sites. Such has been reported for the combining site of [an] a Fab' fragment of a mAb specific for progesterone (25, 26), a molecule highly apolar in character (see below). Contact with amino acids in the combining site of the heavy chain included three trypjtophans, one tyrosine, and a phenylalanine in a buried combining site of 254 $Å^2$ in surface area (26).

Curvature. Theoretical studies of various fullerenes show that curvature, expressed as the pyrimidalization angle P, significantly influences fullerene properties and reactivity (27). Although the completely flat graphite molecule has a P angle of 0°, the most curved fullerene, $C_{60}$ has angles uniformly bent at 11.6°. The angles of the $C_{70}$ molecule vary from P=8.8° to almost 12° (see FIG. 1 for its shape). Curvature of a normally planar aromatic ring induces local charge differences.

pi stacking. The pi system of fullerenes would be expected to interact with molecules in a combining site of an antibody via pi-stacking interactions. Experimental data from the x-ray structure of a $C_{60}$/benzene solvate clearly show this kind of interaction (28). Three benzenes are associated with each $C_{60}$ at distances of 3.27, 3.24, and 3.31 Å and are localized over the electron-rich interpentlagon bonds. The $C_{60}$ molecule is not rapidly "jumping" from one orientation to another as observed in the unsollvated $C_{60}$ by neutron diffraction structure (29).

Uneven charge distibution. Although the charge distribution of C60 is necessarily uniform, the charge distribution of a mono-substituted $C_{60}$ derivative such as 1 (FIG. 1) can show perturbations in its electron distribution (30). Moreover, it has been observed that $C_{60}$ and other fullerenes interact with donor —$NH_2$ and —SH groups (31, 32).

Combining site fit. We referred earlier to the interaction between progesterone and specific mAbs. The dimensions of $C_{60}$ and progesterone are very similar. Progesterone is longer and somewhat narrower (5.8 Å by 13 Å) (26); $C_{60}$ is a uniform sphere, 7.2 Å in diameter. The overall surface area, however, is very similar. There is no question about thle "fit" of a fullerene in the combining site of an antibody.

FIG. 7 (Upper) shows the x-ray structure of an Fab' fragment of a monoclonal progesterone-specific antibody bound to 5α-pregnane-20-one-3β-ol-hemisuccinate (26). The protein (Brookhaven PDB code 2DBL) is displayed as ribbons and the steroic as a space-filling model by using INSIGHT II (Molecular Simulations, San Diego, Calif.). The binding site is a large hydrophobic cavity lined with Trp, Phe, and Tyr groups. Using INSIGHT II, we replaced the steroid with $C_{60}$ to provide the model shown in FIG. 7 (Lower). As we did not relax the geometry using molecular dynamics, the fit is tight, but a slight side-chain adjustment would provile a very good fit.

Solvent displacement. The free energy released on removing a hydrophobic surface from contact with water has been shown to correlate well with binding constants (33). Molecular modeling, studies of 4 (FIG. 1), a competitive inhibitor of an HIV protease, removed 298 $Å^2$ of solvent exposure (33). This stabilization reaction was mainly caused by carbon-to-carbon contacts with hydrophobic residues at the enzyme's active site: Leu, Ile, Tyr, Trp, Pro, Gly, and Ala.

The question of the binding of $C_{60}$ and $C_{70}$ fullerenes to Fab' or Fv fragments of monoclonal antifullerene antibodies will be answered by x-ray crystallographic studies.

Finally, as part of tihis investigation three fullerene peptide derivatives halve been prepared that are highly water soluble and have presented the UV-Vis spectra of two of them.

REFERENCES FOR FIRST SERIES OF EXPERIMENTS

1. Kroto, H. W., Heath, J. R., O'Brien, S. C., Curt, R. F. & Smalley, R. E. (1985) *Nature* (London) 318, 162–163.
2. Kratschmer, W., Lamb, L. D., Fostiropoulos. K. & Huffman, D. R. (1990) *Nature* (London) 347, 354–357.
3. Scrivens, W. a., Bedworth. P. V. & Tour, J. M. (1992) *J. Am. Chem. Soc.* 114, 7917–7919.
4. Yu. G., Gao, J., Hummelin,.J. C., Wudl, F. & Heeger, a. J. (1995) *Science* 270, 1789–1791
5. Yacobson, B. I. & Smalley, R. E. (1997) *Amer. Sci.* 85, 324–337.
6. Jensen, a. W., Wilson, S. R. & Schuster, D. I. (1996) *Biorg. Med. Chem.* 4, 767–779.
7. Sijbesma, R., Srdanov, G.. Wudl. F., Castoro, J. a., Wilkins, C., Friedman, S. H., DeCamp, D. L. & Kenyon, G. L. (1993) *J. M. Chem. Soc.* 115, 6510–6512.
8. Schinazi, R. F., Sijbesma. R., Srdanov, G., Hill, C. L. & Wudl, F. (1993) *Antimicrob. Agents Chemother.* 37, 1707–1710.
9. Chiang, L. Y., Lu, J. T. & Lin, J. T. (1995) *J. Chem. Soc. Chem. Commun.*, 1283–1284.
10. Lu, L.-H., Lee, Y.-T., Chen, H.-W. Chiang, L. Y. & Huang, H. -C. (1998) *Brit. J. Pharmacol.* 123, 1097–1102.
11. Toniolo, C., Bianco, a., Maggini, M., Scorrano, G., Prato, M., Marastoni, M., Tomatis, R., Spisani, S., Palu, G. & Blair, E. D. (1994) *J. Med. Chem.* 37, 4558–4562.
12. Dugan, L. L., Turetsky, D. M., Du, C., Lobner, D., Wheeler, M., Almi, C. R., Shen. C. K.-F., Luh, T.-Y, Choi, D. & Lin, T.-S. (1997) *Proc. Natl. Acad. Sci. USA* 94, 9434–9439.
13. Jerne, N. K. (1974) *Ann. Inst. Pasteur/Immunol* 125, 373–389
14. Rajewsky, K., Forster, I. & Kumano, a. (1987) *Science* 238, 1088–1094
15. Langman. R. E. (1992) *Int. J. Clin. Lab. Res.* 22, 63–68.
16. Wang, Y., Cao, J., Schuster, D. I. & Wilson, S. R. (1995) *Tetrahedron Lett.* 36, 6843–6846.
17. Bensasson. R. V., Bienveue, F., Janot, J.-M., Leach, S., Seta, P., Zhaio, H., Schuster, D. I. & Wilson, S. R. (1995) *Chem. Phys. Lett.* 248, 566–570.
18. Anderson, T., Nilsson, K., Sundahl, M., Westman, G. & Wennerstrom, O. J. (1992) *J. Chem. Soc. Chem. Comm.*, 604–606.
19. Boulas, P., Kutne , W., Jones, M. T. & Kadish. K. M. (1994) *J. Phys. Chem.* 98, 1282–1287.
20. Snyder, S. L & Sobocinski, P. Z. (1975) *Anal. Biochem.* 64, 284–288.
21. Erlanger, B. F. & Brand, E. (1951) *J. Am. Chem. Soc.* 73, 4026–4027.
22. Johnstone, a. & Thlorpe, R. (1982) *Immunochemistry in Practice* (Blacklaell Scientific, Oxford), pp. 122–125.
23. Ku, H. H., Cleveland, W. L & Erlanger, B. F. (1987) *J. Immunol.* 139, 2376–2384.
24. Janeway, C. a., Jr. & Travers, P. (1996) *Immunobiology* (Garland, New York), pp. 8:3–8:5.

25. Erlanger, B. F., Borek, F., Beiser, S. M. & Lieberman, S. (1959) *J. Biol. Chem.* 234, 1090–1094.
26. Arevolo, J. H., Hassig, C. a., Stura, M. J., Taussig, M. J. & Wilson, I. a. (1994) *J. Mol. Biol.* 241, 663–690.
27. Haddon, R. C. (1993) Science 261, 1545–1550.
28. Meidine, M. F., Hitchcock, P. B., Kroto, H. W., Taylor. R. & Walton, D. R. M. (1992) *J. Chem. Soc. Chem. Comm.,* 1534–1537.
29. David, W. I. F., Ebberson, R. M., Mattewman, J. C., Prassides, K., Deiinis, T. J. S., Hare, J. P., Kroto, H. W., Taylor, R. & Walton. D. R. M. (1991) *Nature* (London) 353, 147–149.
30. Hirsch, a., Lamparth, I. & Grosser, T. (1994) *J. Am. Chem. Soc.* 116,9385–9386.
31. Skiebe, a., Hirsch, a., Klos. H. & Gotschy. B. (1994) *Chem. Phys. Lett.* 220, 138–140.
32. Subramanian, R., Boulas, P., Vijayshee, M. N., D'Souzaj. F. & Jones, M. D. (1994) *J. Chem. Soc. Chem. Commun.,* 1847–1848.
33 Friedman, S. H., DeCamp, D. L.. Sijbesma, R. P., Srdanov. G., Wudl, F. & Kenyon, G. L. (1993) *J. Am. Chem. Soc.* 115, 6506–6509.

SECOND SERIES OF EXPERIMENTS

The conjugate, $C_{60}$-thyroglobulin, is prepared as described below in "Preparation of Polyclonal Antibodies Specific for Fullerenes". In those studies, polyclonal IgG antibodies were elicited in mice. A major population showed specificity for the $C_{60}$ hapten; a subpopulation reacted with $C_{70}$. Therefore, hybridomas that produce monoclonal antibodies specific for $C_{60}$ fullerenes and others specific for $C_{70}$ fullerenes may be isolated. On the other hand, it is not clear that the reaction with $C_{70}$ was not just a cross-reIaction, i.e. a population of anti-$C_{60}$ antibodies that cross-reacted with $C_{70}$. This possibility is taken into account during the screening process.

Alternatively, antibodies specific for $C_{70}$ fullerenes may be obtained by immunizing with a $C_{70}$-thyroglobulin conjugate. Here, too, however, the possibility of $C_{60}$ and $C_{70}$ cross-specificity exists. One interest, in this case, is to obtain $C_{70}$ specificity. Screening for specificity is by ELISA using RSA conjugates of the $C_{60}$ and $C_{70}$ fullerene derivatives shown in FIG. 1 of the first series of experiments.

Immunization of BALB/c mice is according to the protocol used to obtain the polyclonal anti-fullerene antibodies (see above), with thyroglobulin as the carrier protein, i.e. 1-TG (see FIG. 1, first series of experiments, for structure of 1). Primary immunization is by subcutaneous injection in Freund's complete adjuvant, followed three weeks later by a booster injection in incomplete Freund's adjuvant. Usually two additional booster injections, two weeks apart, are sufficient to raise a sufficiently high titer of specific antibody (assayed against the 1-RSA by ELISA) to start the hybridoma protocol.

The mouse is sacrificed, its spleen removed and spleen cells fused with a nc)n-producer mouse myeloma, P3x63-Ag8.613, using PEG 1000 according to the procedure of Sharon et al (1). The cells are placed in 96 well plates and, after two weeks incubation at 37° C., the supernatants are assayed by ELISA for binding to 1-RSA. Cells in positive wells are subdloned twice by limiting dilution and positive clones are isolated and grown in 96 well plates, then 24 well and finally in flasks, being assayed along the way.

Specificities for $C_{60}$ fullerenes and cross reactions with $C_{70}$ fullerenes are determined by ELISA. The specific aim is to isolate antibodies to $C_{60}$ that do not cross react with $C_{70}$ compounds. Immunization may also be performed with $C_{70}$-TG and selection for monoclonal antibodies with $C_{70}$ specificity may be accomplished.

The possibility of covalent linkage between fullerenes and a specific monoclonal antibody (above) is raised and can be tested for that in a preliminary way as follows:

Incubate aliquots of monoclonal antibody with fullerene-trilysine for periods oIf 2h–24h. After dialysis against PBS for 24 h to remove unbound fullerene, the aliquots are assayed for binding to fullerene-RSA by ELISA. Covalent linkage would be indicated by a decrease in binding with time of incubation with fullerene-trilysine. The control will be antibody incubated for the same periods of time, but in the absence of fullerene-trilysine. Of course, unambiguous evidence of covalent linkage will be provided by the proposed x-ray crystallographic studies.

Preparation of Fab' and Fv Fragments of Monoclonal Antibodies a) Fab' Fragments

The specific monoclonal antibody is converted into a Fab' fragment after purification on a DEAE-cellulose column in phosphate buffer, pH 8.0. The IgG antibody leaves the column at the void volume. This is followed by digestion with papain in the presence of mercaptoethanol at 37° C. (enzyme: substrate=1:100). The course of digestion is followed by SDS-gel electro-phoresis. The Fab fraction is then purified on a DEAE-cellulose column, precipitated with $(NH_4)_2SO_4$, and dialyzed against 0.01M potassium phosphate, pH 7.0. This is essentially the procedure used by Mariuzza et al. (2) for the preparation of Fab from a monoclonal anti-lysozyme antibody. The Fab was used in X-ray crystallographic studies. The Fab purification may also be done by carboxymethyl cellulose column (Porter, 1951, Biochem. J.)

b) Fv Fragments

Fv fragments are most suitably produced by molecular biological procedures as a recombinant protein. The variable chains that make up the Fv fragment can best be prepared by PCR cloning with the appropriate primers and expression either in bazcteria (*E. coli*) or in eukaryotic cells. Enzyme digestion (e.g. pepsin) has been found to be less reliable.

With respect to expression in *E. coli,* one of skill may use the procedure of Orlandie et al. (3). In this procedure, RNA is isolated from about $10^6$ hybridomas using guanidinium isothiocyanate. This is followed by reverse transcription of total mRNA using an oligo(dT) primer and then amplification of the resulting cDNA by PCR, using degenerate oligonucleotides based on conserved regions at the 5' end of V gene segments and the 3' end of the J segments. This is then followed by cloning of the amplified $V_H$ and $V_L$ genes in the pUC19-based dicistronic vector pSW1. It is in frame with the signal sequence of pectate lyase to allow secretion into the endoplasmic space of *E. coli.* sequencing of several clones is necessary to ensure that random mutations have not occurred. This procedure was used by Goldbaum et al. to prepare Fv fragments for preliminary x-ray analysis of Fv-Fv complex (4, and see below).

One of skill may also use the cloning procedure developed by Coloma et al. (5, 6). This procedure allows for expression in non-producer myeloma cell lines such as NS2 or P3X63-Ag8.653. Most of applicants' hybridoma experience is with the latter line and therefore, this procedure is preferred for expression of the Fv fragments.

The Fullerene Derivativle Co-crystallized with the Fab and Fv Fragments of the Antibody The synthesis of a trilysine derivative of the $C_{60}$ fullerene compound 1 has already been described (see below). This derivative is, however, a mixture with an average substitute of 11.8 fullerenes per trilysine. For the co-crystallization experiments, the monosubstituted derivative is preferred. The separation of the pure monosubstituted compound from the mixture can be accomplished by reverse phase or ion exchange chromatography because the various components of the mixture differ in hydrophobicity and charge.

Preparation of Polyclonal Antibodies Specific for Fullerenes

The fullerene derivatives 1-4 used in the studies relevant to this invention are shown in FIG. 1.

Compounds 1–3 were prepared as described in ref. 16, first series of experiments. For the synthesis of 2, see ref. 17, first series c)f experiments.

Preparation of the Bovine Thyroglobulin (TG) Conjugate of 1

The conjugate was made according to the procedure set forth in the "First Series of Experiments". The number of fullerene groups per molecule of TG was estimated after clarification by centrifugation to be ca. 20 by absorbance measurements at 320 nm (see below).

Bovine Serum Albumin (BSA) and Rabbit Serum Albumin (RSA) Conjugates

The conjugates were made according to the procedure set forth in the "First Series of Experiments".

Conjugation of 1 to Lys-Lys-Lys.3HCl (3L). N-Hydroxysuccinimide (0.5 mg; 4.3 μmoles) was dissolved in 0.125 ml of dry pyridine. The solution was added to 0.5 mg (0.54 μmoles) of 1, which was then allowed to dissolve. Dicyclhexlycarbomiimide (2.5 mg); 18 μmoles) was dissolved in 0.1 ml of dry pyridine and the solution transferred to the solution containing 1 and N-hydroxysuccinimide. The total reaction mixture was allowed to stand at room temperature for 48 h. It was then added dropwise to 0.1 mg (0.2 μmoles) of trilysine trihydrochloride (21, first series of experiments) in 0.9 ml of 0.1 N $NaHCO_3$, with stirring. The pH was kept at 8.5 by addition of the bicarbonate solution. The reaction was allowed to proceed for 4 h, and the resulting solution taken to dryness over $P_2O_5$ in vacuo. The resulting residue was taken up in 250 ul distilled water and clarified by centrifugation. Its uv-vis spectrum is shown in FIG. 3, first series of experiments. Like 1-RSA, it has a shoulder and a peak, albeit somewhat shifted: The shoulder is at 335 nm and the peak is at 260 nm. From both its spectrum and reaction of its free amino groups with trinitrobenzenesulfonic acid (20, first series of experiments) it was found to have an average of 1.8 molecules of 1 per trilysine molecule.

Conjugation of 1 to Penta-L-lysine (Sigma, St. Louis, Mo)

This reaction was carried out in a similar fashion as the trilysine conjugation. The final product was substituted to the extent of 2.7 molecules of 1 per pentalysine.

Immunization Procedure and Detection of Antibodies

Balb/C mice were immunized i.p. with 1-TG in complete Freund's adjuvant for the primary immunization and incomplete adjuvant for subsequent immunizations.

After a total of 3 immunizations at 3 week intervals, confirmation of an immune response was determined by direct ELISA in which polystyrene plates (Corning) were coated with 1-RSA conjugate (0.5 mg/ml in 0.1 N $NaHCO_3$, pH 9) and binding of preimmune and immune sera determined by standard procedures. Development was with horseradish peroxide-labeled goat anti-mouse IgG (Sigma, St. Louis, Mo.) which tested negative for cross reaction with an IgM preparation. The substrate used was o-phenylenediamine.

Specificity of the response was determined by two procedures: Double diffusion in agar and competitive inhibition, as determined by ELISA using RSA and BSA conjugates of the fullerenes, as well as the oligo lysine derivatives. The fullerenes themselves were not soluble enough in aqueous solutions.

There were two controls for the ELISA experiments: 1) RSA, to show that the protein moiety did not participate in the inhibition; and 2) adenosine-6-hexanoyl RSA (23, first series of experiments), to show that the linkage group did not participate. The adenosine conjugate had been synthesized using the same strategy used for the fullerenes, i.e., linkage to the epsilon amino groups of the lysines via an N-hydroxysuccinimide ester derivative.

Results

The Immune Response to 1-TG. The immune response of mice immunized with 1-TG was first determined by ELISA. Because of the extreme hydrophobicity of fullerenes, it was important to show that non-specific binding to serum components did not occur in the pre-immune serum. The results are shown in FIG. 4 (first series of experiments) for sera taken from a Balb/C mouse immunized i.p. with one primary and two booster injections three weeks apart. The result was a high titer of specific antibody, as measured with 1-RSA. No antibody or non-specific binding was seen with components of the pre-immune serum. Development was with a peroxidase-labeled anti-mouse antibody specific for mouse IgG.

Specificity of the Immune Response. Specificity of the immune response was first determined by double diffusion in agar. The results Mare shown in FIG. 5 (first series of experiments). Lines of precipitation were seen associated with wells 1–5 with a spur between wells 2 and 3, pointing toward 3, i.e. toward 1-BSA. This implies an additional reactive epitope in 1-TG, not present in the BSA conjugate. A visible, albeit small precipitate was seen with 3-RSA (well 5). Well 6, containing unsubstituted TG showed no visible precipitate. However, when the TG solution was diluted five-fold, a line of precipitation was seen (not shown), indicating a low titer of antibody specific for unsubstituted TG, i.e. in the original experiment (FIG. 5, first series of experiments) TG was in antigen excess. Moreover, anti-TG could be detected by ELISA (below).

Specificity was also determined by ELISA inhibition studies (FIG. 6, first series of experiments). Binding to 1-RSA was inhibited by 1-RSA, 1-BSA, 1-TG, 3-pentalysine and 1-pentalysine. No inhibition was seen by TG, RSA, or adenosyl-6-hexanoyl-RSA, which has the same linker joining the hapten to the protein carrier (23, first series of experiments). As an additional control for specificity, 1-RSA, 1-pentalysine and 1-BSA were tested by ELISA as non-specific inhibitors of an antibody to retinoic acid (unpublished). No inhibition was seen, in contrast to inhibition by retinoic acid.

REFERENCES FOR SECOND SERIES OF EXPERIMENTS

1. Sharon, J. M. et al., (1983) Proc. Natl. Acad. Sci. USA, 76:1420–1424.
2. Mariuzza, R. A. et al. (1983) J. Mol. Biol. 170:1055–1058.
3. Orlandi, R. et al. (1989) Proc. Natl. Acad. Sci. USA, 86:3833–3837.38.
4. Goldbaum, F. A., et al. (1994) J. Mol. Biol., 241:739–743.
5. Leu, J.-G., et al. (1994) Proc. Natl. Acad. Sci. USA, 91:10690–10694.
6. Coloma, M. J., et al. (1992) J. Immunol. Meth. 152:89–104.
7. Jerne, N. K. et al., (1974) Ann. Immunol. (Inst. Pasteur) 125C:373–389.

8. Cleveland, W. L., et al. (1993) Nature 205:56–57.
9. Erlanger, B. F., et al. (1991) Biochem. Soc. Transactions., 19;138–143.
10. Braden, B. C., et al. (1996) J. Mol. Biol. 264:137–151.
11. Braden, B. C., et al. (1998) The Immunologist, 6:13–18.

Third Series of Experiments

The objective of these studies is to prepare and screen antibodies to carbon clusters and nanotubes: fullerene compounds C60, C70, C240 and [10, 10]-nanotubes. It is expected that C240-specific monoclonal antibodies (MAB's) can be used to recognize the tips and/or side walls of single wall nanotubes (SWNT's). The interactions of carbon clusters and nanotubes with these biomolecules by a variety of means, including protein X-ray crystallography are to be characterized. MAB's to SWNT's may be used to develop assays that will accelerate SWNT processing, applica-tions, and commercialization. Finally, basic science issues involving the future use of antibodies as assemblers are explored that will allow programmed assembly of nanotubes at the nanometer and mesoscopic scale.

Carbon clusters and nanotubes: The discovery of a new form of carbon fullerene-C60 in 1985 by Smalley and coworkers at Rice University stimulated tremendous worldwide research interest [1]. When the Huffman-Kratschner (HK) arc process for production of fullerene-C60 in quantity made sample s of C60 available in 1991, scientists throughout the world began to explore C60 chemistry. Close relatives of C60, fullerene nanotubes (very long graphitic molecular fibers), were first observed in the HK arc process by Iijima [2]. Numerous theoretical and microscopic studies of nanotubes followed this exciting discovery [3]. However, it was the recent breakthrough by Smalley—preparation of gram quantities of fullerene single wall nanotubes (SWNT)—that promises to propel SWNT research to commercial application. SWNT's are called "the perfect carbon fibers." They conduct electricity as well as gold, and are 100× stronger than steel at 1/6 the density. Important DoD-related related applications include mechanical/chemical applications as well as optical/electronic applications. Possible uses are lightweight, high strength composites for vehicle body panels, ship hulls and airframes, ship and helicopter propellers, rocket nozzles, helmets and body armor. Electronic/optical applications could include tactical displays, laser eye protection, vacuum electronics, capacitors, batteries and fuel cells. Other uses may include chemical filters, catalyst supports, hydrogen storage and nanoscale devices for computation [.] [4].

The enormous promise of SWNT's requires the development of many supporting basic science areas to assist in characterization and to begin evaluation of potential biological applications and potential health risks. Considerable work is known about C60 chemistry and much work has been done on toxicology and even drug development with fullerenes [5]. The toxicology of large carbon fibers has been extensively studied and a review is available [6]. Nothing at all is known about toxicology of SWNT's, or their interactions with biological systems. While no general toxic effects of fullerenes are known, the small diameter and very large aspect ratio (ratio of length to diameter) somewhat reminiscent of asbestos fiber, make an important side-benefit of this research the beginning first steps to the understanding of the relationship of SWNT's to human health.

Antibodies: while there is not enough space here to even begin to review the field of immunology, it can be simply pointed out that cells of the immune system can produce such antibodies in response to foreign molecules called antigens. Antibodies are protein molecules of molecular weight ~150,000 and are created by antibody-producing cells to bind strongly to an antigenic foreign molecule. Antibodies produced directly by animal immunization are polyclonal since they are produced by a multiplicity of cells that respond to the presence of the antigen. Techniques are also available for the preparation of monoclonal antibodies (MAB). MAB's are prepared from a single cloned cell line and thus only one pure molecular form of the antibody is obtained. MAB's are desirable since they are pure molecules, can be crystallized, and molecular biological techniques be used to sequence the gene of the MAB, study, characterize, model, and modify the structure, and prepare crystals for X-ray crystallography.

The development of methods for the preparation of antibodies to hydrophobic small molecules is well known to one of skill in the art [7]. During the 1950's and 60's Erlanger developed the approach of linking steroid molecules to serum albumins, to immunize rabbits with the steroid-serum albumin conjugate, and to thereby obtain specific anti-steroid antibodies. This method has revolutionized detection of hydrophobic compounds in biological systems. In his latest work, Erlanger has prepared monoclonal antibodies to the hydrophobic molecule taxol as well as a MAB that mimics taxol [8].

Figure 23:

Approach and Preliminary studies: Carbon cluster and nanotube antibodies are to be prepared and MAB to selected fullerenes have been crystallized. It is possible to produce X-ray quality crystals and to determine the complete 3D structure of these antibodies (see, for example, FIG. 23 which shows the 3D structure of the active site of an anti-fullerene monoclonal antibody). Antibodies to SWNT's can be imagined to consist of two classes: tip-specific antibodies and side-wall specific antibodies. Tip-specific antibodies are prepared using antibodies produced using a related fullerene hapten. The tips of [10,10]-SWNT's are predicted to be hemi-fullerenes, specifically one half of a C240 molecule. Although C240 has been detected by mass spectrometry and STM, it has not yet been isolated [8,9]. Vigorous work in that area is continuing. Currently only C60, C70, C76, C78, and C84 are available in commercial quantities.

Figure 8:
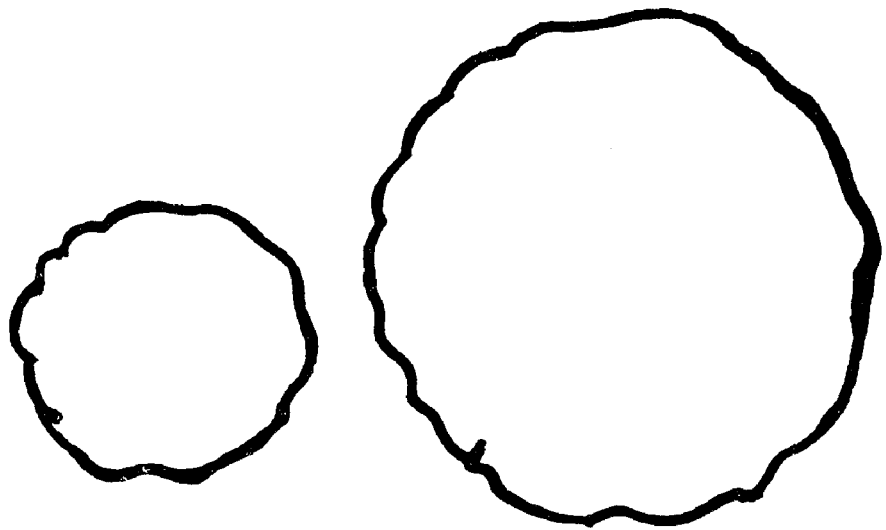
FIG. 8 Computer models of fullerenes C$_{60}$ (7.2 A) and C$_{240}$ (~14 A). C$_{240}$ is the structure of the endcap of a [10,10] single wall nanotube.

While C240 is much larger that C60 (see FIG. 8) it is well within the molecular scale of known antibody combining sites. An antibody to dextran binds 5 glucose residues which corresponds to a combining sites 2.5 nm long. (The taxol anti-idiotypic antibody shown in FIG. 2 and discussed later binds to tubes 25 nm in diameter)[8].

Considerable chemistry is now known about C60, and so the first experiments used this simplest fullerene. Preliminary studies are very encouraging and indicate that excellent polyclonal antibodies can be prepared by essentially conventional methods. Fullerene C60 was treated as a hapten and covalently linked to bovine serum albumin (BSA) and rabbit serum albumin (RSA) in order to induce a T-dependent immune response which can lead to high affinity antibodies. Linkage to BSA and RSA was performed via an N-hydroxysuccinimide ester derivative of C60. A rabbit was immunized with BSA-fullerene conjugate dissolved in aqueous solution and emulsified with Freunds adjuvant. This mixture was injected intradermally in multiple regions of the back of a rabbit. This initial immunization was followed by three booster immunizations. Serum drawn from the rabbit was tested for fullerene-specific antibodies using the RSA conjugate of fullerene-C60. This was done because the rabbit does not make antibodies to its own protein, RSA. Hence any reaction will be directed at the fullerene-C60 moiety. The antibodies were detected using an ELISA technique [s]. Recognition of the water soluble anti-viral fullerene derivative, originally synthesized by Wudl, by the C60 specific antibodies has been demonstrated.

The goal of these studies is to develop methods to prepare high-affinity monoclonal antibodies to fullerene clusters and carbon nanotubes and to characterize their interactions by a variety of means including X-ray crystallography. This work explores the application of antibodies to manipulation of nanotubes.

The long range goal of this program is to design an antibody-based nanotube analysis system and create a nanoassembler system that could assist in the organization of SWNT's into useful nanoscale devices. Fullerene antibodies serve as the basis for an important enabling science— connecting the "dry-side" of nanotechnology with the "wet-side", i.e. biology. Initially prepared and characterized are the antibodies to fullerene-C60 and to SWNT's. This enables one to learn more about how best to link, solubilize, and characterize antibodies to carbon clusters and SWNT's and to develop new methods to solve fundamental problems in analysis of SWNT structures, for example, to distinguish between [10,10] tubes and [n,m] tubes using specific antibodies.

Technology to use monoclonal antibodies (MAB) to allow assembly and organization of carbon clusters and SWNT's into large mesoscopic arrays producing useful devices are also encompassed within the scope of the present invention. This use is widely promoted in nanotechnology, and may be possible by harnessing monoclonal antibody technology to do it. A good demonstration has already ben accomplished. Cell division (mitosis) is mediated by a complex tubulin by the mediation of a small hydrophobic molecule called Taxol. Erlanger has shown this process can also be carried out by an anti-idiotypic antibody which mimics the action of taxol and stimulates the process of micro-tubule organization as shown in FIG. 2. It is suggested that tip-specific and side-wall specific SWNT MAB's of various sorts may be developed as "nano-assemblers" for the arrangement of SWNT-based devices. It may be possible to reconstitute catalytic MAB's that operate in organic media to promote the assembly and orientation of SWNT's into useful nanoscale devices on the surface of silicon chips [11].

Figure 9:
FIG. 9 An electro microgram of micro-tubules with y-shaped MAB' bound to them along the side-walls. These fibers are grown in-situ in response to the axol-like MAB factors. The dimensions of micro-tubules are on the order of 25 nm, similar to multi-wall carbon nanotubes, although larger than single-wall nanotubes (SWNT).

FIG. 9 shows an electro-microgram of micro-tubules with y-shaped MAB's bound to them along the side-walls. Theses fibers are grown in-situ in response to the taxol-like MAB factors. The dimensions of micro-tubules are on the order of 25 nm, similar to multiwall carbon nanotubes, although larger that SWNT.

REFERENCES FOR THIRD SERIES OF EXPERIMENTS

1. "Buckminsterfullerene," Billips, W. E.; Clufolini, M. A., Eds, VCH, NY (1992).
2. "Single-shell carbon nanotubes of 1-nm in diameter," Iijima, E.; Ichihashi, T. Nature 361, 603 (1993).
3. "Carbon Nanotubes," Ann. Rev Material Sci., 243, 235 (1994).
4. "Fullerene Nanotubes: C1,000,000 and Beyond," Yokabsen, B. I.; Smalley, R. E. American Scientist, 85, 324 (1997).
5. "Biological Applications of Fullerenes-A Review," Jenson, A.; Wilson, S. R.; Schuster, D. I.; Bioorganic and Medicinal Chermistry, 4, 767, (1996).
6. "Toxicology of Carbon Fibers," Thomson, S. A. Appl. Ind. Hyg. 29, (1989).
7. "Preparation of Antigenic Hapten-Carrier Conjugates," Erlanger, B. F. Methods in Enzymology, 70, 85 (1980).
8. "Idiotypic mimicry and the assembly of a supramolecular structure; and anti-idiotypic antibody that mimics taxol in its tubulin-microtubule interactions," Leu, J-G; Chen, B-X; Diamanduras, A. W.; Erlanger, B. Proc. Natl. Acad. Sci. USA, 91, 10690 (1994).
9. "Mass spectrometry and STM Imaging of Giant Fullerenes," Lamb, L. D. et. al. Science 255, 1413 (1992).
10. "C240-the least reactive Fullerene," Haddon, R. C.; Scusaria, G. E.; Smalley, R. E. Science, in press.
11. "Enzymic Catalysis in Anhydrous Organic Solvents," Klibanov, A. M. Trends Biochem Sci, 14, 145 (1989).

Fourth Series of Experiments

Radioimmunotherapy (RIT) has the potential to deliver doses of highly energetic radiation specifically to cancerous growths, thereby eliminating the radioactive damage to healthy tissue common during externally delivered radiation therapy. The traditional method for RIT is to link a radioactive atom to a monoclonal antibody (mAb) specific for the tumor, and inject it into the patient. The mAb then circulates until it binds to the tumor, where the radionuclide decays, emitting radiation to destroy the cancer cells. To date, the radioactive metal atoms have been bound to a chelating molecule, which is in turn linked to the mAb specific to the epitope on the tumor. Similar methods have been developed for radioimmunoimaging (RII), where a gamma ray emitter is bound to the chelating compound, and scintography is used to detect the concentrated areas of gamma rays which mark the tumor.

Unfortunately, in the methods developed to date, almost none of the administered radioactive dose reaches the cancer. As a result, clinical trials have shown poor response rates to RIT against solid malignancies (Wilder et al., 1996). In conventional methods, the primary problem is the long time required for the mAb to find the cancer cells. While the mAbs circulate, a significant fraction of the radionuclides decay, damaging healthy tissue and resulting in low tumor/ nontumor (T:NT) ratios of radioactivity. Further, the linker can be metabolized, separating it from the mAb, and/or the metal can become unchelated, both of which release radionuclides that will never reach the tumor.

Figure 10:
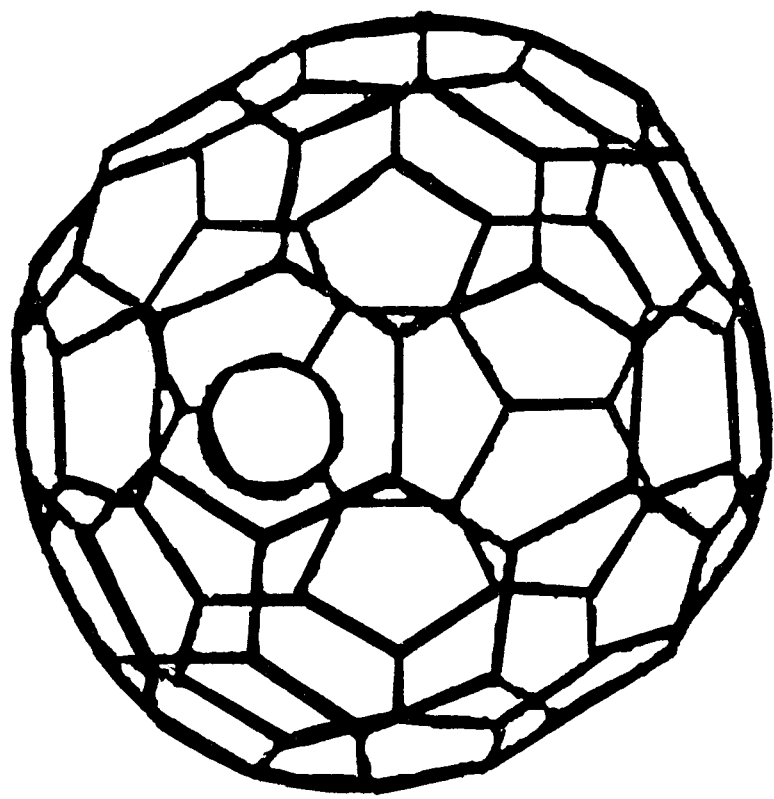
FIG. 10 Structure of a C82 fullerene containing an encapsulated atom.

Complete containment of the radionuclide can be achieved by using endohedral metallofullerenes (FIG. 10). Fullerenes are the third allotrope of carbon, a class of nearly spherical cages roughly one nanometer in diameter. The high strength of the carbon $sp^2$ bonds and durability of the fullerenes ensure that the encapsulated metal atom remains in the cage, even under beta recoil energies in excess of 10 eV (Kikuchi et al., 1994). The cage can be functionalized to become water-soluble without loss of integrity. Since the metal cannot escape a fullerene cage, isotopes with longer half-lives can reduce background radiation doses by allowing the mAb more time to find the cancer before decay occurs. These properties make fullerenes an attractive option to replace chelators for the delivery of radionuclides.

Multi-step targeting has shown promise as a means of increasing the T:NT ratio. The first injection in these methods is a bispecific antibody, where one end binds to the tumor and the other is specific for the chelating agent. The chelated radionuclide is injected later, after the bispecific antibody has achieved its maximum localization on the tumor. These methods suffer from the same problems that release radionuclides, but for a shorter time. Since the advantage is gained by using more rapidly circulating (and clearing) radiolabeled molecules, the smallest molecule that can firmly chelate the radionuclide and be specific for its receptor is desirable. In these respects, metallofullerenes are also ideal for radionuclide delivery in multi-step targeting.

Very recently, antibodies to empty fullerenes were developed by molecular bioengineering, providing a receptor for the metallofullerene. These new molecular tools prompted us to design an improved method for administering RIT. The radioisotope-containing water-soluble fullerene is administered after a bispecific antibody, where one end is the fullerene antibody (Abf) and the other is the tumor-specific mAb, has achieved its maximum localization on the tumor. Since the binding strength of the essentially hydrophobic fullerene to its own antibody can be very high, and water-soluble fullerenes will circulate rapidly without strong retention in any particular organ, this is a promising way to improve the T:NT ratio.

The specific aim of this research is to show that the metallofullerene $Ho@C_{82}$ (one holmium atom inside of a carbon cage containing 82 carbon atoms) can be derivatized to become water-soluble, and then bound to the bioengineered Abfs. $Ho@C_{82}$ will be bound to a monoclonal antibody bioengineered specifically for $C_{82}$ containing a metal atom. The available Abf at present is polyclonal produced in response to $C_{60}$, the most abundant fullerene. It is non-reactive with $C_{70}$, but not as yet been tested with $C_{82}$. The $C_{82}$ fullerene has been chosen as a host for the lanthanide because methods for its purification are much better developed than for other endohedral metallofullerenes. Virtually all lanthanides can be encapsulated with equal ease: holmium was selected because therapeutic applications of the $^{166}Ho$ isotope have already been proposed. The process of neutron activating $(Ho@C_{82})R$ (where R is a group inducing water solubility) to become $(^{166}Ho@C_{82})R$ is currently being studied. The attachment of metallofullerenes to antibodies is also to be studied.

Metallofullerene-based RIT treatments is one long term goal of these studies and precedents for mAb-based cancer therapies have already been established. For example, the mAb B72.3, developed at the National Cancer Institute, has been approved by the FDA and licensed by the NIH to pharmaceutical companies. Cytogen Corp. employs it as a basis for diagnostic agents for the detection and imaging of colo-rectal and ovarian cancers. More advanced, second generation antibody technology (CC49, e.g.) is also becoming available and is currently licensed for RII and RIT applications. Bispecific antibodies, such as MDX-210 (Medarex, Inc.) and 2B1 (Chiron Corp.), are also receiving approval for cancer therapies involving a triggering of the patient's own immune system.

Endohedral fullerenes and their produced derivatives may be purified and used in the methods developed in this study. Endohedral fullerenes are predicted to exhibit many unique properties that make them potentially valuable commodities. As an example, calculations predict that $C_{80}$ containing trapped lanthanide ions will be a high temperature superconductor.

With respect to medical markets, all applications involving the transport of metals in vivo can benefit from metallofullerenes. Ho@fullerene based materials may be used as radionuclide carriers and a specific use may be as labeling agents. Lanthanide-encapsulated fullerenes may also have potential use as labels that are detected by lanthanide fluorescence. Potential uses include fluorescent labels for tagging of amino acids, antibodies, nucleic acids, and other molecules used in enzymatic analysis, immunoassays, or DNA and protein sequencing applications. The fullerene label would also be useful in industrial applications requiring lanthanide labels that can survive extreme chemical environments.

Of all applications proposed for endohedral metallofullerenes, their use as radionuclide labels appears to be the most promising. Metallofullerenes are currently quite expensive to produce and purify. Therefore, potential near term applications need to be high value and require only small amounts of material. Radionuclide labels for immunoguided applications fit this requirement exactly. Medical applications are intrinsically high valued, and the amount of material required is extremely small ($\mu$g's or less). With future improvements in the areas of metallofullerene production and purification, the cost should be lowered within the next few years. Then the use of a metallofullerene label with a monoclonal antibody would contribute only a small fraction to the total cost of the treatment.

The present studies are made to demonstrate that endohedral metallofullerenes can be linked to antibodies. The results of this study have significant implications for all applications involving transport of toxic metals in vivo. This research will lead to the development of a new method of transport of toxic metal atoms in vivo, possibly providing an improved method of guiding the radionuclide to the tumor in RIT and RII.

B. Significance

This section begins with a review of metallofullerenes, highlighting their potential and limitations for RIT. Replacing chelates with metallofullerenes requires a significantly different, but probably advantageous, procedure for the attachment of the radionuclide to the mAb. Many targeting strategies for RIT have been developed. To focus on the correct one requires significant knowledge of the binding strengths, specificity, and pharmacokinetics of the different pieces of the metallofullerene-bispecific antibody being assembled. The available fullerene biodistribution studies, important if multistep targeting approaches are considered, all conclude that fullerenes are nontoxic. The distributions are dependent on the functionality used to induce water solubility in the fullerene. The process used to create antibodies to fullerenes is then summarized, including studies demonstrating the high specificity of the antibodies. This series of experiments concludes with an outline of potential strategies for RIT based on a fullerene carrying the radionuclide.

B.1 Metallofullerene Background

Fullerenes are a new class of hollow, closed shell, all carbon molecules discovered by R. E. Smalley and co-workers in 1985 (Kroto et al. 1985). The feasibility of encapsulating metal atoms inside the fullerenes was proven by Smalley's group (Heath et al. 1985) shortly after their initial discovery. Subsequent gas phase photofragmentation experiments showed that fullerenes are among the most stable molecules known to exist, able to store up tp 50 eV (delivered by photo bombardment) in internal energy (Wurz and Lykke, 1992). The first bulk amounts of fullerenes were synthesized by resistive heating of graphite in an inert He atmosphere in 1990 by Huffman and Kratschmer (Kratschmer et al. 1990).

Bulk quantities of fullerenes containing La atoms were first synthesized by R. E. Smalley's group in 1991 (Chai et al. 1991). The first metallofullerene samples were produced by laser valorization of $La_2O_3$ impregnated graphite rods in a tube furnace at 1200° C. Later experiments demonstrated that endohedral fullerenes could also be produced in usable amounts by the conventional arc evaporation of metal oxide or metal carbide impregnated graphite rods (Johnson et al. 1992). Electron paramagnetic resonance (EPR) studies of toluene soluble $La@C_{82}$ later prowled that the La atom was in the +3 valence state with the fullerene functioning as a compensating anion (Johnson et al. 1992). Recent x-ray diffraction studies on $Y@C_{82}$ prove conclusively that the metal atoms are encapsulated inside the fullerene (Takata et al. 1995).

It has since been shown that it is possible to produce bulk amounts of fullerenes containing Ca, Sr, Ba, Sc, Y La=lanthanides, and U as well as fullerenes containing multiple metal atoms such as Y dimer and Sc trimer (Bethune, 1993). in general, the production of metallofullerenes creates a broad range of endohedral species containing from 60 to 200 carbon atoms and one or more metal atoms. However, attempts at large-scale encapsulation of metals outside of Group II and Group III have met with little success. High pressures can induce noble gas atoms to enter the cage in very small quanities (Saunders et al. 1996). A recent report of $^{99m}$Tc encapsulation (Karem et al., 1997) lacks the definite photofragmentaion test (Heath et al., 1986) to prove encapsulation rather than external complexation.

Metallofullerenes are made using stable isotopes of the lanthanides (Section D.1 infra), and later activated under a slow neutron flux to form radionuclides. By first producing, purifying, and derivatizing the non-radioactive metallofullerene, the time from acquisition of the radionuclide to its administration for RIT is greatly reduced. Thermal neutron activation of $^{165}$Ho@C$_{82}$ fullerenes has been used to create $^{166}$Ho@C$_{82}$ fullerenes with up to 8% survivability after 5 hours of irradiation under a flux of $4*10^{13}$ neutrons/cm$^2$/s (Cagle et al., 1996). The low yield appears to be due to the fast neutron component, perhaps 25% of the neutrons, although recoil from prompt gamma emission may also play a role in degradation of the fullerene cage. The present studies are extended to include Ho@C$_{82}$ fullerenes derivatized to be water soluble. Neutron activation of endohedral metallofullerenes offers a viable path for encapsulation of radionuclides, but further restricts the choice of radionuclide to one that can be readily produced by neutron activation. However, the surviving metallofullerenes are ready for immediate use, whereas the slow uptake of short-lived isotopes into chelates reduces their effectiveness.

Despite the limitations imposed by the elements which can be encapsulated and the n neutron activated, a wealth of potential radionuclides remain. Table 1 depicts the potential lanthanide beta-emitters with a thermal neutron capture cross sections of about 10 barns. The $^{166}$Dy/$^{166}$Ho pair is particularly intriguing, as it offers the chance to deliver two β$^-$ particles per radionuclide.

TABLE 1

Potential lanthaide radioisotopes.

| Isotope | Production Cross Section (barns) | half life | β-energy (MeV) |
|---|---|---|---|
| $^{140}$La | 9 | 40 h | various; to 2.2 |
| $^{142}$Pr | 12 | 19 h | 2.2 |
| $^{166}$Dy | 1000* | 82 h | 0.5 |
| $^{166}$Ho | 65# | 27 h | 1.8 |
| $^{170}$Tm | 105 | 129 d | 1 |
| $^{175}$Yb | 65 | 4.2 d | 0.5 |
| $^{177}$Lu | 25* | 7 d | 0.5 |

*indicates that two steps are required, but the second step has a cross section of at least 1000b.
indicates that it is also produced as the daughter of the $^{166}$Dy decay. All production cross sections are based on neutron capture by the A-1 isotope.

Unlike chelates, fullerene cages withstand recoil energies between 10 and 100 eV (Kikuchi et al., 1994). Early studies suggested that recoil energies less than an electron volt are likely to rupture chelating bonds (Asano et al., 1974; Glenworth and Betts, 1969; Glenworth 1961), although more recent work asserts that all of the $^{166}$Ho formed from $^{166}$Dy decay (recoil energy of 1.85 eV) is retained in the DPTA chelate (Smith et al., 1995). Highly energetic decays with larger recoil energies are desirable because they improve the dose per radioisotpe, as long as the radiated particle pathway is not much larger than the tumor. As blood flow to the center of the tumor is usually severely restricted, more energetic decays offer improved therapy against larger tumors. Losing the metal during recoil (a problem with chelates but not fullerenes) may result in additional toxicity, particularly from the lanthanides which have biological half lives on the order of a decade. This is especially relevant as much recent work has been devoted to the lanthanide beta emitters $^{90}$Y and $^{166}$Ho, amongst others.

These studies will concentrate on producing, purifying, and derivatizing Ho@C$_{82}$. There are three main reasons for concentrating on C$_{82}$ based compounds. First, for reasons that are not well understood, slightly more C$_{82}$ lanthanide fullerenes are produced than other metal [ ]-[ ]containing fullerenes. Second, unlike other lanthanofullerenes C$_{82}$-based metallofullerenes are relatively stable with respect to oxidation in air and should be chemically similar to empty fullerenes (Suzuki 1993). Recently, the synthesis of derivatized metallofullerenes has confirmed this hypothesis (Suzuki et al. 1995 and Akasaka et al. 1995). Third, only C$_{82}$ metallofullerenes are soluble in organic solvents such as toluene and can be extracted and purified using currently; available chromatography methods (Section D.2).

B.2 Fullerene Pharmacology

Research into the biological attributes of fullerenes as a class has only just begun. Several preliminary studies indicate that the fullerenes are well tolerated, are relatively nontoxic in vivo, and are certainly much less toxic than free lanthanide ions. The results of these studies are summarized infra.

Because of concerns of the potential carcinogenic effects of benzene and related polycyclic aromatic compounds (of which fullerenes, because of their π-conjugated surfaces might be considered similar), a study on the effect of topical fullerenes was undertaken by Nelson et al. (1993). They demonstrated a lack of carcinogenic effects from C$_{80}$ and C$_{70}$ after acute and subchronic applications to mice.

Tours and coworkers (W. A. Scrivens et al. 1994) produced $^{14}$C labelled C$_{60}$ suspensions (particle size 0.30 μm average diameter) in water and studied its uptake into human keratinocytes. The keratinocytes were exposed to the labelled fullerenes (32,000 dpm, 1.3 μM) and the uptake of the labelled C$_{60}$ into the cells was monitored. After 6 hours approximately 50% of the applied radioactivity was taken up by the keratinocytes with no further increase noted for longer exposures. Washed cells continued to contain the suspended fullerenes over the next 11 hrs. Experiments to determine the effect of the C$_{60}$ suspension on the proliferation rate of human keratinocytes and fibroblasts by monitoring of labelled thymidine uptake showed fullerenes had no effect on the rate of thymidine uptake.

Figure 11:
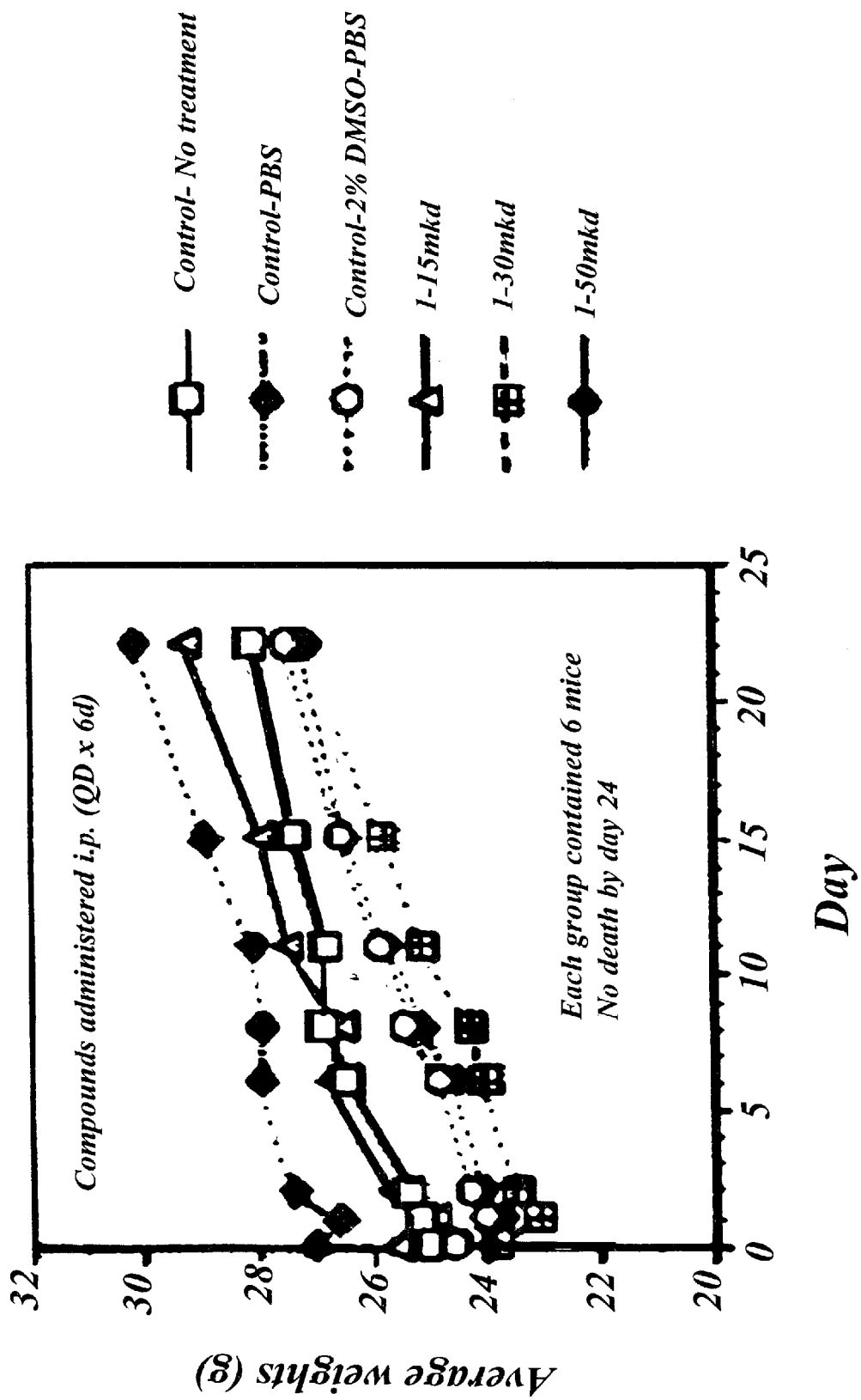
FIG. 11 Effect on weight gain of the fullerene derivative in Swiss mice (R. F. Schinazi et al. 1994).

The only systemic toxicity studies reported in the literature so far are those performed by R. F. Schinazi et al. (1994). In this study, a water soluble fullerene based HIV protease inhibitor was administered to groups of 6 mice at dosages of 15, 30, and 50 mkd. After a slight decline in weight in the treated and control groups (except for the untreated control group) all of the animals gained weight over the period of observation (see FIG. 11) and none of the animals died. There was no statistical difference in the weight between the treated versus control groups and the authors concluded that their fullerene derivative is well tolerated up to a dose of at least 50 mkd. Continued monitoring showed none of the animals had died at 2 months after the start of the experiment.

The in vivo distribution of a particular water soluble $^{14}C$ labeled fullerene administered to mice has also been determined (Yamago et al. 1995). After injection, the compound moved quickly to the liver and then was distributed to various other tissues. No acute toxicity was noted at doses as high as 500 mg/kg, and all of the mice survived the one week test period. However, excretion of the compound was slow, with 90% being retained after one week. It also appears that the water solubilizing functional group, which contained the $^{14}C$ label amid several ester linkages, was metabolized off of the fullerene. This suggests that the distribution and biological half life of fullerene derivatives may depend on the type of functional groups attached to the fullerene. Interestingly, in spite of the fact that it is a fairly large molecule, the fullerene derivative was able to cross the blood brain barrier, a fact that could be very important for future metallofullerene labelled pharmaceuticals.

The biodistribution in mice of hydroxylated lanthanide-$C_{82}$ encapsulates is under current investigation. The results presented here are regarded as preliminary as the sample is still small. Studies continue under a NIH Phase I grant. The neutron irradiated samples, along with a $^{166}Ho^{3+}$ control sample, were used to perform a γ-camera imaging study on four 300 g Sprague-Dawley rats. Two rats were injected intraperitoneally (IP) with 54 and 18 μCi of $^{166}Ho$ activity from samples containing irradiated Ho-metallofullerois. Two control studies were performed by IP administration of approximately 660 μCi of $^{166}Ho^{3+}$ in a 1% sodium citrate buffer. The anesthetized rats were scanned side-by-side on a single stage with a γ-camera starting 1 hour after injection and periodically thereafter over the ensuing 48 hours.

The in vivo imaging of the control rats showed rapid $^{166}Ho^{3+}$ urinary clearance commencing, as soon as 1 hour post-injection. After 24 hours, essentially all $^{166}Ho$ activity had been excreted from the controls. In contrast, the $^{166}Ho$ activity from the Ho-metallofullerois produced a discernible image for up to 48 hours and showed an even distribution throughout the blood pool. Essentially no tissue localization was evident. After 48 hours, the $^{166}Ho$ activity in the test rats became too low to image effectively ($^{16}Ho$ $t_{1/2}$=26.8 hrs)

Figure 12:
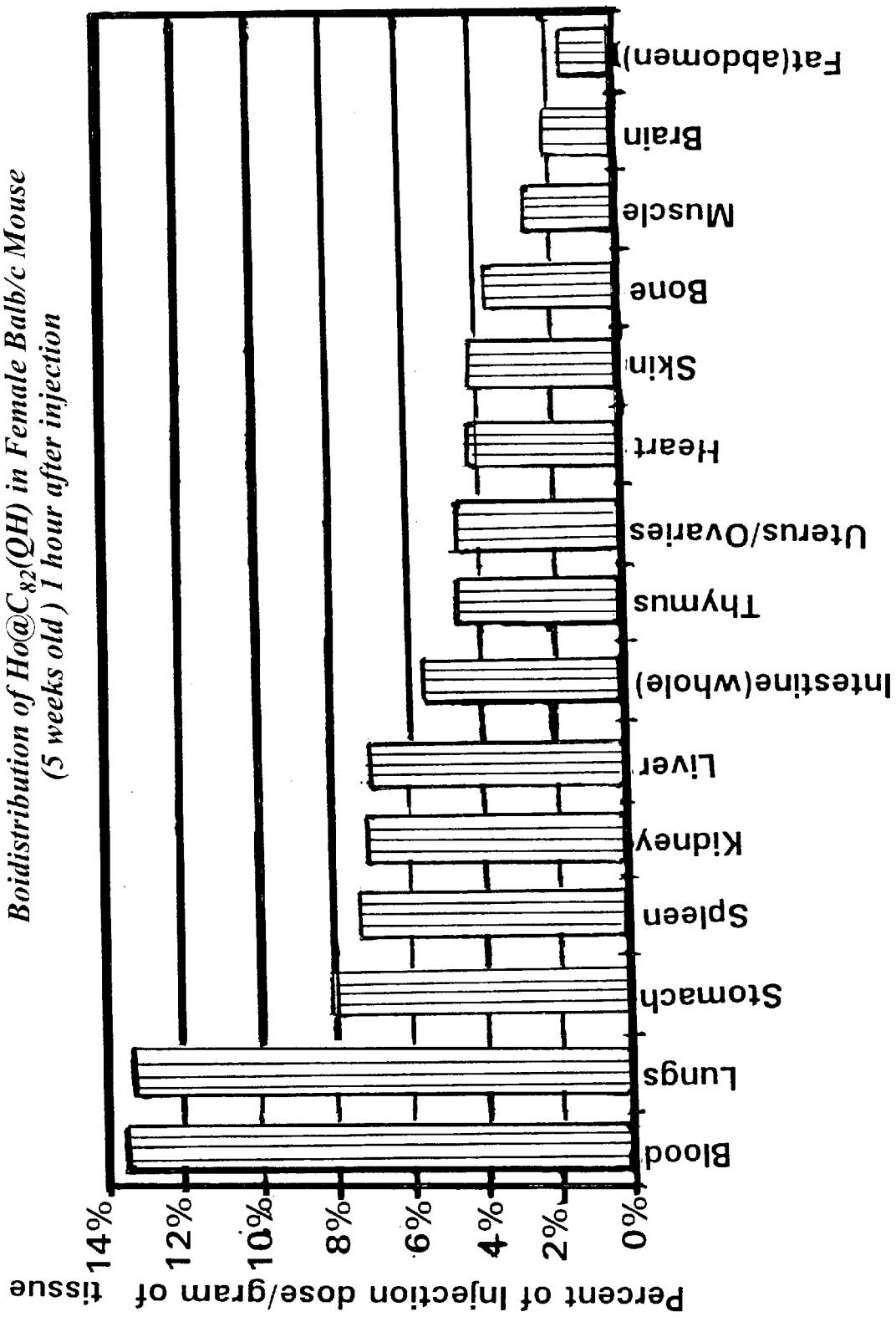
FIG. 12 Measured biodistribution of Ho@C$_{82}$(OH)$_x$ metallo-fullerol.

A second biodistribution study was performed on a single Balb/c mouse to provide a more detailed view of how the Ho-metallofullerol localized in vivo. The results of this study are shown in FIG. 12. Counting of the tissues shown was performed 1 hour after injection with the activities related back to the initial injected dose and corrected for the half-life decay. Additional $^{166}Ho$ activity was also counted in the animal's cage, indicating that some clearance of the compound had occurred in the 1 hour before analysis.

Whereas previous fullerene biodistribution studies have demonstrated rapid liver uptake and retention, both of the present studies show that this is not the case for the metallofullerol samples. It appears that the type of derivation used to water-solubilize the fullerene is an important factor in determining its in vivo localization. From a RIT point of view, these initial metallofullerol results are very encouraging. While the long-term biological fate of the presently studied Ho-metallofullerol is unclear because of the short $^{166}HO$ half-life, it seems rather certain that the observed biodistribution differs from that of simple lanthanide salts as well as underivatized fullerenes. Further testing with samples of higher activity and longer-lived radioisotopes will be necessary to fully resolve this question.

A very recent study reported by Dugan et al. in the Aug. 19, 1997 *Proceeding of the National Academy of Sciences* reports that water-solubilized fullerenes "act as an effective anti-oxidant", sweeping up free radicals. Their studies, conducted on oxygen-and glucose-starved nerve cells which build up damaging free radicals, showed that the addition of a water-soluble fullerene derivative (derivatized by carboxylic acid groups) could cut cell death by 75%. Administration of the compound to mice bred to mimic familial amyotrophic lateral sclererosis (Lou Gehrig's disease) delayed the onset of symptoms by 10 days and increased their average 130 day life-span by 9 days. Dosing was accomplished by mini-osmotic pumps starting at 73 days of age and continuing until death. The administered dose corresponded to 15 mg/kg/day, and an equivalent dose for a typical 70 kg human (1.05 g[.]) far more than that required for RIT. There appears to be no toxic effects from doses in this size range. The use of polyhydroxylated fullerols similar to those investigated in this project an non-toxic in vivo free radical scavengers has also been demonstrated (Tsai et al. 1997 and Chueh et al. 1997). From the limited number of studies that have been performed, it seems that the fullerene cage unit is non-toxic. Subject to further, more detailed investigations, it appears the future of fullerenes and metallofullerenes in medicine is quite promising.

B. 3 Fullerene Antibodies

Excellent, high-affinity polyclonal antibodies to fullerenes have been prepared by essentially conventional methods. Anti-fullerene antibody formation proves that fullerene compounds are processed by the immune system in the same way as any other small molecule antigens. Specificity of the antibodies was confirmed by both binding and inhibition studies.

Figure 13:
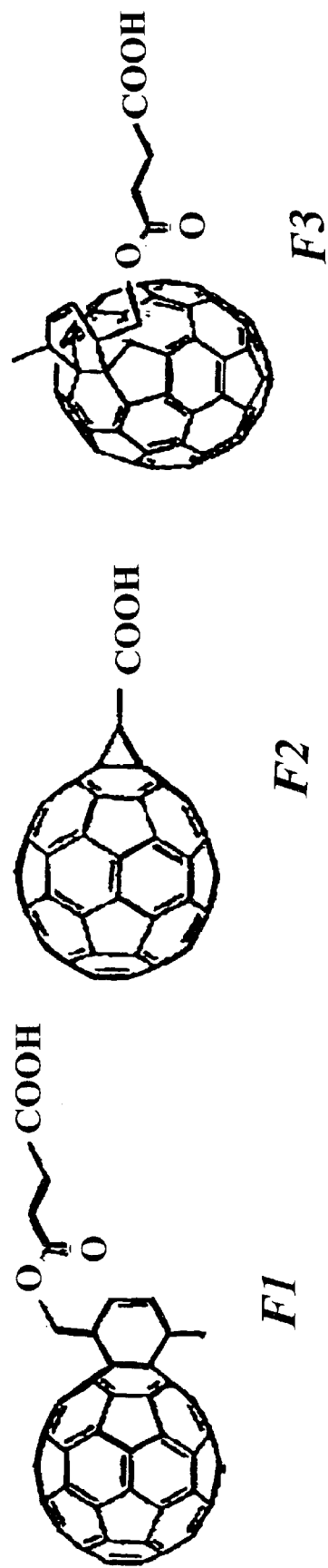
FIG. 13 Fullerene derivatives to which anti-fullerene antibodies were produced by immunization of mice with a bovine thyroglobulin (TG) conjugate of a fullerene hemisuccinate F1 containing ca. 10–12 fullerenes per TG molecule. F3 is a C70 derivative.

The anti-fullerene antibodies were produced by immunization of mice with a bovine thyroglobulin (TG) conjugate of a fullerene hemisuccinate F1 containing ca. 10–12 fullerenes per TG molecule (FIG. 13). After a primary immunization in Freund's adjuvant and two subsequent booster injections, the antibody response was confirmed by ELISA. The ELISA plate was coated with F1-rabbit serum albumin (RSA). Preimmune and post-immune sera were examined. Development was with horseradish peroxidase-labeled anti-mouse IgG, using o-phylenediamine as substrate. A high titer of antibody was confirmed (FIG. 4, first series of experiments).

Figure 14:
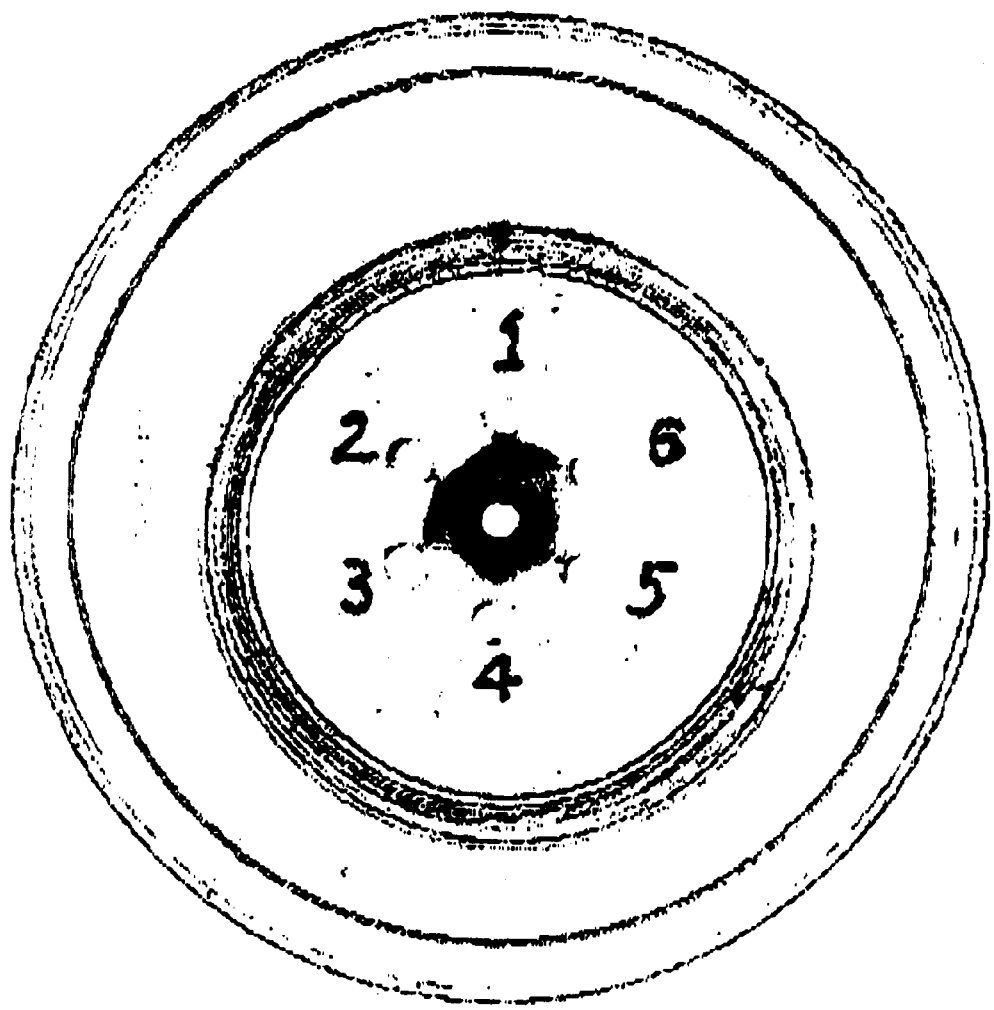
FIG. 14 Results of the double diffusion in agar experiment. Will 1 represents the F1-TG immunogen; 2, the F2-TG immunogen; 3, F1-BSA conjugate; 4, F1-RSA conjugate; 5, F3-RSA conjugate; and 6 is empty.

Specificity of the antibodies was confirmed by double diffusion in agar (FIG. 14). Lines of precipitation are seen in wells #1, 2, 3, 4, and 5, with a spur of #2 precipitate "pointing" to F1-BSA. This implies an additional reactive epitope in the F1-TG not present in its BSA conjugate. The overall interpretation of this experiment is that a population of $C_{60}$-specific antibodies was produced, a subset of which also bound F3, a $C_{70}$ derivative.

Figure 15:
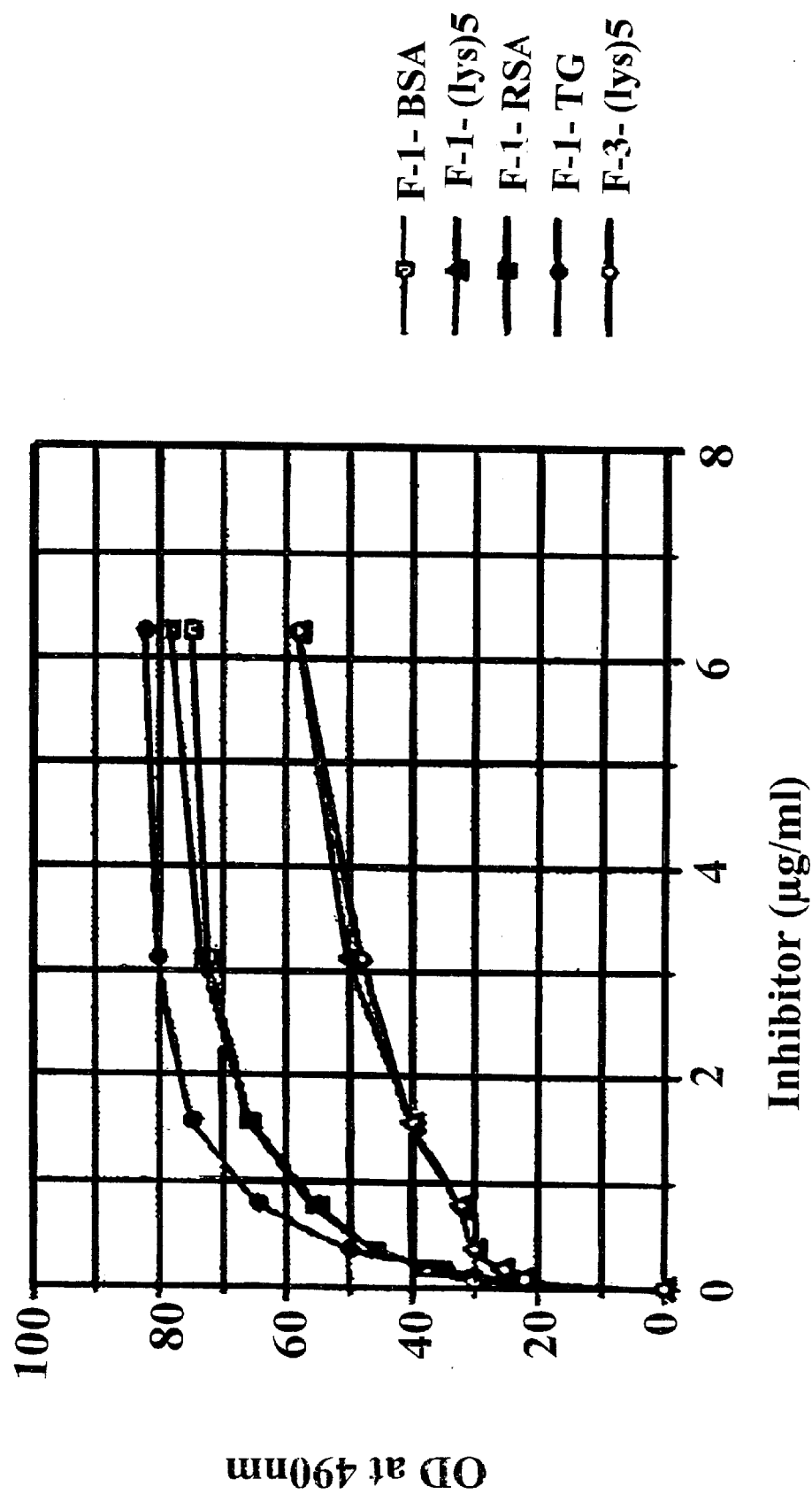
FIG. 15 ELISA inhibition test results.

The specificity of the antibodies was confirmed by ELISA inhibition studies (FIG. 15). Binding to F1 covalently linked to RSA was inhibited by F1-BSA, F1-RSA, F1-TG, F3-pentalysine, and F1-pentalysine. The pentalysine derivatives contained ca. 2.8 fullerenes per pentalysine molecule and were water soluble. This demonstrates that the antibody is specific for the fullerenes, not the conjugates. As the polyclonal Abfs also bind $C_{70}$, a fullerene of intermediate size and somewhat more elongated shape, the likelihood of them accommodating the $C_{82}$ cage seems very high.

Success at binding metallofullerenes to antibodies has profound implications for all techniques involving the transport of metals in vivo. While the fullerene keeps the metal completely contained, the Abf provides a handle for manipulation of the fullerene in vivo.

B.4 Radioimmunotherapy with Metallofullerenes

This work is aimed at RIT for several reasons. Primarily, the radioactive metals allow the most sensitive measurement techniques to be applied to tracking the development of the process, both in vivo and in vitro. Secondly, RIT has attracted much attention due to its great promise, but requires a technological breakthrough before it can be widely applied. A recent review (Wilder et al., 1996) summarizes the (mostly) very low response rates in clinical trials of RIT. Recent research has been towards shorter half-life radioisotopes, metabolizable linkages, and rapid clearing of the chelated radioisotope. These strategies are attempts at reducing the background dosage when the mAb does not rapidly find the tumor, compensating for its eventual separation from the radioisotope. If all metal atoms remain encapsulated over any length of time, as is true for metallofullerenes, the radionuclide is never separated from the mAb by leaving the chelate. Longer-lived radionuclides, such as $^{177}$Lu, suffer fewer decays while the mAb is locating the tumor, and therefore take best advantage of the metallofullerene delivery for one-step targeting (Schlom et al., 1991).

However, a single dosage of the fullerene-bispecific antibody may not be the best way to apply fullerenes to RIT. Some of the conventional problems have been mitigated by two-(Hnatowich et al., 1987) and three-step (Paganelli et al., 1991) targeting approaches. Use of metaollothone in (~7 kDa) as a chelator is attractive because it is readily fused to other proteins by recombinant DNA technologies (Virzi, et al., 1995).

However, its chelation ability was very poor in comparison to the more recent advanced synthetic chelating agents. A more common approach has been to link a good chelator (loss of ~1% of metal atoms per day) to biotin (Vitamin H). Such assemblies have slightly lower molecular weights than fullerenes, indicating rapid circulation (and clearance) in vivo. Some problems have been encountered with cleavage of the chelator from biotin (Rosebrough, 1993). In the three step program (Paganelli et al., 1991), a bispecific mAb, combining biotin with the antigen-specific component, is administered first. Avidin, which has an association constant for biotin of order $10^{15}$, is added in the second step. In the final step, the biotin-chelate conjugate binds to the avidin. Even with this optimized (but arduous) administration program, only 0.012% of the injected dose was delivered to the tumor.

Similar multi-step approaches may be suitable for metallofullerene derivatives, depending on their pharmacokinetics. One possible strategy is to first administer a bispecific antibody that consists of an antigen-specific component and the Abf, followed by the metallofullerene. The available biodistribution studies of fullerenes indicate that, without stable functionalization to induce water solubility, they rapidly accumulate in the liver, from which clearance requires days. However, when water solubility is maintained, the mouse biodistribution indicates that fullerenes do not accumulate in any particular organ. As there are no natural receptors for fullerenes, they may exhibit very high in vivo selectivity for the Abf. Determination of binding constants, development of targeting strategies, and location of appropriate antigen-specific antibodies to link the Abf are all appropriate tasks for Phase II research.

C. Experimental Design and Methods

Figure 16:
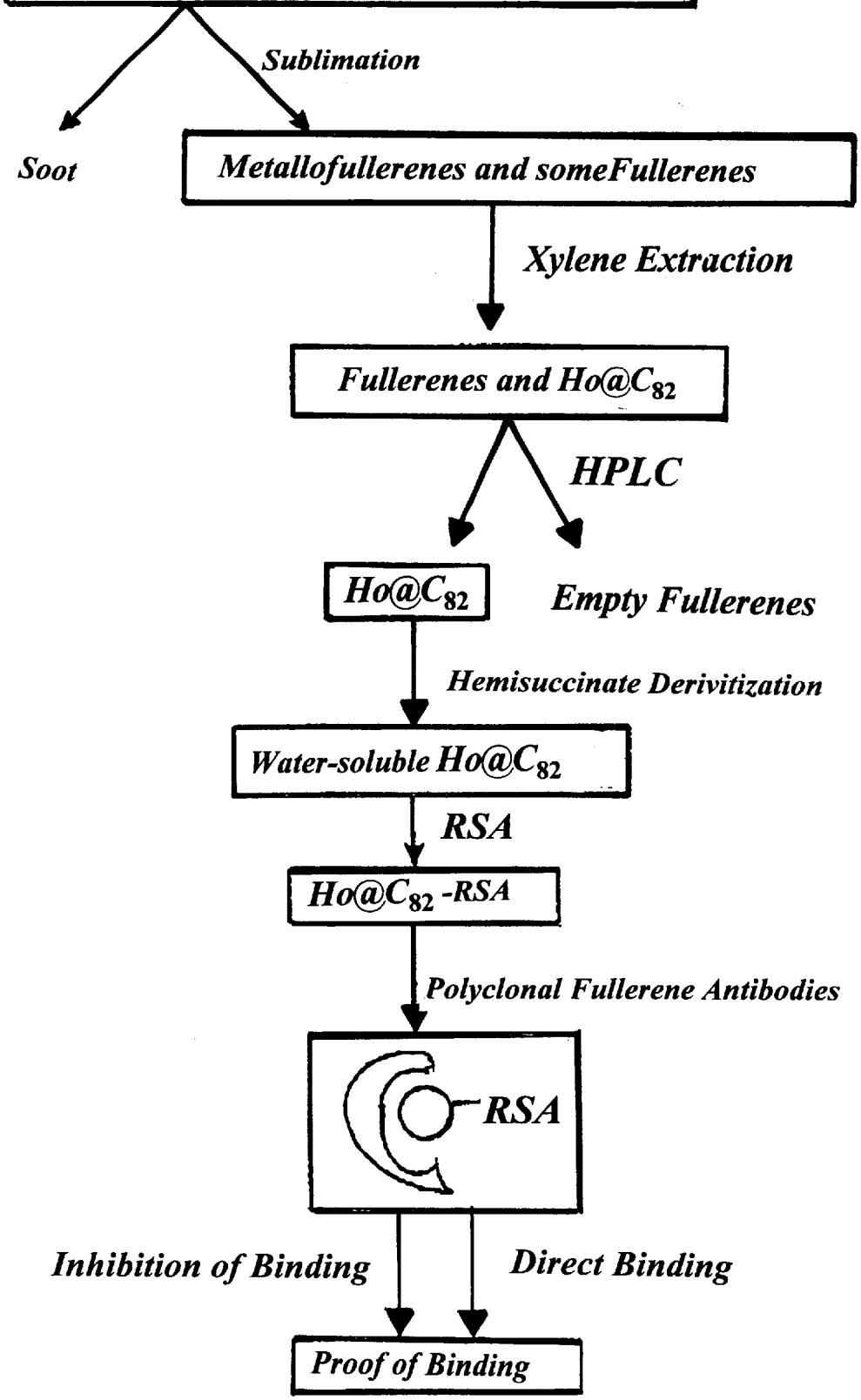
FIG. 16 The flow of the research studies (see infra Fourth Series of Experiments).

The goal of the Phase I project is to demonstrate that endohedral metallofullerenes can be attached to fullerene antibodies. While these studies will isolate monoclonal antibodies for $C_{82}$ with endohedral metal atoms, the work begins with the polyclonal mixture bioengineered in response to empty $C_{60}$. Four tasks consistent with this specific aim have been formulated: 1)Synthesize holmium containing fullerenes; 2)Purify the selected Holmiom fullerene; 3) Derivatize the purified Ho@$C_{82}$ to make it water soluble; 4) Bind, the derivatized Ho@$C_{82}$ to the fullerene antibodies. FIG. 16 shows the flow of the research studies.

C.1 Task 1: Production of Holmium Metallofullerenes

The evaporation of graphite using a carbon arc in an inert atmosphere was the first successful approach for the production of macroscopic amounts of fullerene materials. This technique has also proven to be the method of choice for the production of macroscopic amounts of endohedral metallofullerenes as well. The graphite that is vaporized is doped with the desired metal in a form, such as $Ln_2O_3$, that is readily reduced to the neutral metal during vaporization. The metallofullerenes utilized in this project are likely to be produced by the conventional carbon arc method as described below.

A current Phase II project is underway to produce bulk (kg) quantities of fullerenes and metallofullerenes using a continuous, combustion based process that can employ organometallic precursors. This process will substantially lower the cost of all types of fullerenes. Since its success is not guaranteed, described herein is a proven method for production of fullerenes and metallofullerenes.

A unique carbon arc reactor capable of both producing fullerenes and separating all the fullerenes from the raw soot has been designed. Because some fullerenes are radicals, all processing is performed under anaerobic conditions. The reactor is constructed primarily from quartz and serves to both vaporize the carbon rods and to perform an initial sublimation step. It is capable of generating several hundred milligrams of sublimed fullerene/metallofullerene mixture per 5" length of ¼" rod vaporized. The reactor is currently run in a single rod made by butting the ¼" rod to be vaporized against a larger ½" diameter rod. The arc is run in DC mode with the polarity being reversed every few minutes to insure uniform evaporation. Multiple rods can be sequentially vaporized without venting the system by loading new rods into the reactor through the ball valve. Metal oxide doped carbon rods are produced by incipient wetness impregnation, a procedure developed at TDA and adequately described in the literature (Cagle et al., 1996). During the vaporization step, the fullerene collector is replaced by a seal to keep soot from going past the quartz baffle plate, and the tube furnace is removed to allow dissipation of the excess heat. Analysis of soot samples from different areas of the reactor after vaporizing one undoped graphite rod showed the yield of empty fullerenes (determined by quantitative HPLC) to be ~12%.

After evaporating several sets of graphite rods, the apparatus is pumped out to a vacuum of ~10 mtorr, and the electrodes are withdrawn. The furnace is replaced, and the quartz vessel is heated to 250° C. to allow any volatile impurities to be pumped away. The water cooled collector is now inserted through the gate valve, and the furnace is programmed to heat to 750° C. over several hours. The collector provides a water cooled surface area of 65 cm$^2$ upon which the fullerenes and metallofullerenes condense. Typical films, depending on the quantity of evaporated material, are on the order of 20–100 μm thick. Depending upon the metal, approximately 200–1000 mg of sublimed material can be collected. From our current data, it is estimated that the yields collected by sublimation are equivalent to that collected by solvent extraction, but in contrast to solvent extraction, all of the small gap empty fullerenes and endohedral metallofullerenes produced (up to about 100 carbon atoms) readily sublime onto the collector. By performing the sublimation in two steps, at least 30% of the $C_{60}$ and $C_{70}$ can be removed in a first pass at 500 C., without losing significant amounts of Ln@$C_{82}$. This renders the higher temperature sublimate more concentrated in Ho@$C_{82}$ crucial to its efficient purification (vida infra).

Figure 17:
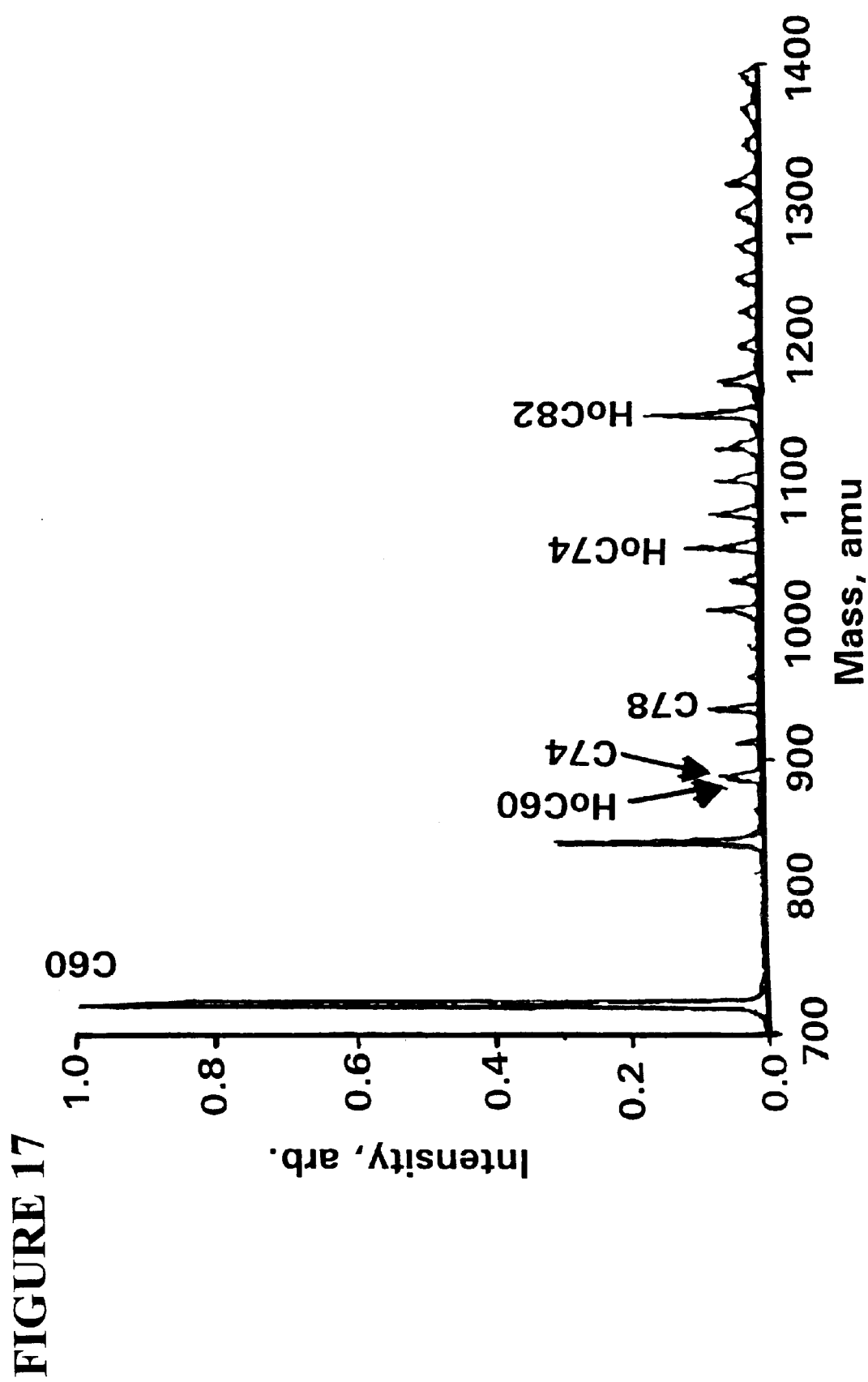
FIG. 17 A mass spectrum (MS) of a typical sublimed sample (single step at high temperature) of Holmium (Ho) containing fullerenes is shown.

A mass spectrum (MS) of a typical sublimed sample (single step at high temperature) of Ho containing fullerenes is shown FIG. 17. This spectrum was obtained with TDA's laser desorption time-of-flight reflectron mass spectrometer. Metallofullerene samples were deposited on a stainless steel target disk from suspensions made by sonicating the metallofullerene solid in ethanol. Desorption and ionization were performed with 355 nm light from a Q-switched Nd-YAG laser. Peak intensities between the empty and metallofullerenes are not always quantitative, since metallofullerenes are easier to ionize than the empty fullerenes. In this case, empty fullerenes require three 355 nm photons to ionize while metallofullerenes require only two. The net result is an apparent enhancement of the metallofullerene signal (we estimate by a factor of two, based on measurements made using 157 nm light where 1 photon ionizes all of the fullerenes.) This makes Ho@$C_{82}$ about as abundant as the higher empty fullerenes such as $C_{84}$.

C.2 Task 2: Purification of the Ho@$C_{82}$

Fullerenes from the concentrated sublimate will then be dissolved in xylene. Among lanthanide endohedral metallofullerenes, only the $C_{82}$ encapsule is soluble, which provides a rapid means of achieving purity among endohedral fullerene cage sizes. After filtering to remove the insolubles, the extract will be separated into its components using a semi-preparative high pressure liquid chromatography (HPLC) technique. Commercial columns with stationary phases have been developed specifically for separating fullerenes. A variety of these fullerene HPLC Columns are available and it has been found that the Cosmosll PYE (2-(1-pyrenyl)ethyl) column is the best for Ln@$C_{82}$ separations. Much expertise in HPLC separation of Ln@$C_{82}$ has been acquired as the result of a previous study of Gd@$C_{82}$ as an MRI contrast agent. Thus, examples are cited from that procedure. The procedure for optimizing the collection of Ln@C82 was developed during that work, and will be applied to the Ho@$C_{82}$ effort proposed here. It is not expected that the change from Gd to Ho will result in any significant behavioral differences in the HPLC of the endohedral metallofullerenes.

While previous work reported in the literature performed HPLC under aerobic conditions, (see for example Funasaka et al. 1995) these studies determined that anaerobic controls better preserved the fraction of Gd@$C_{82}$ in solution. (The hydroxylated, water soluble Gd@$C_{82}(OH)_x$ derivative does not appear to be air sensitive.) Pure, degassed o-xylene was used as the mobile phase at a flow rate of 8 ml/min, and all handling of the sample solutions was performed using anaerobic Schlenk line techniques. The fraction containing the Gd@$C_{82}$ was identified using MS. The solubility of fullerenes in o-xylene is about three times that of toluene and this greatly increases the ratio of fullerenes in solution to those retained on the stationary phase. Therefore, the capacity or amount of fullerenes purified per injection was very large. Each injection contained 2 ml of saturated fullerene o-xylene solution (about 30 mg of fullerenes).

Figure 18:
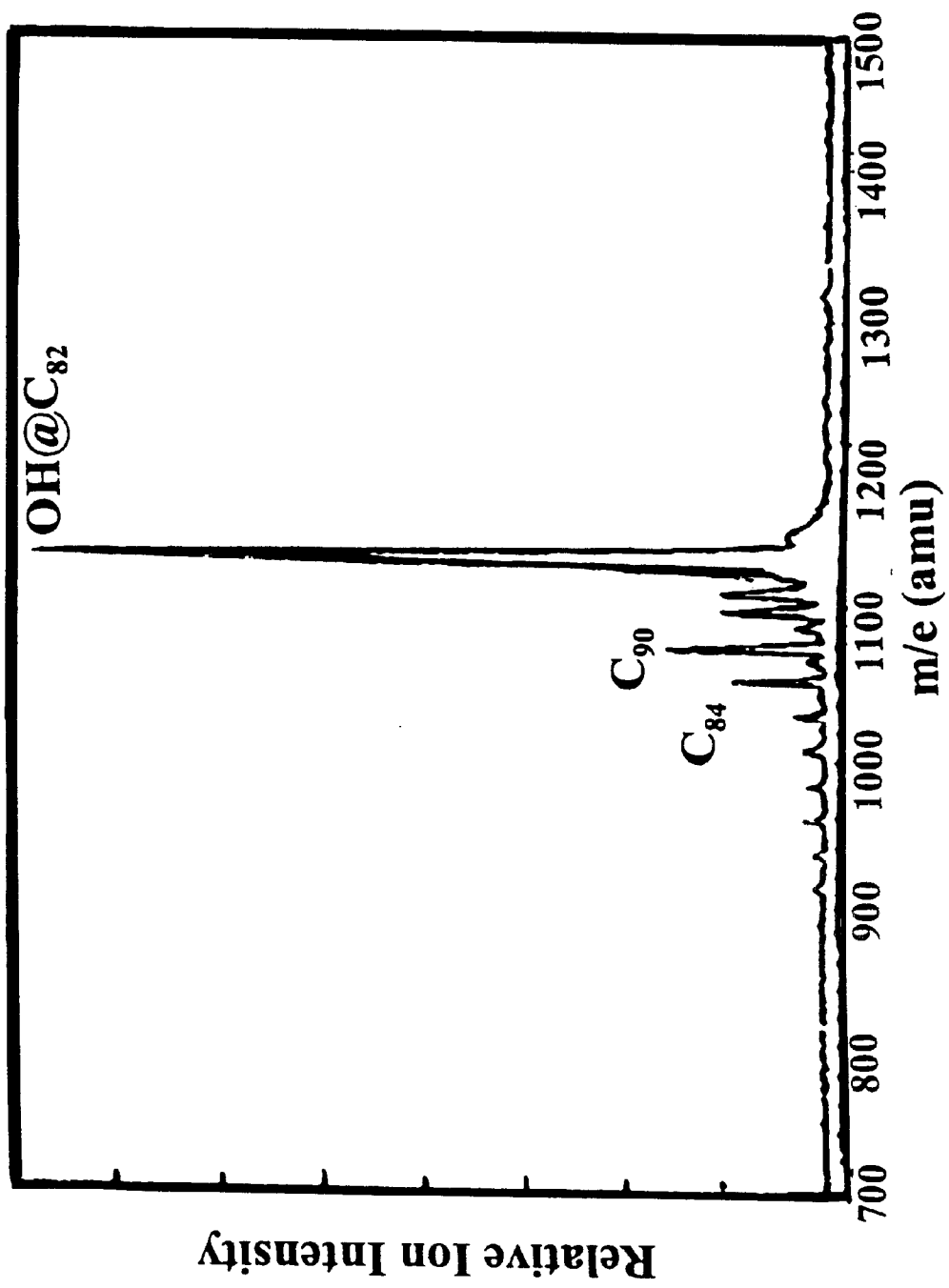
FIG. 18 Purified Gd@C$_{82}$ using a single stage, anaerobic HPLC method applied to the high temperature sublimate.

The Gd@$C_{82}$ fraction was, collected under Ar as it eluted from the column. The final solution, shown in FIG. 18, was then stored under Ar until ready for derivatization. Because we started with a highly enriched fraction and handled it anaerobically, the purity of the sample is quite high (the integrated area is ~95% Gd@$C_{82}$, but as explained earlier, the absolute calibration is uncertain). The need for only a single, short HPLC step greatly facilitated separation of large quantities of Gd@$C_{82}$, and the production and purification process was then repeated to successfully produce approximately 25 mg of the material shown in FIG. 11. Repeating this procedure for holmium fullerenes will collect an appropriate amount to prepare the water soluble derivative.

C.3 Task 3: Producing the Water Soluble Holmium Fullerenes

The Ho@$C_{82}$ will need to become water soluble in order to attach it to the fullerene antibodies. A wide variety of reactions have been shown to make $C_{60}$ water soluble. Functionalization of the outside of the cage with about thirty hydroxyl groups has also been shown to be effective for endohedral metallofullerenes. One or more carboxylic acid groups have been linked to the fullerene in a variety of ways to induce water solubility. Inclusion in cyclodextrin and poly(vinylpyrrolidine) have also been successful. Polyhydroxylation, cyclodextrin inclusion, and complexation with poly(vinylpyrrolidine) are expected to alter the exterior of the cage beyond the recognition of the Abfs. Therefore, a carboxylic acid group is linked to the metallofullerene.

While only one other reaction of Ln@$C_{82}$ has been demonstrated (besides polyhydroxylation, and that other one does not produce a water soluble derivative), the chemistry of the endoheldral metallofullerenes is likely to be very similar to that of the empty fullerenes. The organic chemistry of empty fullerenes is a rapidly growing field, led by reactions of $C_{60}$. All chemical principles demonstrated on $C_{60}$ also hold for larger fullerenes, although the isomeric mix of products varies according to the cage size and shape. The hemisuccimide derivative used in the initial preparation of $C_{60}$ antibodies was also demonstrated for $C_{70}$, and the same procedure will be followed for the Ho@$C_{82}$.

Figure 19:
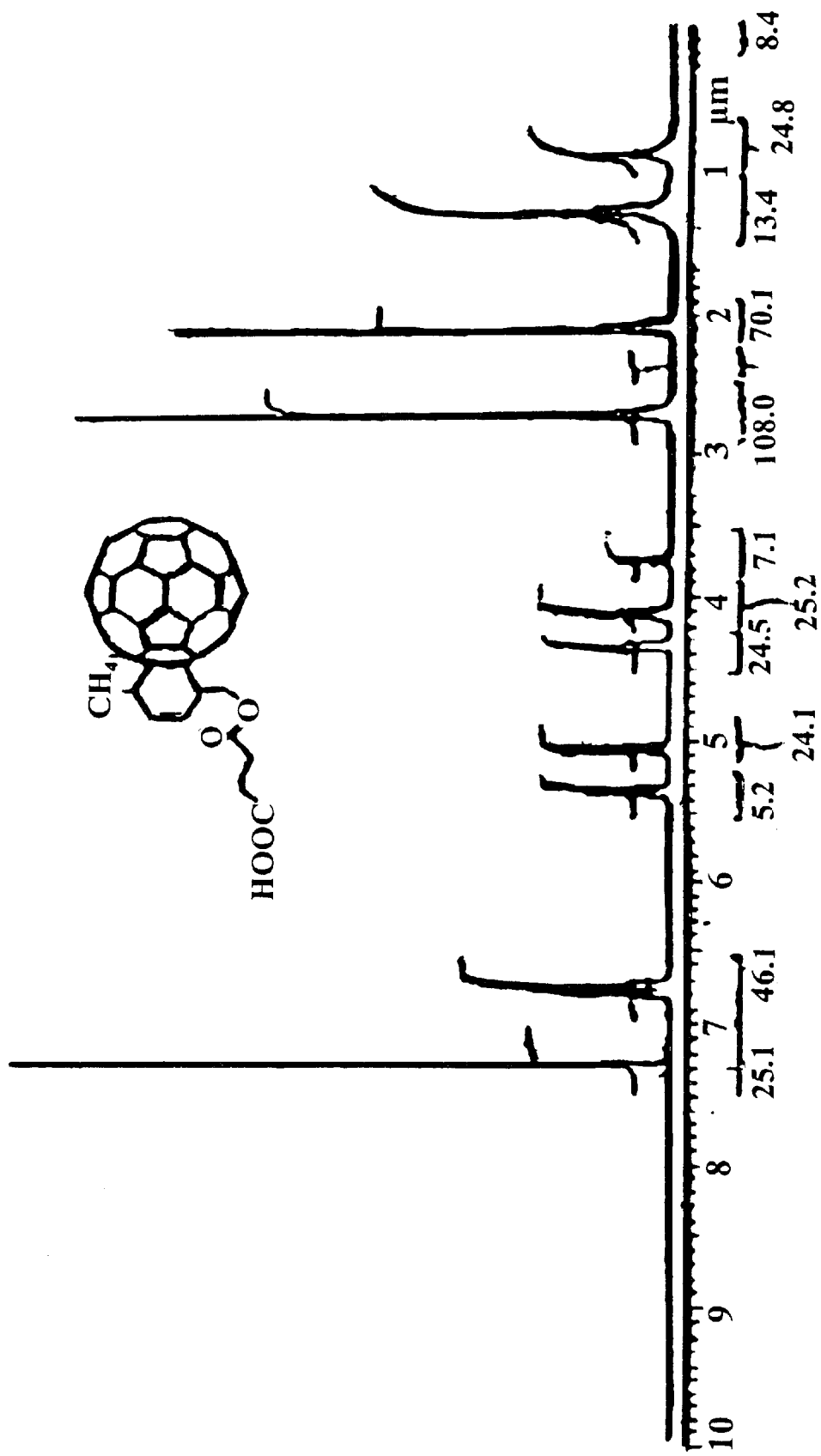
FIG. 19 H-NMR spectrum of the hemisuccinate derivative of C$_{80}$.
Figure 22:
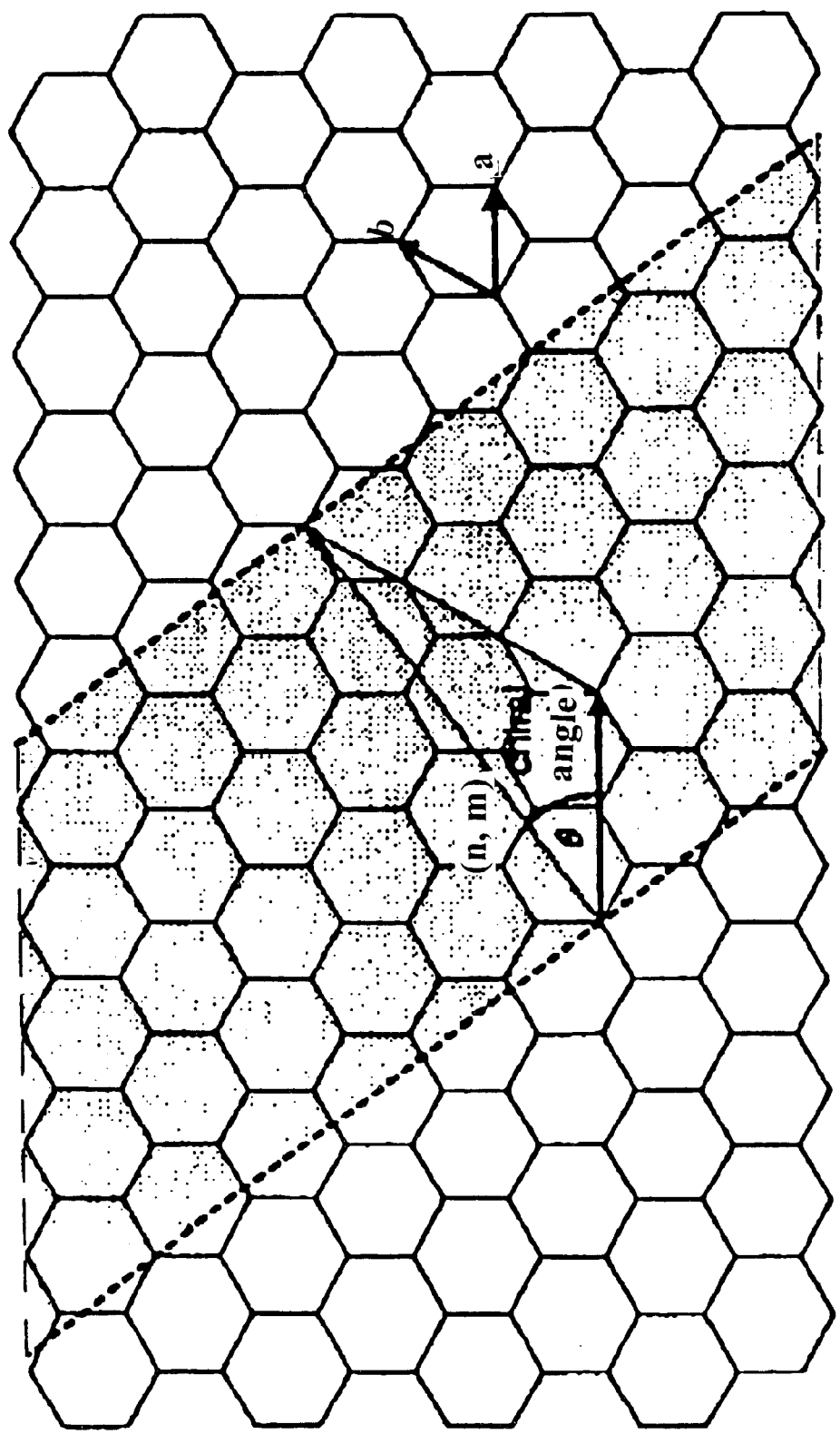
FIG. 22 During their formation nanotubes acquire caps with fullerene geometries. A rollup vector (n,m) specifies the oriented width, according to the number of steps along the a and b directions. (Boris I. Yakobson and Richard E. Smalley, "Fulierene Nanotubes: C$_{1000000}$ and Beyond," American Scientist, 85:324 (1997), hereby incorporated by reference).

To prepare the empty fullerene derivatives (Lu, 1995), trans-trans-2,4 hexadien-1ol was added to $C_{60}$ in toluene under inert atmosphere. The mixture was then heated to 80° C. overnight. After cooling, the solvent was removed. The residue was purified by flash column chromatography with toluene, followed by 20:1 toluene:ethyl acetate. That product was treated with dimethylaminopyridine and succinic anhydride under inert atmosphere in toluene:methylene chloride 1:1 solution. This mixture was warmed to 55° C. for one day, followed by cooling and solvent removal. The residue was purified by flash column chromatography with methylene chloride followed by methylene chloride:ethanol>15:1. The product, a dark brown solid, is shown in FIG. 19. These same steps will be followed for Ho@$C_{82}$.

While the procedure above creates a fullerene that remains water soluble only as long as the ester linkage remains intact, the F2 structure [see FIG. 13] results in a fullerene that is likely to remain water soluble under more adverse conditions. Its preparation is also a two step synthesis (Issacs and Diederich, 1993). This fullerene, or another ester-less derivative, may be used when maintenance of the solubility of fullerenes not bound to the Abf is desirable.

C.4 Task 4: Binding the Derivatized Ho@$C_{82}$ to the Fullerene Antibodies

As for the preparation of the hemisuccinate derivative, the procedure for binding the Ho@$C_{82}$ derivative to the Abf follow the procedure established for the empty fullerenes. The procedure for linking the Ho@$C_{82}$ hemisuccinate to the RSA and pentalysine proceeds via reaction with N-hydroxysuccinimide and dicyclohexylcarbodiimide in pyridine. After two days at room temperature, crystals of dicyclohexylurea (a by-product of the reaction) needs to be removed by centrifugation, leaving a solution of the fullerene N-hydroxysuccinimide ester (NHS). Half of the solution will be allowed to react with RSA at a ratio of 15:1 Ho@$C_{82}$-NHS:RSA. The other half will be allowed to react with pentalysine at a ratio of 5:1. This results in 10–12 metallofullerenes per molecule of RSA and 2.5 to 3 metallofullerenes per pentalysine.

Similarly, studies of its binding, and inhibition of its binding are carried out in precisely the same manner described in Section B.3. In the direct binding study, the ELISA plate will be coated with Ho@$C_{82}$-RSA. In analogy to the previous experiments, also tested is inhibition of binding of antibody to $C_{60}$-RSA by Ho@$C_{82}$-RSA and Ho@$C_{82}$-(lys)$_5$. These tests confirm the binding of a metallofullerene to a fullerene antibody.

REFERENCES FOR FOURTH SERIES OF EXPERIMENTS

Arano, Y., K. Wakisaka, Y. Ohmono et al. (1996). "Assessment of radiochemical design of antibodies using an ester bond as the metabolizable linkage: evaluation of maleimidoethyl 3-(Tri-n-butylstannyl)hippurate as a radioination reagent of antibodies for diagnostic and therapeutic applications," *Biconjugate Chem.* 7, 628–637.

Bethune, D. S., R. D. Johnson, J. R. Salem, M. S de Vries and C. S. Yannoni (1993). "Atoms in carbon Cages: the Structure and Properties of Endohedral Fullerenes," *Nature* 366, 123.

Buchanan, M. V., and R. L. Hettich (1993). *Anal. Chem.* 65, 245A.

Chai, Y., T. Guo, C. Jin, R. E. Haufler, L. P. F. Chibante, J. Fure, L. Wang, J. M. Alford, and R. E. Smalley (1991). "Fullerenes with Metals Inside," *J. Phys. Chem.* 95, 7564.

Chiang, L. Y., J. W. Swirczewski, C. S. Hsu, S. K. Chowdhury, S. Cameron, and K. Creegan (1992). "Multihydroxy Additions onto $C_{80}$ Fullerene Molecules," *J. Chem. Soc. Chem. Commun.,* 1791.

Coloma, M. J. and S. L. Morrison (1997). "Design and production of novel tetravalent bispecific antibodies," *Nat. Biotechnol.* 15, 125–126.

DeNardo, S., P. Gumerlock, M. Winthrop, P. Mack, S. Chi, K. Lamborn et al. (1995) "Yttrium- 90 Chimeric L6 Therapy of Human Breast Cancer in Nude Mice and Apoptosis-related Messenger RNA Expression," *Cancer Research* 55, 125–126.

Dugan, L., D. Turetsky, C. Du, et al. (1997). "Carboxyfullerenes as neuroprotective agents," *Proc. Natl. Acad. Sci. USA* 94, 9434–9439.

Erlanger, B. F. (1980). "Preparation of Antigenic Hapten-Carrier Conjugates," *Methods in Enzymology* 70(85).

Friedman, S. H., D. L. DeCamp, R. P. Sijbesma, G. Srdanov, F. Wudl, and G. L. Kenyon (1993). "Inhibition of the HIV-1 Protease by Fullerene Derivatives: Model Building Studies and Experimental Verification," *J. Am. Chem. Soc.* 115, 6506.

Gansow, O. A., M. W. Brechbiel, S. Mirzadeh, D. Colcher, and M. Roselli (1990). "Chelates and Antibodies: Current Methods and New Directions," in *Chancer Imaging with Radiolabeled Antibodies,* D. M. Goldenberg, editor, Kluwer Academic Publishers, P. 153.

Gecker, K. E. and A. Hirsh (1993). "Polymer-Bound $C_{60}$" *J. Am. Chem. Soc.* 115, 3850.

Glentworth, P., Betts (1961). "The effect of beta decay on the exchange properties of the rare earth—E D T A complexions," *Can. J. Chem.* 39, 1049.

Glentworth, P., C. Wright (1969). "Chemical effects of nuclear transformations of complexed metal atoms—I. The beta-decay of Ce-144 and Ce-143 complexed with polyaminocarboxylic acid chelating ligands," *J. Inorg. Nucl. Chem.* 31, 1263.

Gromov, A., W. Kratschmer, N. Krawez et al (1997). "Extraction and HPLC purification of Li@$C_{60/70}$," *Chem. Commun.,* 2003–4.

Haufler, R. E. (1994). "Techniques of Fullerene Production," in *Fullerenes: Recent advances in the Chemistry and Physics of Fullerenes and Related Materials,* K. D. Kadish and R. S. Ruoff, Editors, p. 50, The Electrochemical Society Press, Pennington, N.J.

Heath, J. R., S. C. O'Brien, Q. Zhang, Y. Liu, R. F. Curl, H. W. Kroto, F. K. Tittel, and R. E. Smalley (1985). "Lanthanum complexes of Spheroidal Carbon Shells", *J. Am. Chem. Soc.* 107, 7779.

Hnatowich, D. J., F. Virzi, M. Rusckowski (1987). "Investigations of Avidin and Biotin for Imaging Applications," *J. Nucl. Med.* 28, 12294–1302222.

Isaacs, L. And F. Diederich (1993). "Structures and Chemistry of Methanofullerenes: A Versatile Route into N-[(Methanofullerene)caronyl]-Substituted Amino Acids", *Helv. Chem. Acta.* 76, 2454.

Junghans, R. P., d. Dobbs, M. W. Brechbiel, S. Mirzadeh, A. A. Raubitschek, O. A. Gansow, and T. A. Waldmann (1993). "Pharmokinetics and Bioactivity of 1, 4, 7, 10-tera-azacyclododecane N $N^I$, $N^{II}$, $N^{III}$-tetraacetic acid (DOTA)-Bismuth-conjugated Anti-Tac Antibody for α-Emitter ($^{212}$Bi) Therapy," *Cancer Res.* 53, 5683.

Karam, L. R., M. Mitch, B. Coursey (1997). "Encapsulation of $^{99m}$Tc within Fullerenes: a Novel Radionuclide Carrier," *App. Radiat. Isot.* 48 (16), 771–776.

Kikuchi, K., K. Kobayashi, K. Sueki, S. Suzuki, H. Nakahara, and Y. Achiba (1994). "Encapsulation of Radioactive $^{150}$Gd and $^{161}$Tb Atoms in Fullerene Cages," *J. Am. Chem. Soc.* 116, 9775.

Klein, K., T. Nguyen, P. Larogue et al. (1989). "Yttrium-90 and Iodine-131 Radioimmunoglobulin Therapy of an Experimental Human Hepotoma," *Cancer Research* 49, 6383–6389.

Kratschmer, W., L. D. Lamb, K. Fostiropoulos, and D. R. Huffman (1990). "Solid $C_{60}$: A New Form of Carbon", *Nature* 347, 354.

Kroto, H. W., J. R. Heat., S. C. O'Brien, R. F. Curl, and R. E. Smalley (1985). "$C_{80}$Buckminsterfullerene", *Nature* 318, 162

Le Doussai, J. M., M. Martin, E. Gautherot, M. Delaage, J. Barbet (1989). "In vitro and in vivo targeting of radiolabeled monovalent and divalent haptens with dual specificity monoclonal antibody conugates: enhanced divalent hapten affinity for cell-bound antibody conjugate,: *J. Nucl. Med.* 30, 1358–1366.

Leu, J. G., Chen B-X., Diamanduras, A. W., Erlanger, B. Proc. (1994). "Idiotypic mimcry and the assembly of a supramolecular structure; an antidiopic antibody that mimics taxol in its tububulin-microtubulin interactions," *Natl. Acad. Sci USA* 91, 10690.

Li, M. C. Meares, Q. Salako et al. (1995). "Prelabeling of chimeric Monoclonal Antibody L6 with 90Yttrium- and 111Indium-1,4,7,10-tetraazacyclododecane-N, NI, NII, NIII -tetraacetic acid (DOTA) Chelates for Radioimmuno-diagnosis and Therapy," *Cancer Research* 55, 5726–5728.

Lu, Q. Y. (1995). PhD Thesis, New York University.

Meares, C. F. (1986). "Chelating Agents for the Binding of Metal Ions to Antibodies," *Nucl. Med. Bio.* 13, 311.

Paganelli, G. P. Manani, F. Zito, E. Villa, F. Sudati et al. (1991). "Three-step monoclonal antibody tumor targeting in carcinoembryonic antigenpositive patients," *Cancer Research* 51, 5960–5966.

Pluckthun, A., P. Pack (1997). "New protein engineering approaches to multivalent and bispecific antibody fragments," *Immunotechnology* 3, 83–105.

Renn, O., D. Goodwin, M. Studer, J. Moran, V. Jacques, C. Meares (1996). "New approaches to delivering metal-labeled antibodies to tumors: Synthesis and characterization of new ciotinyl chelate conjugates for pre-targeted diagnosis and therapy," *J. Of Controlled Release* 39, 239–249.

Rosebrough, S. F. (1993). "Plasma stability and pharmacokinetics of radiolabeled deferoxaminebiotin dreivatives," *J. Pharmcol. Exp. Ther.* 265, 408–415.

Rouvier, E. E. Gautherot, P. Meyer, and J. Barbet (1997). "Targeting medullary thyroid carcinomas with bispecific antibodies and bivalent haptens. Results and clinical perspectives," *Hormone Research* 47, 163–167.

Saunders, M., R. Cross, H. Jimenez-Vazquez, R. Simshi, A. Khong (1996). "Noble Gas Atoms Inside Fullerenes," *Science* 271, 1693–1697.

Scheinberg, D. A., and M. Strand (1982). "Leukemia cell targeting and therapy by monoclonal antibody targeting in erythrolellkemic mice," *Cancer Res.* 42, 44.

Schinazi, R. F., R. Sijbesma, G. Srdanov, D. L. Hill, and F. Wudl (1993). "Synthesis and Virucidal Activity of a Water-Soluble. Configurationally Stable, Derivatized $C_{60}$ Fullerene", *Antimicrobial Agents and Chemotherapy* 37, 1707.

Schinazi, R. F., A. McMillan, A. S. Juodawlkis, J. Phar, R. Sijbesma, G. Srdanov, J. C. Hummelen, F. D. Boudinot, C. L. Hill, and F. Wudl (1994). "Anti-Human Immunodefiency Virus, Toxicity in Cell Culture, and Tolerance in Mammals of a Water-Soluble Fullerene", in *Recent Advances in the Chemistry and Physics of Fullerenes and Related Materials,* ed., K. M. Kadish and R. S. Ruoff, The Electrochemical Society Proceedings v. 94–24, (The Electro-chemical Society, Inc. NJ.).

Schlom, J., K. Siler, IP). Milenic, S. Eggensperger, et al. (1991). "Monoclonal Antibody-based Therapy of a Human Tumor Xenograft with a $^{177}$Lutetium-labeled Immunoconjugate," *Cancer Research* 51, 2889–2896.

Sijbesma, R., G. Srdanov, F. Wudl, J. A. Castoro, C. Wilkings, S. H. Firedman, D. L. Decamp, and G. L. Kenyon (1993). "Synthesis of a Fullerene Derivative for the Inhibition of HIV Enzymes," *J. Am. Chem. Soc.* 115, 6510.

Sykes, T., V. Somayaji, S. Bier et al. (1997). "Radiolabeling of Monoclonal Antibody B43.13 with Rhenium-188 for Immunoradiotherapy," *Appl. Tadiat. Isot.* 48(7), 899–906.

Takata, M., B. Umeda, E. Nishibori, M. Sakata, Y. Saito, M. Ohno, and H. Shinghara (1995). "Confirmation by x-ray diffraction of the endohedral nature of the metallofullerene $Y@C_{82}$", *Nature* 377, 46.

Taylor, R. and D. R. M. Walton (1993). "The Chemistry of Fullerenes," *Nature* 363–685.

Virzi, F., P. Winnard, Jr., M. Fogarasi, T. Sano et al. (1995). "Recombinant Metallothionein-Conjugated Streptavidin Labeled with $^{188}$Re and $^{99m}$Tc," *Biconjugate Chem.* 6, 139–144.

Vuillez, J. Ph., D. Moro et al. (1997). "Two-step immunoscintigraphy for non-small-cell lung cancer staging using a bispecific anti-CEA/anti-indium-DPTA antibody and an indium- 111-labeled DPTA dimer.," *J. Nucl. Med.* 38, 507–511.

Wilder, R., G. DeNardo, S. DeNardo (1996). "Radioimmunotherapy: Recent results and future directions," *J. Of Clinlical Oncology* 144(4), 1383–1400.

Wurz, P. and K. R. Lykke, (1992). "Multiphoton Excitation, Ionization, and Dissociation of $C_{60}$," *J. Phys. Chem.* 96, 10129.

Yamakoshi, Y., T. Yagami, K. Fukuhara, S. Sueyoshi, N. Miyata (1994). "Solubillization of Fullerenes into Water with Polyvinylpyrrolidone Applicable to Biological Tests," *J. Chem. Soc., Chem. Commun.,* 517–518.

Yuanfang, Liu, Wu Chuanchu (1991). "Radiolabeling of monoclonal antibodies with metal chelates," *Pure and Appl. Chem.* 63 (3), 427–463.

---

What is claimed is:

1. A hybridoma cell line designated 1-10F-8A and deposited as ATCC accession number PTA-279.

2. A monoclonal antibody produced by the hybridoma of claim 1.

3. An antibody comprising an antigen-binding fragment of the monoclonal antibody of claim 2.

4. An isolated nucleic acid comprising a nucleotide sequence encoding an amino acid sequence as set forth in SEQ ID NO: 2.

5. The isolated nucleic acid of claim 4, wherein the nucleotide sequence is set forth in SEQ ID NO: 1.

6. An isolated nucleic acid comprising a nucleotide sequence encoding an amino acid sequence as set forth in SEQ ID NO: 4.

7. The isolated nucleic acid of claim 6, wherein the nucleotide sequence is set forth in SEQ ID NO: 3.

* * * * *

SEQUENCE LISTING

<160> NUMBER OF SEQ ID NOS: 4

<210> SEQ ID NO 1
<211> LENGTH: 404
<212> TYPE: DNA
<213> ORGANISM: mouse

<400> SEQUENCE: 1

```
atgggatgca gctgggcat  gctcttcctc ctgtcaataa ctgcaggtgt ccattgccag      60
gtccacctac aacaatctgg acctgagctg gtgaggcctg gggcctcagt gaagatttcc    120
tgcaaaactt ctggctacgt attcagtagt tcttggatga actgggtgaa acagaggcct    180
ggacagggtc ttaagtggat tggacgaatt tatcctggaa atggaaatgg aaatactaat    240
tacaatgaga aattcaaggg caaggccaca ctgactgcag acaaatcctc caacacagcc    300
tacatgcagc tcagcagcct gacctctgtg gactctgcgg tctatttctg tgcaacatcc    360
tcggcttact ggggccaagg gactctgctc actgtctctg cagc                     404
```

<210> SEQ ID NO 2
<211> LENGTH: 132
<212> TYPE: PRT
<213> ORGANISM: mouse [murine]

<400> SEQUENCE: 2

Met Gly Cys Ser Trp Gly Met Leu Phe Leu Leu Ser Ile Thr Ala Gly
1               5                   10                  15

Val His Cys Gln Val His Leu Gln Gln Ser Gly Pro Glu Leu Val Arg
            20                  25                  30

Pro Gly Ala Ser Val Lys Ile Ser Cys Lys Thr Ser Gly Tyr Val Phe
        35                  40                  45

Ser Ser Ser Trp Met Asn Trp Val Lys Gln Arg Pro Gly Gln Gly Leu
    50                  55                  60

Lys Trp Ile Gly Arg Ile Tyr Pro Gly Asn Gly Asn Thr Asn Tyr Asn
65                  70                  75                  80

Glu Lys Phe Lys Gly Lys Ala Thr Leu Thr Ala Asp Lys Ser Ser Asn
                85                  90                  95

Thr Ala Tyr Met Gln Leu Ser Ser Leu Thr Ser Val Asp Ser Ala Val
            100                 105                 110

Tyr Phe Cys Ala Thr Ser Ser Ala Tyr Trp Gly Gln Gly Thr Leu Leu
        115                 120                 125

Thr Val Ser Ala
    130

<210> SEQ ID NO 3
<211> LENGTH: 324
<212> TYPE: DNA
<213> ORGANISM: mouse

<400> SEQUENCE: 3
gatatccaga tgacacagac tacatcctcc ctgtctgcct ctctgggaga cagagtcacc      60
ttcagttgca gtgcaagtca ggatattaac aattatttaa actggtatca gcagaaacca     120
gatggaacta ttaaactcct aatctattac acatcaagtt tacgctcagg agtcccatca     180
aggttcagtg gtagtgggtc tgggacagat tattctctca ccatcaacaa cctggaacct     240
gaagatattg ccacttattt ttgtcagtat agtaggcttc cgttcacgtt cggctcgggg     300
acaaagttgg aaataaaacg taag                                            324

<210> SEQ ID NO 4
<211> LENGTH: 109
<212> TYPE: PRT
<213> ORGANISM: mouse

<400> SEQUENCE: 4

Asp Ile Gln Met Thr Gln Thr Thr Ser Ser Leu Ser Ala Ser Leu Gly
1               5                   10                  15

Asp Arg Val Thr Phe Ser Cys Ser Ala Ser Gln Asp Ile Asn Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Ser Leu Arg Ser Gly Val Pro Ser Arg Phe Ser Gly
    50                  55                  60

Ser Gly Ser Gly Thr Asp Tyr Ser Leu Thr Ile Asn Asn Leu Glu Pro
65                  70                  75                  80

-continued

```
Glu Asp Ile Ala Thr Tyr Phe Cys Gln Gln Tyr Ser Arg Leu Pro Phe
                85                  90                  95

Thr Phe Gly Ser Gly Thr Lys Leu Glu Ile Lys Arg Lys
            100                 105
```